(12) United States Patent
Britto et al.

(10) Patent No.: US 11,807,884 B2
(45) Date of Patent: *Nov. 7, 2023

(54) GENERATION-DEPENDENT SUPRAMOLECULAR ASSEMBLIES OF PROTEIN-DENDRON CONJUGATES

(71) Applicant: INDIAN INSTITUTE OF SCIENCE EDUCATION AND RESEARCH, Pune (IN)

(72) Inventors: Sandanaraj Selvaraj Britto, Pune (IN); Pavankumar Janardhan Bhandari, Pune (IN); Mullapudi Mohan Reddy, Pune (IN)

(73) Assignee: INDIAN INSTITUTE OF SCIENCE EDUCATION AND RESEARCH, Pune (IN)

(*) Notice: Subject to any disclaimer, the term of this patent is extended or adjusted under 35 U.S.C. 154(b) by 148 days.

This patent is subject to a terminal disclaimer.

(21) Appl. No.: 16/771,124

(22) PCT Filed: Dec. 8, 2018

(86) PCT No.: PCT/IN2018/050821
§ 371 (c)(1),
(2) Date: Jun. 9, 2020

(87) PCT Pub. No.: WO2019/111282
PCT Pub. Date: Jun. 13, 2019

(65) Prior Publication Data
US 2021/0163916 A1    Jun. 3, 2021

(30) Foreign Application Priority Data

Dec. 9, 2017 (IN) .............................. 201721044279

(51) Int. Cl.
*C12N 9/96* (2006.01)
*A61K 47/60* (2017.01)
(Continued)

(52) U.S. Cl.
CPC ................. *C12N 9/96* (2013.01); *A61K 47/59* (2017.08); *A61K 47/60* (2017.08); *C08G 83/008* (2013.01);
(Continued)

(58) Field of Classification Search
None
See application file for complete search history.

(56) References Cited

U.S. PATENT DOCUMENTS

2011/0065896 A1    3/2011  Licha et al.
2017/0231260 A1*   8/2017  Britto ............. C12Y 304/21001
424/1.69

FOREIGN PATENT DOCUMENTS

IN    201621005378    2/2017

OTHER PUBLICATIONS

Maartje M. C. Bastings, et al. Macrocyclization of enzyme-based supramolecular polymers† The Royal Society of Chemistry 2010 Chem. Sci., 2010, 1, 79-88 -79.
(Continued)

*Primary Examiner* — Karl J Puttlitz
(74) *Attorney, Agent, or Firm* — Kramer & Amado, P.C.

(57) ABSTRACT

The present invention discloses monodisperse protein-dendron conjugates that self-assemble to generation-dependent supramolecular protein assemblies of different size and surface charges. The invention further provides a process for synthesis of protein-dendron conjugates containing hydrophobic dendron of different generations.

7 Claims, 12 Drawing Sheets

(51) Int. Cl.
C08G 83/00 (2006.01)
C12N 9/64 (2006.01)
C12N 9/76 (2006.01)
A61K 47/59 (2017.01)
B82Y 5/00 (2011.01)

(52) U.S. Cl.
CPC ......... *C12N 9/6424* (2013.01); *C12N 9/6427* (2013.01); *C12Y 304/21001* (2013.01); *C12Y 304/21004* (2013.01); *C12Y 304/21062* (2013.01); *C12Y 304/21064* (2013.01); *B82Y 5/00* (2013.01)

(56) References Cited

OTHER PUBLICATIONS

Debora Bontempo and Heather D. Maynard* Streptavidin as a Macroinitiator for Polymerization: In Situ Protein-Polymer Conjugate Formation 6508 9 J. Am. Chem. Soc. 2005, 127, 6508-6509 10.1021/ja042230+ CCC: $30.25 © 2005 American Chemical Society.

Jeffrey D. Brodin et al. Metal-directed, chemically tunable assembly of one-, two- and three-dimensional crystalline protein arrays Nature Chemistry | vol. 4 | May 2012 | www.nature.com/naturechemistry.

Jonathan C. T. Carlson et al. Chemically Controlled Self-Assembly of Protein Nanorings 7630 9 J. Am. Chem. Soc. 2006, 128, 7630-7638 American Chemical Society.

Christine Lavigueur et al. Thermoresponsive giant biohybrid amphiphiles†a The Royal Society of Chemistry 2011 Polym. Chem., 2011, 2, 333-340.

Eun Seong Lee et al. A Virus-Mimetic Nanogel Vehicle 2008 Wiley-VCH Verlag GmbH & Co. KGaA, Weinheim Angew. Chem. Int. Ed. 2008, 47, 2418-2421.

Zhongyun Liu et al. Self-Assembled Biodegradable Protein-Polymer Vesicle as a TumorTargeted Nanocarrier 2014 American Chemical Society 2393 dx.doi.org/10.1021/am404734c Applied Materials & Interfaces ACS Appl. Mater. Interfaces 2014, 6, 2393-2400.

Carla S. Thomas et al. Solid-State Nanostructured Materials from Self-Assembly of a Globular Protein Polymer Diblock Copolymer vol. 5 ' No. 7 ' 5697-5707 ' 201 Department of Chemical Engineering, Massachusetts Institute of Technology © 2002 American Chemical Society.

Fanwen Zeng et al., "Dentrimers in Supramolecular Chemistry: From Molecular Recognition to Self-Assembly", Chem. Rev. 1997, 97, 1681-1712.

S. Rahima Benhabbour et al., Protein Resistance of PEG-Functionalized Dendronized Surfaces: Effect of PEG Molecular Weight and Dentron Generation: Macromolecules 2008, 41, 4817-4823, published on Jun. 6, 2008.

Jean M. J. Frechet, "Dendrimers and Other Dendritic Macromolecules: From Building Blocks to Functional Assemblies In Nanoscience and Nanotechnology", Journal of Polymer Science: Part A: Polymer Chemistry;, vol. 41, 3713-3725 (2003).

Akamol Klaikherd et al., "Comparison of Facially Amphiphilic Biaryl Dendrimers with Classical Amphiphilic Ones Using Protein Survace Recognition as the Tool", J. Am. Chem. Soc. 2006, 128,9231-9237 9 9231, published on Jun. 27, 2006.

Hugh Martin et al., "Nanoscale Protein Pores Modified with PAMAM Dendrimers", J. Am. Chem. Soc., 2007, 129 (31), pp. 9640-9649, DOI: 10.1021/ja0689029; published on Jul. 18, 2007.

Francesca Setaro et al., "Generation-Dependent Templated Self-Assembly of Biohybrid Protein Nanoparticles around Photosensitizer Dendrimers", Nano Lett., 2015, 15 (2), pp. 1245-1251, DOI: 10.1021/nl5044055, published on Jan. 23, 2015.

M.L. Patil et. al., "Multifunctional Triblock Nanocarrier (PAMAM-PEG-PLL) for the Efficient Intracellular siRNA Delivery and Gene Silencing", ACS Nano, 2011, 5 (3), pp. 1877-1887, DOI: 10.1021/nn102711d, published on Feb. 15, 2011.

Dan Luo et al., "Poly(ethylene glycol)-Conjugated PAMAM Dendrimer for Biocompatible, High-Efficiency DNA Delivery", Macromolecules 2002, 35, 3456-3462, Published on Mar. 27, 2002.

M.A. Zhuravel et al., "Dendronized Protein Polymers: Synthesis and Self-Assembly of Monodisperse Cylindrical Macromolecules", J. Am. Chem. Soc. 2004, 126, 9882-9883, Published on Jul. 24, 2004.

* cited by examiner

Gn =G1, G2, G3, G4

Gn =G1, G2, G3, G4

GENERATION-DEPENDENT SUPRAMOLECULAR ASSEMBLIES OF PROTEIN-DENDRON CONJUGATES

FIELD OF INVENTION

The present invention relates to monodisperse protein-dendron conjugates that self-assemble to generation-dependent supramolecular protein assemblies of different size and surface charges. The invention further provides a process for synthesis of protein-dendron conjugates containing hydrophobic dendron of different generations.

BACKGROUND AND PRIOR ART

The self-assembly of bio-macromolecules like proteins play a crucial role in molecular biology. Proteins, by forming assemblies, carry most functions in the cells. Inspired by nature's elegant and versatile protein architectures, researchers have tried to mimic nature by creating protein assemblies through various approaches.

The high tendency of proteins to aggregate and denature makes working with proteins a real challenge. Also, low yield of bio-conjugation reactions, heterogeneity in the product restricts the understanding of self-assembly process and the evolution of protein nanotechnology. Since biomolecules with diverse structural features like proteins are attractive building blocks for designing of nano-architectures with advanced functionalities, researchers around the world have continued to work and have reported various protein nanostructures.

Protein nanotechnology can be broadly classified into (a) genetic engineering based; and (b) synthetic strategy based.

Chemical modifications of proteins impart several additional features to protein like tailored amphiphilicity, different novel functionalities can be incorporated, different self-assembly patterns can be created. Different strategies have been reported to create protein polymer nanoparticles.

Bae and co-workers have reported virus mimetic nanogel. They have conjugated BSA to the mixed micelle of poly(histidine32-co-phenylalanine6) and poly(ethylene glycol)-b-poly(histidine) using succinyl ester group on polyethylene glycol [Lee, E. S.; Kim, D.; Youn, Y. S.; Oh, K. T.; Bae, Y. H. Angewandte Chemie International Edition 2008, 47, 2418].

A mutant red fluorescent protein, mCherryS131C, prepared by incorporation of a unique cysteine residue and site-specifically conjugated to end-functionalized poly(N-isopropylacrylamide) through thiol-maleimide coupling to form a welldefined model protein-polymer block copolymer is disclosed in the article titled 'Solid-state nanostructured materials from self-assembly of a globular proteinpolymer diblock copolymer' by Olsen BD. et.al in ACS Nano. 2011 Jul. 26; 5(7):5697-707.

Lavigueur and co-workers have coupled ethylene glycol methyl ether acrylate (EGMEA) and methoxy ethoxy ethyl acrylate (MEEA) random copolymer to EGFP and have shown to forms spherical aggregates at high temperature [Lavigueur, et.al in R. J. Polymer chemistry 2011, 2, 333].

Various other interactions are used in the art to drive protein assembly such as protein-metal interaction [Brodin, J. D. et.al Nature chemistry 2012, 4, 375; Bastings, M. M.; Chemical Science 2010, 1, 79]; interaction between protein domains [Carlson Journal of the American Chemical Society 2006, 128, 7630]; enzyme inhibitor interaction, and protein-cofactor interaction [Ringler, G. E. Science 2003, 302, 106].

The protein modifications with the polymers mentioned above impart heterogeneity to the product (i.e. ratio of protein to polymer is not one). This limits the characterisation of these assemblies to the near atomic resolution.

There are reports where protein modifications are homogeneous. Biodegradable protein-polymer conjugate prepared by covalently linking the tailor-made hydrophobic maleimide-functionalized poly(ε-caprolactone) (PCL) to hydrophilic bovine serum albumin (BSA) via the maleimide-sulthydryl coupling reaction to obtain self-assembled nanostructures based on amphiphilic protein-polymer conjugate is disclosed reported in ACS Appl. Mater. Interfaces, 2014, 6 (4), pp 2393-2400, titled 'Self-Assembled Biodegradable Protein-Polymer Vesicle as a Tumor-Targeted Nanocarrier' by Zhongyun Liu et.al.

Nolte and co-workers have reported the preparation of giant amphiphile in which protein acts as a polar head group and synthetic molecule as a nonpolar tail. The exposed disulfide of lipase was first reduced with DTT and coupled to the maleimide terminated polystyrene [Velonia, K.; Rowan, A. E.; Nolte, R. J. Journal of the American Chemical Society 2002, 124, 4224].

Even though the product is homogenous, the scope to change head group systematically is not possible, hence limits the study of the effect of protein, polymer, and linker on self-assembly. The present applicant in the patent application Indian patent application no. 201621005378 have disclosed site-selective modification by attaching small amphiphilic activity based probe (molecular weights ranging from 500 daltons to 1500 daltons) to the active site of serine protease. These conjugates were capable of forming supramolecular protein assemblies in the range of 8-12 nm.

However, a challenge still remains in appending dendrimers to the protein due to the high hydrophobicity of the dendrimers which can result in multiple labelling, low solubility etc; tendency to become globular at higher generation which leads to steric clash with protein. Purification and characterization of the protein conjugates are other challenges apart from the difficulties mentioned above.

OBJECT OF THE INVENTION

It is therefore the objective of the present invention to provide monodisperse protein-dendron conjugate which self-assemble to form protein based nanomaterials, for use in bionanotechnology application.

SUMMARY OF THE INVENTION

The above objective is met in the present invention by an active-site labelling of hydrophilic protein by the macromolecular activity-based probes (MAABP) of molecular weight 2-8 kDa. The MAABPs are composed of hydrophilic spacer with protein reactive group and the hydrophobic dendrimer. The resulting protein-dendron conjugates self-assemble to produce 3D nanostructures of various sizes depending upon the generation of dendrimer. The generation dependent supramolecular assemblies of protein-dendron conjugate finds application in the area of vaccine design, targeted drug delivery, in vivo diagnostics and synthetic biology and in general in bionanotechnology.

In an aspect, the present invention provides monodisperse protein-dendron conjugate of Formula (I) as depicted in Figure I which comprises the macromolecular amphiphilic activity-based probe (MAABPs) of molecular weight in the range of 2-8 kDa consisting of fluorophosphonate of monodisperse oligoethylene glycol as hydrophilic spacer (B) and G1-G4 hydrophobic dendrimers (C), conjugated to the active-site of hydrophilic protein (A); wherein the said monodisperse protein-conjugate self-assemble to generation dependent supramolecular protein assemblies of varying size and shape.

The hydrophilic protein (A) of said protein-dendron conjugate of Formula (I) is selected from the group consisting of serine proteases such as chymotrypsin, trypsin, subtilisin or proteinase K; cysteine proteases, aspartic proteases, metalloproteases, and such like or from fusion proteins composed of serine protease and other functional protein, antibody, peptide and the like.

The hydrophilic spacer (B) of said protein-dendron conjugate of Formula (I) binds covalently or non-covalently to the active site of the protein.

The hydrophobic dendrimer tail (C) of said protein-dendron conjugate of Formula (I) is dendron comprising of 2 tail benzyl ether dendrimer with alkyl terminal group, optionally substituted. In certain embodiments, benzyl ether dendrimer can also be 2 tail/3 tail benzyl ether dendrimer with alkyl terminal group, optionally substituted. The dendrimer induces self-assembly by noncovalent interaction such as hydrogen bonding and electrostatic interaction.

The protein-dendron conjugate of Formula (I) self assemble either alone or in a specified chemical environment to yield supramolecular protein assemblies depending on generation of the hydrophobic dendrimer.

In another aspect, the present invention provides a process for synthesis of monodisperse protein-dendron conjugate of Formula (I) which self-assemble to generation-dependent supramolecular protein assemblies comprising;

i. reacting the hydrophobic G1-G4 azide dendrimer dissolved in degassed solvent mixture with diphosphonate ester of oligoethylene glycol spacer using click chemistry followed by deprotection using oxalyl chloride to obtain monophosphonate ester intermediate;

ii. fluorinating the monophosphonate ester intermediate of step (i) with diethyl amino sulfur triflouride (DAST) to obtain G1-G4 macromolecular amphiphilic activity based probes (MAABP's);

iii. homogenizing the preweighed G1-G4 macromolecular amphiphilic activity based probes (MAABP's) of step (ii) with the hydrophilic protein (A) solution and scaling up the protein modification for self-assembling followed by purification to obtain generation dependent supramolecular assemblies of protein-dendron conjugate.

The diphosphonate ester of oligoethylene glycol spacer of step (i) is prepared by a process disclosed in Indian Patent application no. 201621005378.

The homogenization of the MAABPs with the hydrophilic protein (A) of the present invention comprises;

i. preparing the protein solution of 100 μM in 50 mM sodium phosphate pH 7.4;

ii. adding triton-X-100 and sodium phosphate buffer at pH 7.4 to preweighed macromolecular amphiphilic activity-based probes (MAABPs) consisting of hydrophilic spacer and hydrophobic dendrons and vortexing to obtain the clear solution;

iii. adding the protein solution of step (i) to the MAABPs solution of step (ii) and allowing to react on rotospin; and iv. scaling up the protein modification for self-assembling followed by purification to obtain supramolecular assemblies of protein-dendron conjugate.

DETAILED DESCRIPTION OF THE INVENTION

The invention will now be described in its various preferred as well as optional embodiments, so that the various aspects therein will be more clearly understood and appreciated.

The inventors discloses new chemical strategy for the design of well-defined monodisperse "protein-dendron conjugates", which self-assembles in to 3D nanostructure. This invention gives an opportunity to change protein head group, linker length, and dendrimer systematically; therefore helps to understand the effect of generation of dendrimer and protein size on the self-assembly which contributes further to make supramolecular protein assembly of defined shape and size.

The term "monodisperse protein-dendron conjugate" used in the entire specification means and relate to single macromolecular entity.

Figure 1:
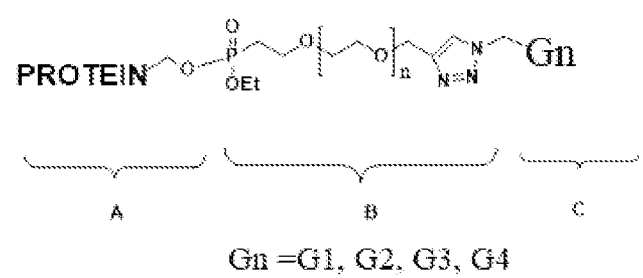
FIG. 1 depicts the monodisperse protein-dendron conjugate of Formula (I) and (a) depicts the monodisperse protein-dendron conjugate of Formula (IA).

In an embodiment, the present invention discloses monodisperse protein-dendron conjugates of Formula I as depicted in FIG. 1 which comprises the macromolecular amphiphilic activity-based probe (MAABPs) of molecular weight in the range of 2-8 kDa consisting of flurophosphonate of monodisperse oligoethylene glycol as hydrophilic spacer (B) and G1-G4 hydrophobic dendrimers (C), conjugated to the active-site of hydrophilic protein (A); wherein the said monodisperse protein-conjugate self-assemble to dendrimer generation dependent supramolecular protein assemblies of varying size and surface charges.

The hydrophilic protein (A) of said protein-dendron conjugate of Formula (I) is selected from the group consisting of serine proteases such as chymotrypsin, trypsin, subtilisin or proteinase K; cysteine proteases, aspartic proteases, metalloproteases, and such like or from fusion proteins composed of serine protease and other functional protein, antibody, peptide and the like. Preferably, the hydrophilic protein is selected from serine proteases such as chymotrypsin, trypsin, subtilisin or proteinase K.

The hydrophilic spacer (B) in said protein-dendron conjugate of Formula (I) preferably comprises of flurophosphonate of monodisperse cetylethylene glycol that binds covalently or non-covalently to the active site of the protein.

The hydrophobic dendrimer tail (C) of said protein-dendron conjugate of Formula (I) is dendron comprising of 2 tail benzyl ether dendrimer with alkyl terminal group, optionally substituted. In certain embodiments, benzyl ether dendrimer can also be 2 tail/3 tail benzyl ether dendrimer with alkyl terminal group, optionally substituted. The dendrimer induces self-assembly by non-covalent interaction such as hydrogen bonding and electrostatic interaction.

In an embodiment, the terminal surface of dendrimer (C) provides excellent multivalency which can be utilized for drug/therapeutic agent to covalently couple or non-covalently encapsulate within the protein-dendron nano-assemblies of the present invention. The therapeutic agent includes but is not limited to small molecule drug, peptide, siRNA, mRNA, DNA, protein, antibody, imaging agent etc.

The protein head group, spacer and dendrimer tail in said monodisperse protein-dendron conjugate can be systematically changed one at a time to make supramolecular protein assembly of defined shape and size. The protein-dendron conjugate of Formula (I) self-assemble either alone or in a specified chemical environment to yield supramolecular protein assemblies depending on generation of the hydrophobic dendrimer.

Figure 1A:
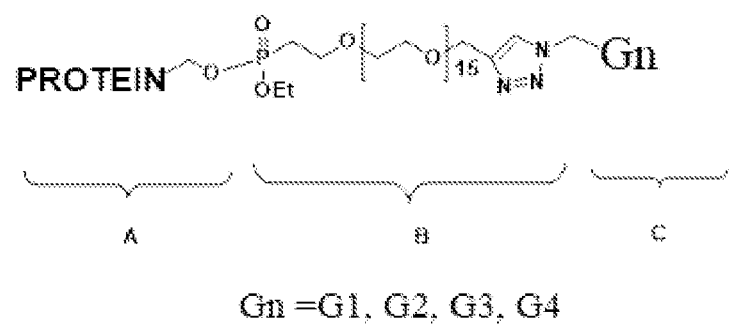
Figure 2:
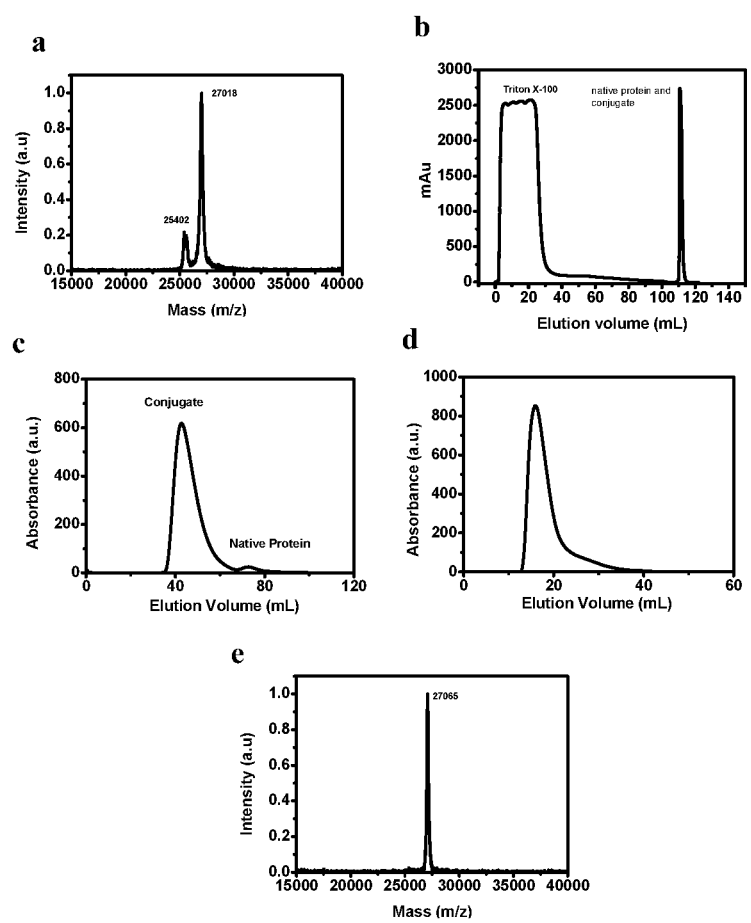
FIG. 2 (a) MALDI-ToF MS spectrum of reaction mixture, b. Ion exchange chromatogram, c. Size exclusion chromatogram, d. Desalting chromatogram, e. MALDI-ToF MS spectrum of purified conjugat of Chy-CEG-G1.
Figure 3:
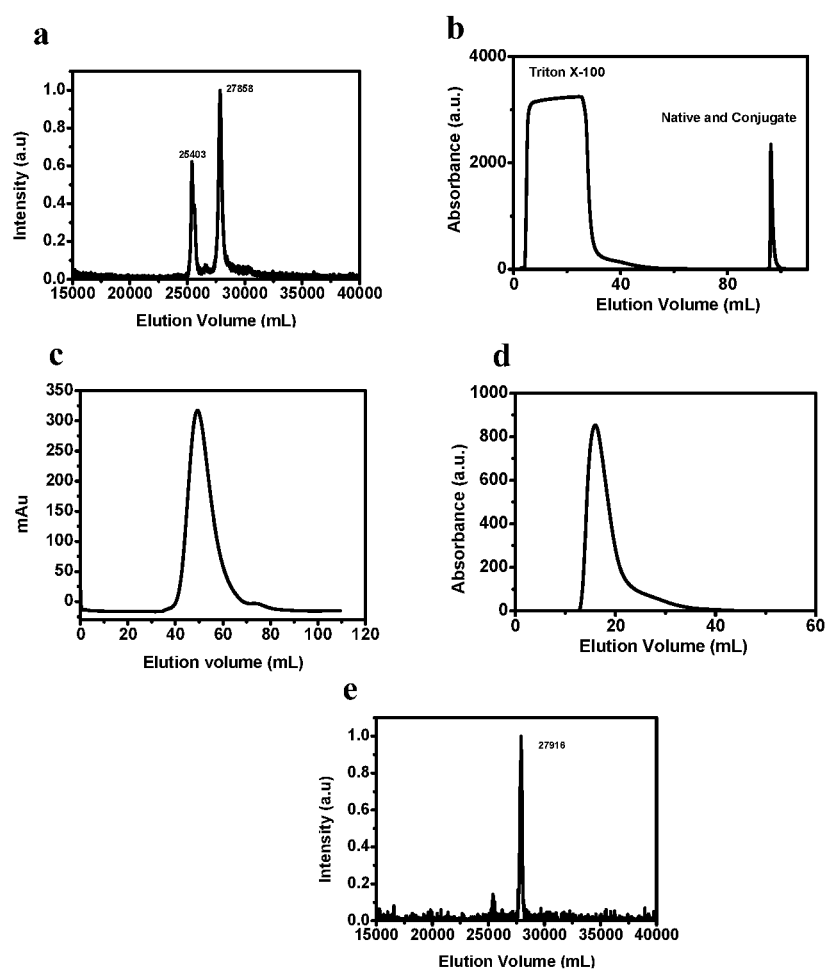
FIG. 3 (a) MALDI-ToF MS spectrum of reaction mixture, b. Ion exchange chromatogram, c. Size exclusion chromatogram, d. Desalting chromatogram, e. MALDI-ToF MS spectrum of purified conjugat of Chy-CEG-G2.
Figure 4:
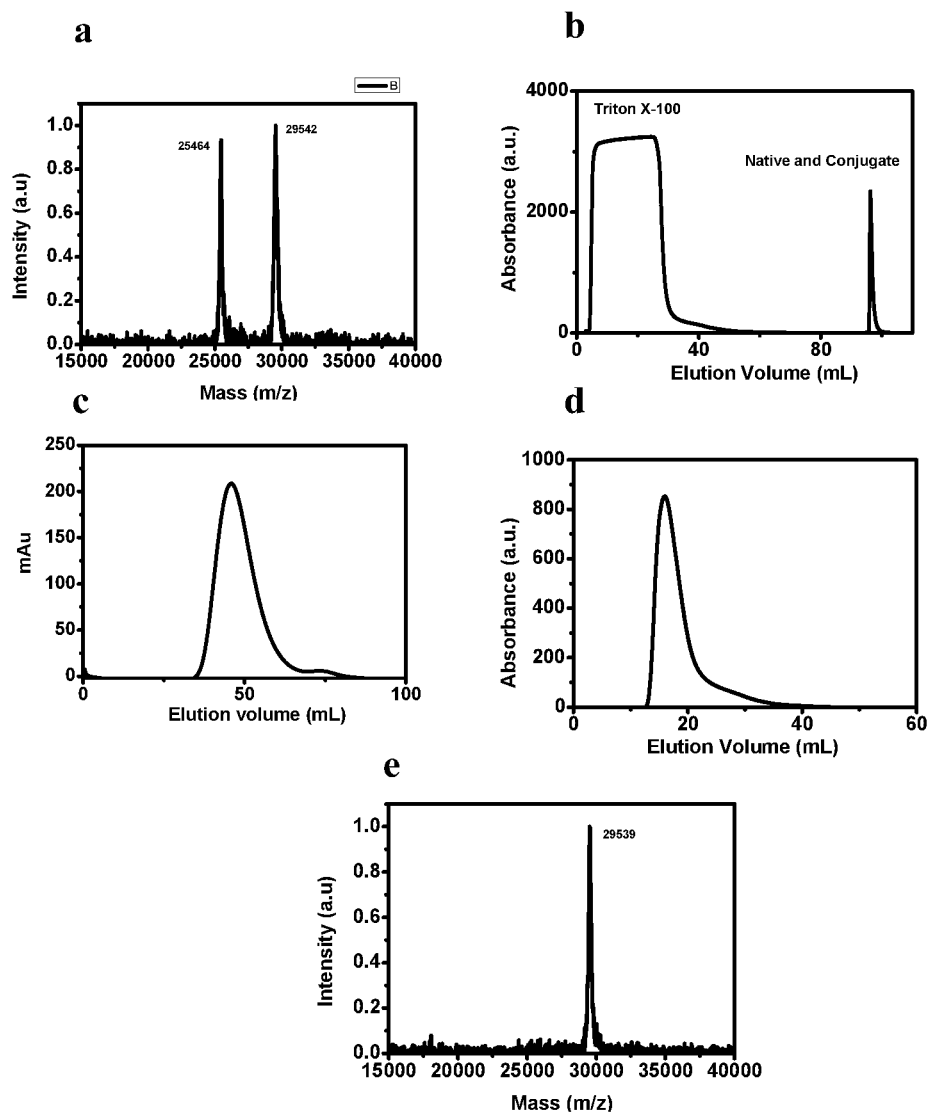
FIG. 4 (a) MALDI-ToF MS spectrum of reaction mixture, b. Ion exchange chromatogram, c. Size exclusion chromatogram, d. Desalting chromatogram, e. MALDI-ToF MS spectrum of purified conjugat of Chy-CEG-G3.
Figure 5:
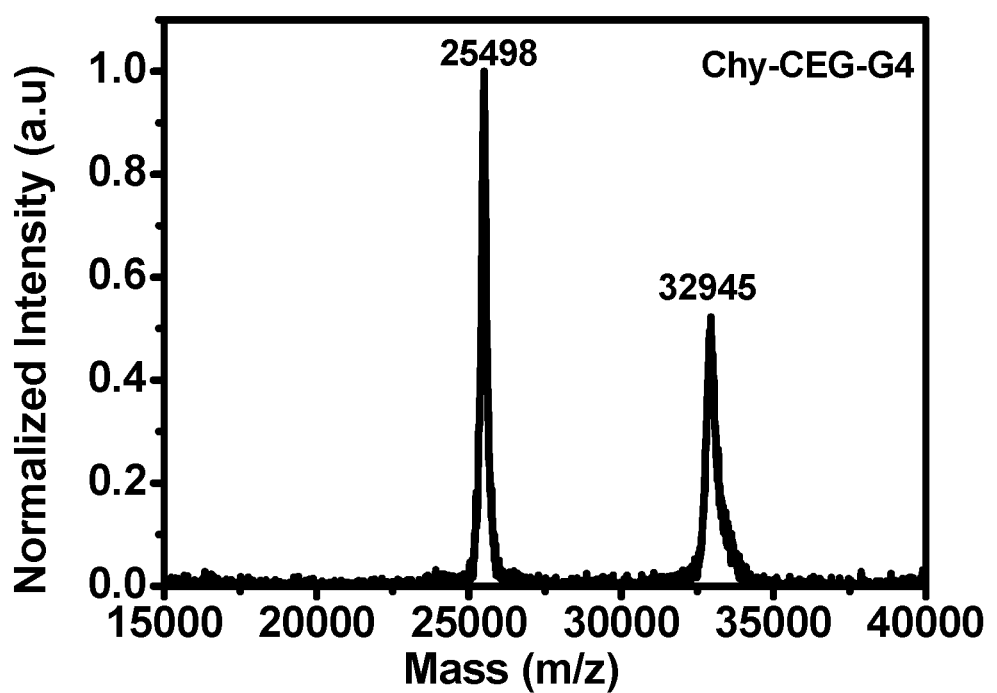
FIG. 5 MALDI-ToF MS spectrum of reaction mixture of chy-CEG-G4
Figure 6:
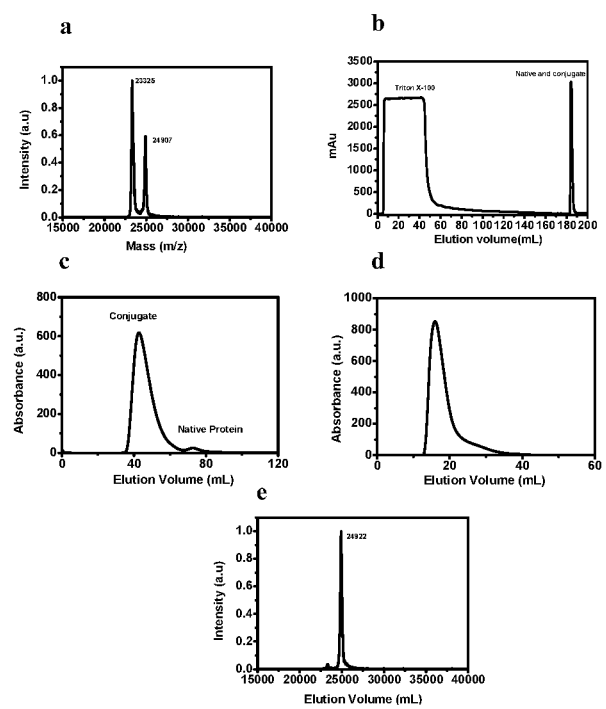
FIG. 6 (a) MALDI-ToF MS spectrum of reaction mixture, b. Ion exchange chromatogram, c. Size exclusion chromatogram, d. Desalting chromatogram, e. MALDI-ToF MS spectrum of purified conjugat of Try-CEG-G1.
Figure 7:
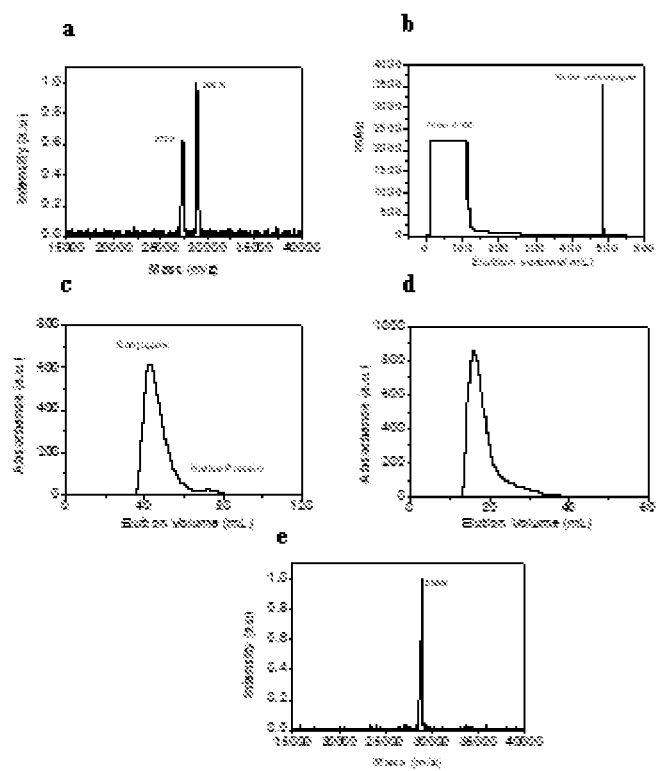
FIG. 7 (a) MALDI-ToF MS spectrum of reaction mixture, b. Ion exchange chromatogram, c. Size exclusion chromatogram, d. Desalting chromatogram, e. MALDI-ToF MS spectrum of purified conjugat of Sub-CEG-G1.
Figure 8:
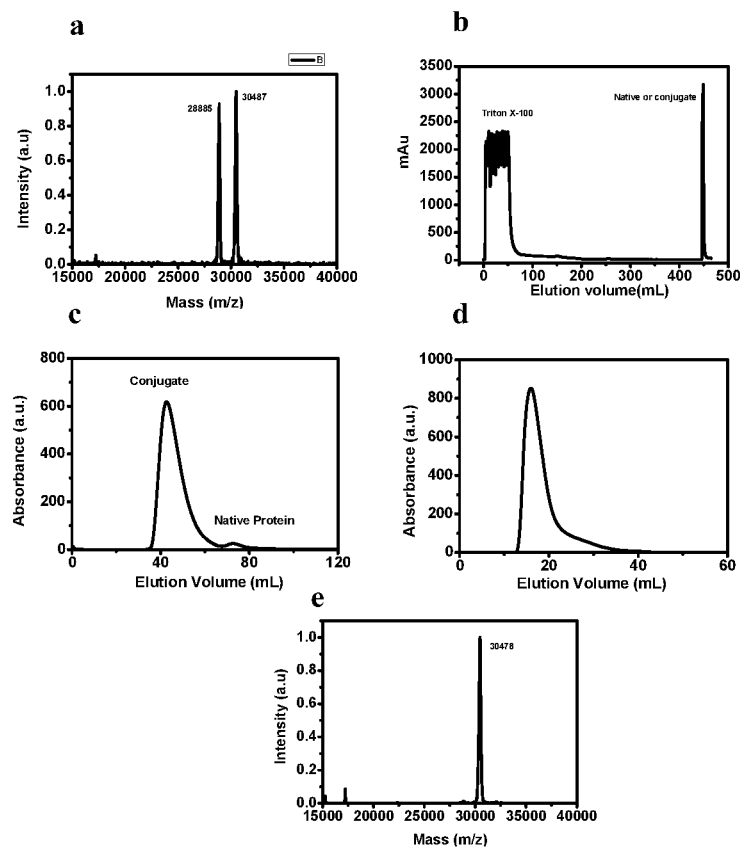
FIG. 8 (a) MALDI-ToF MS spectrum of reaction mixture, b. Ion exchange chromatogram, c. Size exclusion chromatogram, d. Desalting chromatogram, e. MALDI-ToF MS spectrum of purified conjugat of Pro K-CEG-G1.

In a preferred embodiment, the present invention discloses monodisperse protein-dendron conjugates of Formula IA as depicted in FIG. 1(a) which comprises the macromolecular amphiphilic activity-based probe (MAABPs) of molecular weight in the range of 2-8 kDa consisting of flurophosphonate of monodisperse cetylethylene glycol as hydrophilic spacer (B) and G1-G4 hydrophobic dendrimers (C), conjugated to the active-site of hydrophilic protein (A) selected from serine proteases such as chymotrypsin, trypsin, subtilisin or proteinase K; wherein the said monodisperse protein-conjugate self-assemble to dendrimer generation dependent supramolecular protein assemblies of varying size and shape.

In an embodiment, the hydrophobic dendrimers of the protein-dendron composition comprises 2 tail benzyl ether dendrimers (G1 to G4) represented by;

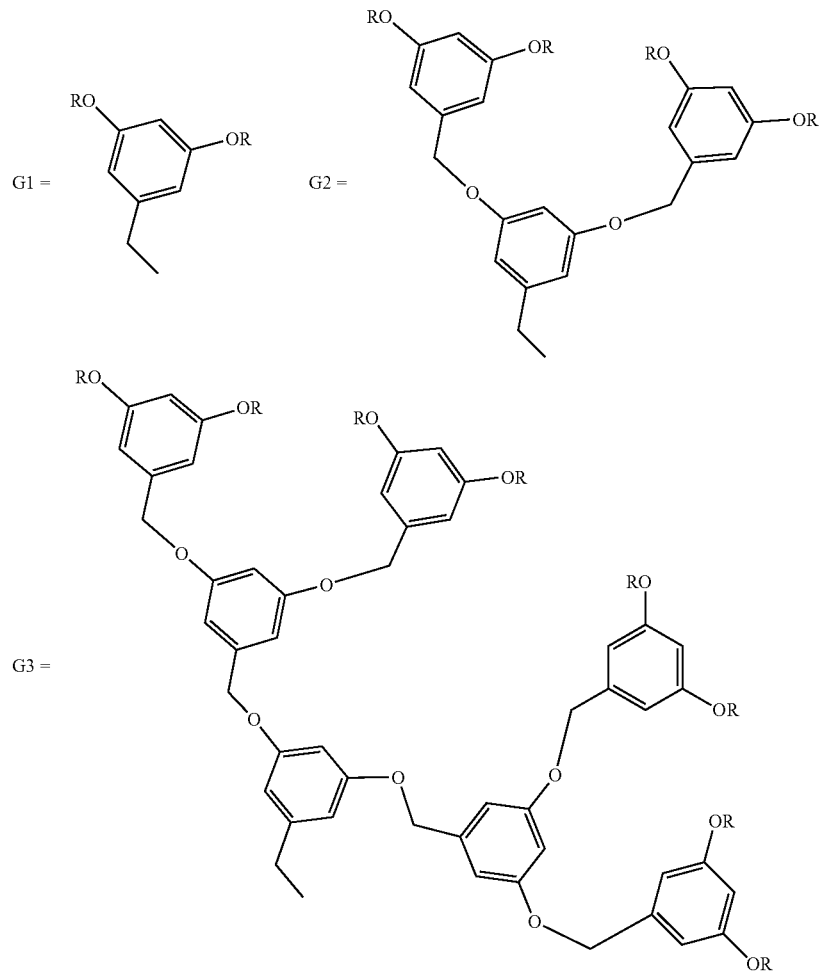

-continued

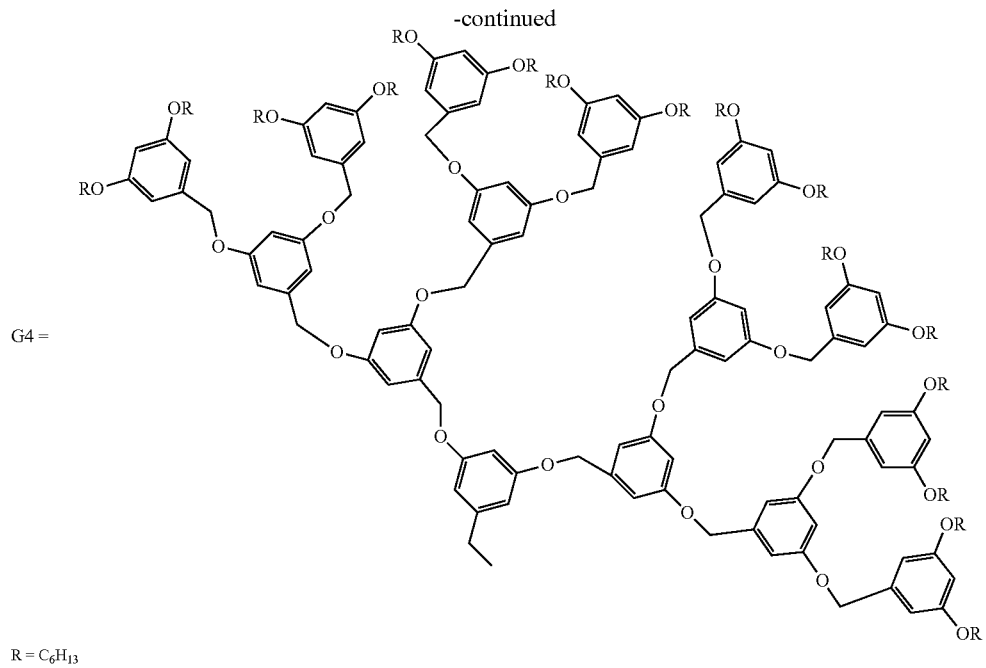

G4 =

R = C₆H₁₃

In yet another embodiment, the generation dependent supramnolecular protein assemblies of Formula (I) comprises;
i. conjugate of chymotrypsin and the MAABPs of (Chy-diethyl (1-(1-(3,5-bis((3,5-bis(hexyloxy)benzyl)oxy) benzyl)-1H-1,2,3-triazol-4-yl)-2, 5,8,11,14,17,20,23, 26,29,32,35,38,41,44,47-hexadecaoxanonatetracontan-49-yl) phosphonate);
ii. conjugate of chymotrypsin and the MAABPs of (Chy-diethyl (1-(1-(3,5-bis((3,5-bis((3,5-bis(hexyloxy)ben-zyl)oxy)benzyl)oxy)benzyl)-1H-1,2,3-triazol-4-yl)-2, 5,8,11,14,17,20,23,26,29,32,35,38,41,44,47-hexa deca oxa nonatetracontan-49-yl)phosphonate);
iii. conjugate of chymotrypsin and the MAABPs of (Chy-CEG-ethyl (1-(1-(3,5-bis((3,5-bis((3,5-bis((3,5-bis (hexyloxy) benzyl) oxy) benzyl)oxy)benzyl)oxy)ben-zyl)-1H-1,2,3-triazol-4-yl)-2, 5, 8, 11, 14, 17, 20, 23,26,29,32,35,38,41,44,47-hexadecaoxanonatetracon-tan-49-yl) phosphonate;
iv. conjugate of trypsin and the MAABPs of Try-diethyl (1-(1-(3,5-bis((3,5-bis(hexyloxy)benzyl)oxy)benzyl)-1H-1,2,3-triazol-4-yl)-2, 5, 8, 11, 14, 17, 20,23,26,29, 32,35,38,41,44,47-hexadecaoxanonatetracontan-49-yl) phosphonate;
v. conjugate of substilin and the MAABPs of (Sub-diethyl (1-(1-(3,5-bis((3,5-bis(hexyloxy)benzyl)oxy)benzyl)-1H-1,2,3-triazol-4-yl)-2,5,8,11,14,17, 20,23,26,29,32, 35,38,41,44,47-hexadecaoxanonatetracontan-49-yl) phosphonate);
vi. conjugate of proteinase K and the MAABPs of (ProK-diethyl (1-(1-(3,5-bis((3,5-bis(hexyloxy)benzyl)oxy) benzyl)-1H-1,2,3-triazol-4-yl)-2,5,8, 11,14,17,20,23, 26,29,32,35,38,41,44,47-hexadecaoxanonatetracontan-49-yl) phosphonate)

The size of the supramolecular assemblies of protein-dendron conjugates are highly generation-dependent ranging from 10-20 nm.

In another embodiment, the monodisperse protein-dendron conjugates of Formula (I) or Formula (IA) are synthesized by attaching MAABPs (composed of a flurophosphonate as a reactive group, hydrophilic linker, and hydrophobic dendrimer) to the proteins using micelle-assisted conjugation strategy (Indian patent application no. 201621005378) to attach hydrophobic dendrimer on to a globular protein.

Accordingly, the process for preparation of monodisperse protein-dendron conjugate of Formula (I) or Formula (IA) which self-assemble to generation-dependent supramolecular protein assemblies comprises;
i. reacting the hydrophobic G1-G4 azide dendrimer dissolved in degassed solvent mixture selected from THF/ H₂O (1:1) for G1-G2 azide and H₂O/CH₂Cl₂/THF (0.25:1:1) for G3-G4 azide with diphosphonate ester of oligoethylene glycol (OEG) spacer using click chemistry followed by deprotection using oxalyl chloride to obtain monophosphonate ester intermediate;
ii. fluorinating the monophosphonate ester intermediate of step (iii) with diethyl amino sulfur triflouride (DAST) to obtain G1-G4 macromolecular amphiphilic activity based probes (MAABP's);
iii. homogenizing the preweighed G1-G4 macromolecular amphiphilic activity based probes (MAABP's) of step (ii) with the hydrophilic protein solution and scaling up the protein modification for self-assembling followed by purification to obtain generation dependent supramolecular assemblies of protein-dendron conjugate.

The diphosphonate ester of cetyl ethylene glycol (CEG) spacer of step (i) is prepared by a process disclosed in Indian Patent application no. 201621005378. The homogenization process of the MAABPs with the hydrophilic protein (A) of the present invention comprises;
i. preparing the protein solution of 100 μM in 50 mM sodium phosphate pH 7.4;
ii. adding triton-X-100 and sodium phosphate buffer at pH 7.4 to preweighed macromolecular amphiphilic activity-based probes (MAABPs) consisting of hydrophilic spacer and hydrophobic dendrons and vortexing to obtain the clear solution;

iii. adding the protein (A) solution of step (i) to the MAABPs solution of step (ii) and allowing to react on rotospin;
iv. scaling up the protein modification for self-assembling followed by purifying the conjugate by IEX, SEC, and desalting to obtain supramolecular assemblies of protein-dendron conjugate.

The process for preparation of G1-G4 MAABPs is depicted in Scheme 1 below:

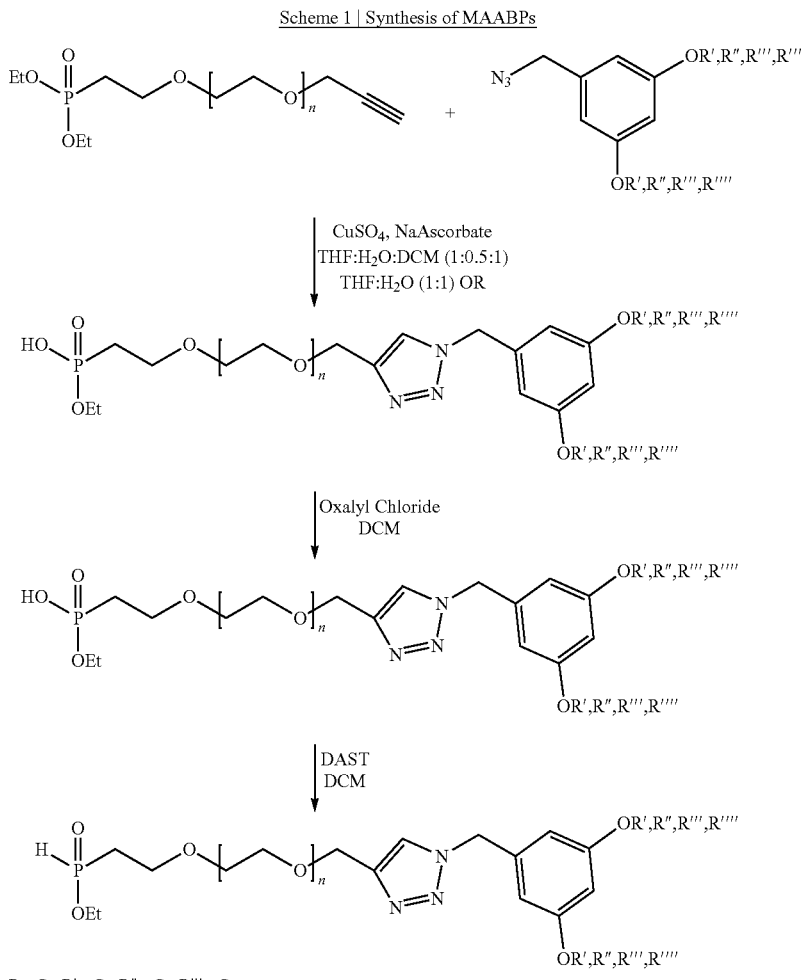

R = G1, R' = G2, R" = G3, R'" = G4,
n = 1-30

According to Scheme 1, in step (i) hydrophobic G1, G2 azides and diphosphonate ester of oligoethylene glycol (hydrophilic alkyne) were dissolved in degassed solvent THF/H$_2$O (1:1). The G3, G4-azide and and diphosphonate ester of cetyl ethylene glycol (CEG) (hydrophilic alkyne) were dissolved in degassed solvent H$_2$O/CH$_2$Cl$_2$/THF (0.25:1:1).) and stirred until clear solution was obtained. Freshly prepared 1M sodium ascorbate and 1M CuSO$_4$ were added to the reaction mixture at least thrice in an interval of about 45 minutes and allowed to react for several hours at RT. Upon completion of the reaction, the reaction mixture was extracted in solvent and the combined organic layer was dried, concentrated to get crude diphosphonate ester product which was further purified.

To the solution of diphosphonate ester intermediate of step (i) was added drop wise oxalyl chloride at room temperature and allowed to react for several hours under stirring. Upon completion, excess of oxalyl chloride and DCM (dichloromethane) were removed under vacuum. Water was added and the resulting mixture was extracted using solvent. The combined organic layer was dried to get crude mono phosphonate ester product which was used for next step without further purification.

Step (ii) comprises fluorinating the solution of crude mono phosphonate ester of step (i) by adding diethylaminosulfur triflouride (DAST) to the mono phosphonate ester. Excess of DAST and DCM were evaporated under reduced pressure after completion of the reaction. To the obtained residue, water was added and stirred to quench any residual DAST. The reaction mixture was extracted in solvent, the combined organic layers were dried to get the desired MAABPs which were used for protein modification without further purification.

In another embodiment, the process for preparation of hydrophobic G1-G4 azide used in the preparation of MAABPs by click chemistry comprises;
i. brominating the suitably substituted 2T benzyl alcohol using tetrabromomethane, triphenylphosphine in solvent at low temperature to get bromide compound;

ii. reacting the bromide of step (i) with sodium azide in solvent at low temperature to obtain the hydrophobic azide.

The process is depicted in Scheme 2 below

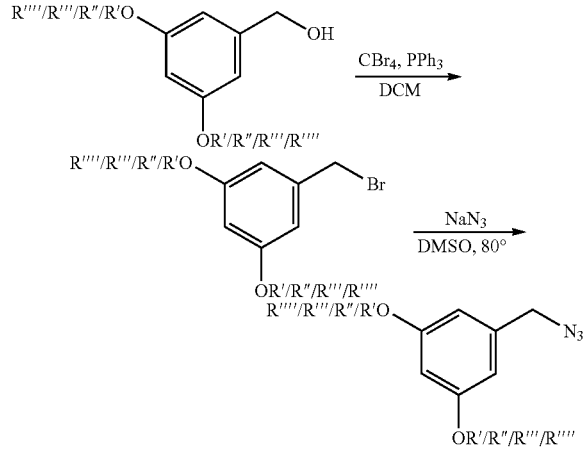

R = G0, R' = G1, R" = G2, R''' = G3, R'''' = G4

In another embodiment, the G1, G2, G3, G4 benzyl alcohol used in the preparation of hydrophobic azide are prepared by reacting the suitable bromide with 2,3 dihydroxy benzyl alcohol in presence of inorganic base and crown ether as shown below in Scheme 3.

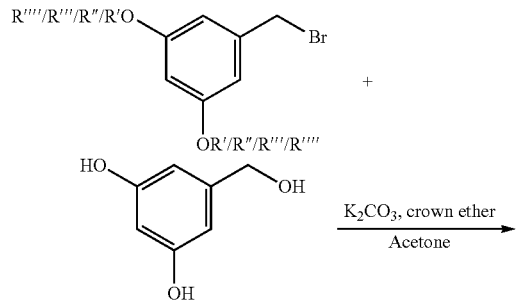

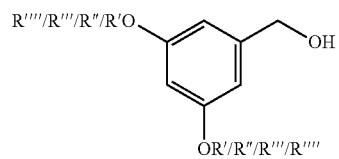

R' = G1, R" = G2, R''' = G3, R'''' = G4

The solvents used in the present process was selected from polar or non-polar protic or aprotic solvents such as lower alcohols, ethers such as dioxane, THF; DMF, halogenated hydrocarbons; ketones and the like.

The preparation of protein-dendron conjugate of the present invention capable of forming supramolecular assemblies comprises adding sodium phosphate buffer of pH 7.4 to the pre-weighed hydrophilic protein in a centrifuge tube. To another centrifuge tube was added the prep weighed G I-G4 macromolecular amphiphilic activity-based probes (MAABPs), triton X-100, sodium phosphate buffer of pH 7.4 and the mixture was vortexed till the solution becomes homogeneous. This was followed by adding the MAABPs to the protein solution, and then allowed to react on the rotospin. Scaling up the protein modification for self assembling followed by purifying the protein-G1-G4 dendron conjugate by TEX, SEC, and desalting to obtain supramolecular assemblies of protein-dendron conjugate.

In ion exchange chromatography (using suitable column) the column was preequilibrated using 50 mM sodium phosphate of pH: 7.4 and the sample was injected followed by post injection equilibration until the complete removal of triton X-100. This was followed by elution of the protein using 1M NaCl as elution buffer.

In size exclusion chromatography (SEC) suitable column (Sephacryl-300) was pre-equilibrated with 50 mM sodium phosphate with 1M NaCl for at least 2CVs (column volumes) and then sample was injected followed by post injection equilibration with the same for at least 2CVs again or until the complete elution of the proteins.

The purified protein-dendron conjugate was desalted in a column with Milli Q water for at least 2CVs until the complete elution of the proteins. The conjugate separated from salt was lyophilized quickly.

The process for preparation of protein-dendron conjugate of Formula (I) and Formula (IA) of the present invention is shown in Scheme 4 below:

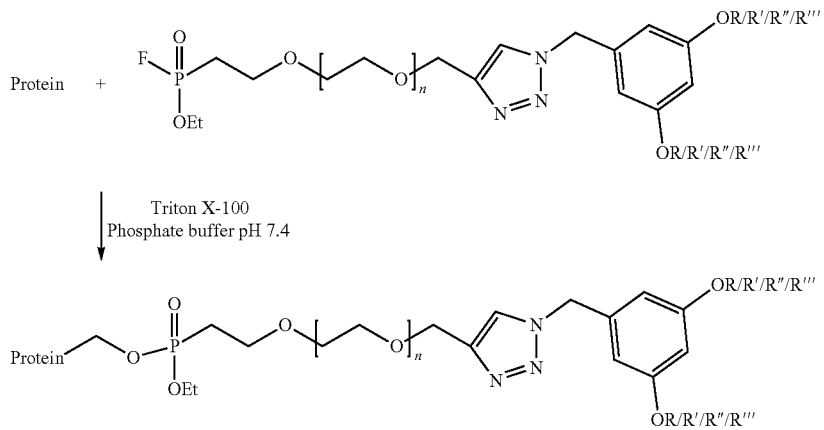

R = G0, R' = G1, R" = G2, R''' = G3
n = 1-30

The dynamic light scattering (DLS) and size-exclusion chromatography (SEC) studies revealed that self-assembly of protein-dendron conjugate can was be programmed to yield supramolecular protein assemblies with sizes of 10-20 nm with molecular weight ranging from 360 kDa to 690 kDa.

The DLS and SEC study further revealed that the assembly sizes and other characteristics are highly generation-dependent i.e. on the macromolecular amphiphilic activity-based probe conjugated to the protein. The size of protein-dendron complexes increases with increase in the generation which emphasizes the effect of dendrimer volume on the size of protein-dendron complexes. The SEC studies reveals that the protein-dendron conjugates eluted at lower elution volumes indicating the large protein complexes formation.

In an embodiment, the present invention relates to a composition comprising generation dependent supramolecular assemblies of protein-dendron conjugate of Formula (I) or Formula (IA) and other pharmaceutically acceptable excipients which find applications in the area of vaccine design, targeted drug delivery, in vivo diagnostics, synthetic biology and in general in bionanotechnology.

In another embodiment, the advantageous feature of present invention is that the invention provides well-defined monodisperse "protein-dendron conjugates", which self-assembles in to 3D nanostructure. The present invention provides the opportunity to change protein head group, linker length, and dendrimer systematically; therefore helps to understand the effect of generation of dendrimer and protein size on the self-assembly which contributes to make supramolecular protein assembly of defined shape and size. Further, the terminal surface of dendrimer (C) provides excellent multivalency which can be utilized for drug/therapeutic agent to covalently couple or non-covalently encapsulate within the protein-dendron nano-assemblies of the present invention. The therapeutic agent includes but is not limited to small molecule drug, peptide, siRNA,mRNA, DNA, protein, antibody, imaging agent etc.

Further details of the present invention will be apparent from the examples presented below. Examples presented are purely illustrative and are not limited to the particular embodiments illustrated herein but include the permutations, which are obvious as set forth in the description.

(1) General Procedure for Synthesis and Purification of Protein-Dendron Conjugates The synthesis of protein-dendron conjugates of the present invention are categorized in two types (i) dendron variants, in which the protein (chymotrypsin) was kept constant, and dendrimer (G1-G4) was varied. (ii) Protein variants, in this the dendrimer (G1) was retained constant (G1), and protein (trypsin, subtilisin and proteinase K) was varied to explore their effect on self-assembly.

(1A): Protein Conjugation

Protein modification was carried out at the concentration of 100 μM, which was found to be optimum for MALDI-ToF MS monitoring. Triton X-100 was used to solubilize the MAABPs at concentrations 100 times (20 mM) more than critical micellar concentration (CMC) or 2% of total volume of reaction mixture. Typically, for test reactions, final volume of the reaction mixture was 1 mL. Proteins were weighed (2.3 to 2.9 mg, depending on protein) in microcentrifuge tubes and 500 μL 50 mM sodium phosphate pH 7.4 was added and mixed gently with a pipette to make 200 μM solutions. Then MAABPs (1 or 2 equivalents) were weighed in a different microcentrifuge tube, followed by addition of 20 μL of triton X-100 and 480 μL of 50 mM sodium phosphate pH 7.4 and vortexed for 15 minutes. When the MAABP solution became clear, the protein solution was added into MAABP solution to get 100 μM (1 mL) protein solutions and allowed to react for 24 h on rotospin at 20 rpm at 25° C. Protein modifications were carried out in falcon tubes at 200 mg scale following the linear scale up of above mentioned procedure for understanding the self-assembly behaviour.

(1B): Protein Conjugation Monitoring

To monitor the extent of protein modification, the samples were directly withdrawn from reaction mixture using a pipette, and analyzed. In brief, 2 μL of reaction mixture was mixed with 2 μL of 2% TFA and 2 μL of matrix mixture as previously stated, vortexed and spotted on MALDI-ToF MS plate. It is to be noted that the matrix preparation and sample preparation procedures remained same here.

(1C): Purification of Conjugates

All the conjugates were purified by three-step purification i.e. IEX, SEC and desalting, performed using either Aktaprime or Aktaprime plus or Akta Explorer or Akta Pure. IEX was performed to remove triton X-100 using either SP sepharose or Q sepharose resins (GE) depending on isoelectric point (pI) and surface charges of proteins (Try: 30.4, Chy: 19.5, Pro K: −8.4, Sub: −6.2 mV). For example, to purify the reaction mixture of trypsin or chymotrypsin, SP sepharose, a cation-exchange resin at pH 7.4 was used and to purify subtilisin and proteinase K Q sepharose, an anion-exchange resin at pH 10 was used. During cation-exchange chromatography, the column was pre-equilibrated with the same buffer (50 mM sodium phosphate pH 7.4) which was used for modification and then sample was injected followed by post injection equilibration for at least 2 Column Volumes (CVs) or until the complete removal of triton X-100 for large scale reactions. The elution of native protein and its corresponding conjugate together as mixture was later achieved using 50 mM sodium phosphate pH 7.4, 1 M NaCl as elution buffer.

In the case of anion-exchange chromatography, the protein reaction mixtures were buffer-exchanged first to 50 mM tris base pH 10 (since the buffer used for modification was 50 mM sodium phosphate pH 7.4). Then the anion-exchange column was pre-equilibrated using same buffer (50 mM tris base pH 10) which was used for buffer-exchange and then the sample was injected followed by post injection equilibration for at least 2 CVs or until the complete removal of triton X100 for large scale reactions. The elution of the native protein and its conjugate together as mixture was later achieved using 50 mM tris base pH 10, 1 M NaCl as elution buffer.

The obtained IEX fractions were subjected to SEC immediately to remove the native proteins from the protein conjugates. For the separation of native protein from protein conjugate, 50 mM sodium phosphate pH 7.4, 1 M NaCl was used as buffer using either Sephacryl S-100 HR 16/60 or Sephacryl S-200 HR 16/60 or Sephacryl S-300 HR 16/60. The NaCl was later removed by Sephadex-G25 desalting column. The desalted fractions were quickly lyophilized and later dissolved in required buffer when needed.

(1D): Molecular Weight Determination of Purified Protein-Dendron Conjugates

Monitoring of IEX, SEC and desalted fractions were carried out using the same procedure mentioned for native proteins and reaction mixtures except for the addition of triton X-100 in protein fractions. In short, 98 μL of samples from each fraction were mixed with 2 μL of triton X-100 (2% or 100 times the CMC) in a separate microcentrifuge tube and vortexed for 4 h. The samples were then analysed using the same procedure as mentioned above. The matrix and sample preparation procedure remain same.

(1E): Self-Assembly of Protein-Dendron Conjuagtes

The self-assembling property of protein-dendron conjugates was validated using complementary techniques such as analytical SEC, dynamic light scattering (DLS), size-exclusion chromatography coupled with multi-angle laser light scattering (SEC-MALS).

(2): General Synthesis and Purification of Compounds and their Intermediates:

All reagents were obtained commercially unless and otherwise stated. Reactions were performed in an oven dried round bottom flask (RBF) and under nitrogen atmosphere. Air and moisture sensitive solvents were transferred via syringe. Reactions were monitored by thin layer chromatography (TLC) and developed chromatogram was visualized by ultraviolet (UV) lamp or by phosphomolybdic acid (PMA) staining. Product purification was accomplished by 100-200 mesh size silica gel column chromatography.

All the compounds were characterized by $^1H$, $^{13}C$ and $^{19}F$ (in case of fluorinated compounds) nuclear magnetic resonance (NMR) using Bruker or Jeol 400 MHz. 1H and 19F were recorded at an operating frequency of 400 MHz and 100 MHz for 13C using, using TMS as an internal standered. All the 13C Chemical shifts were mentioned in parts per million (PPM) and measured relative to residual $CHCl_3$, $CH_3OH$ or $CH_3CN$ in their deuterated solvent. Coupling constants were reported in Hertz (Hz). Multiplicities were explained as s=singlet, d=doublet, t=triplet, q=quartet, m=multiplet, quint=quintet. Mass spectra were obtained with either the MALDI-TOF MS or HRMS. Room temperature varied between 21-35° C.

(2.2): Synthesis of Dendrimer (2.2.1): General Procedure for Synthesis of G1-G4 Azides 2.2. Synthesis Scheme 5 for G1 Dendrimer Azide

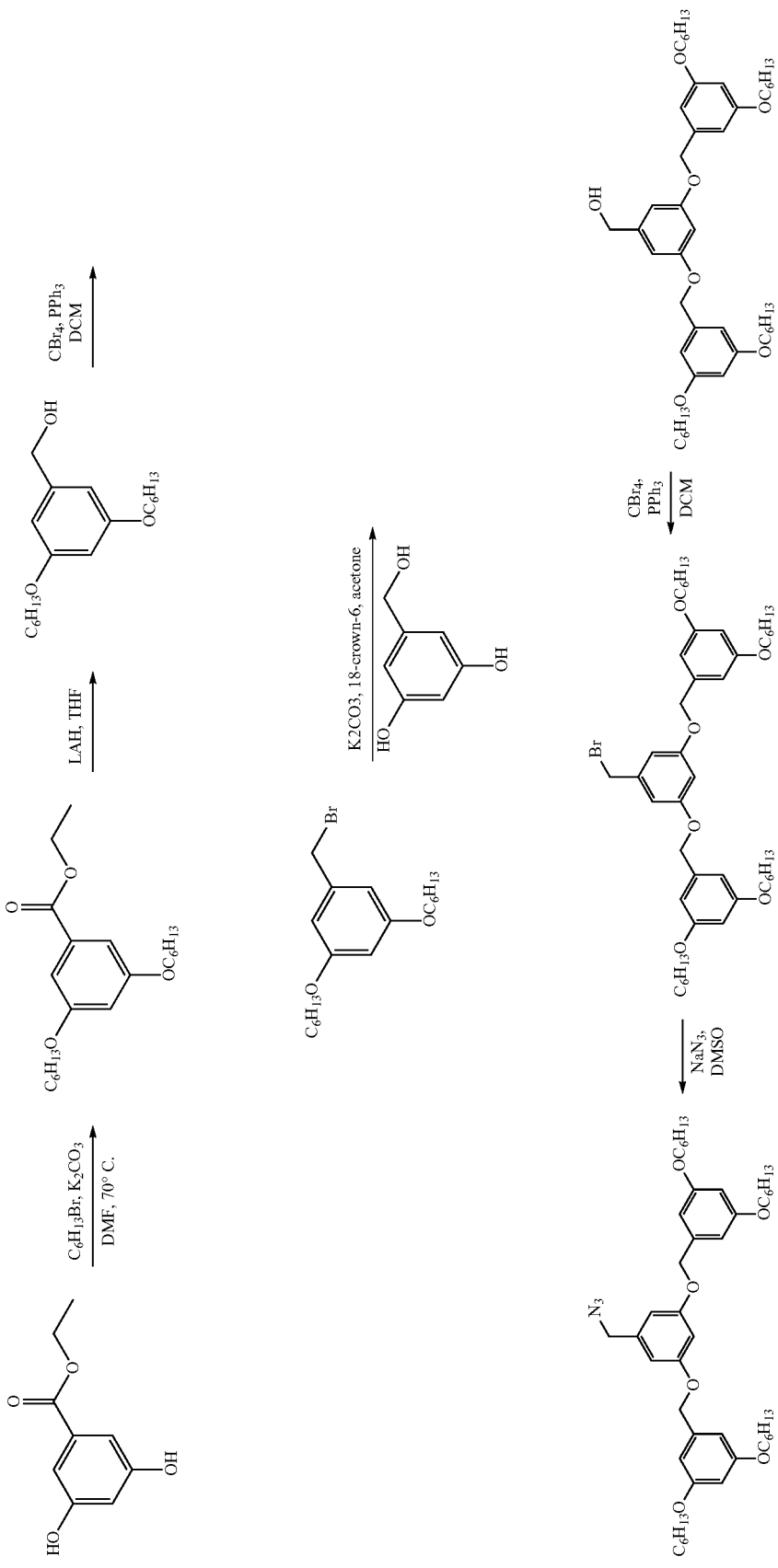

2.2.1. Synthesis Scheme 6 for G2-G4 Dendrimer Azide
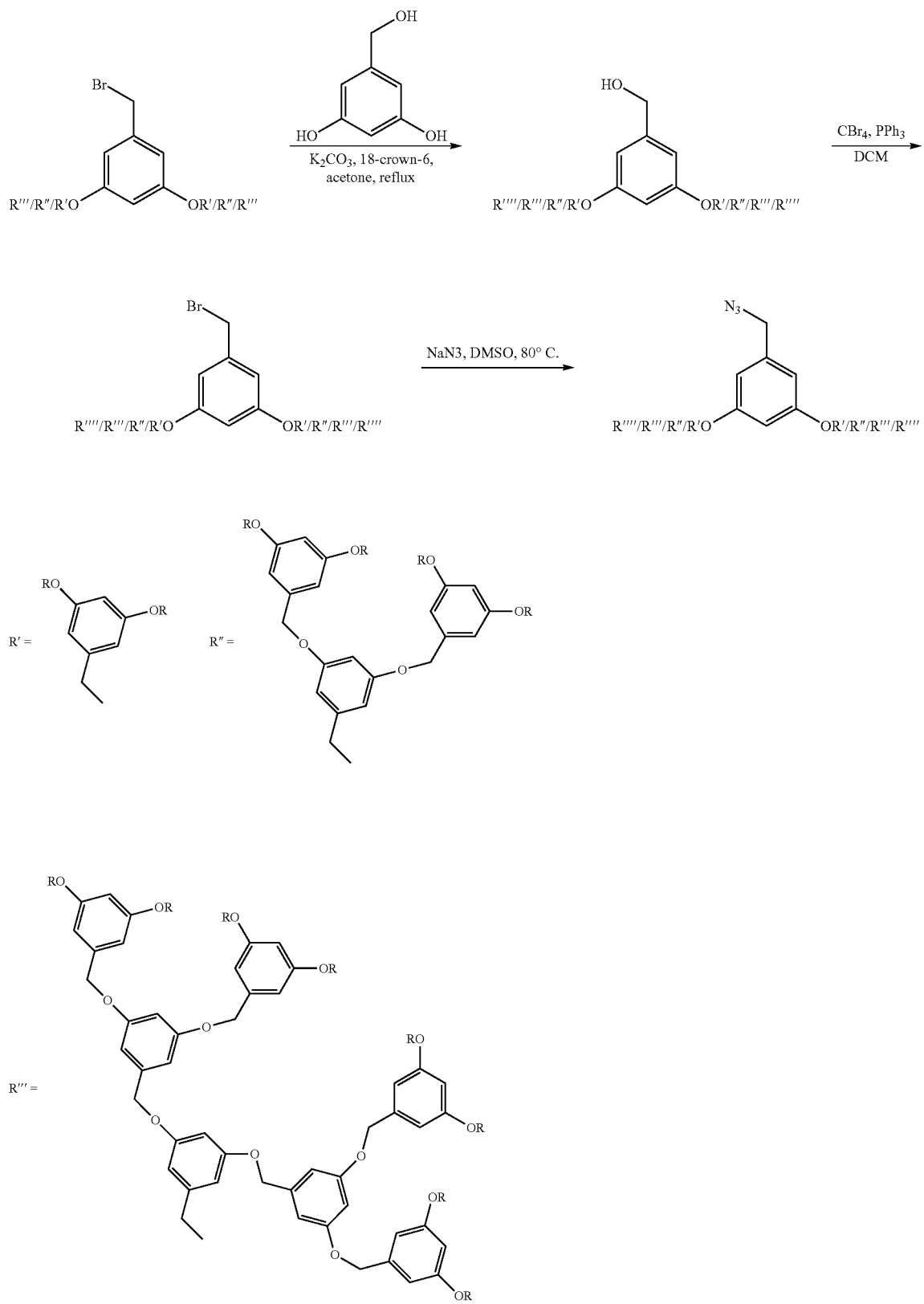

R'''' =

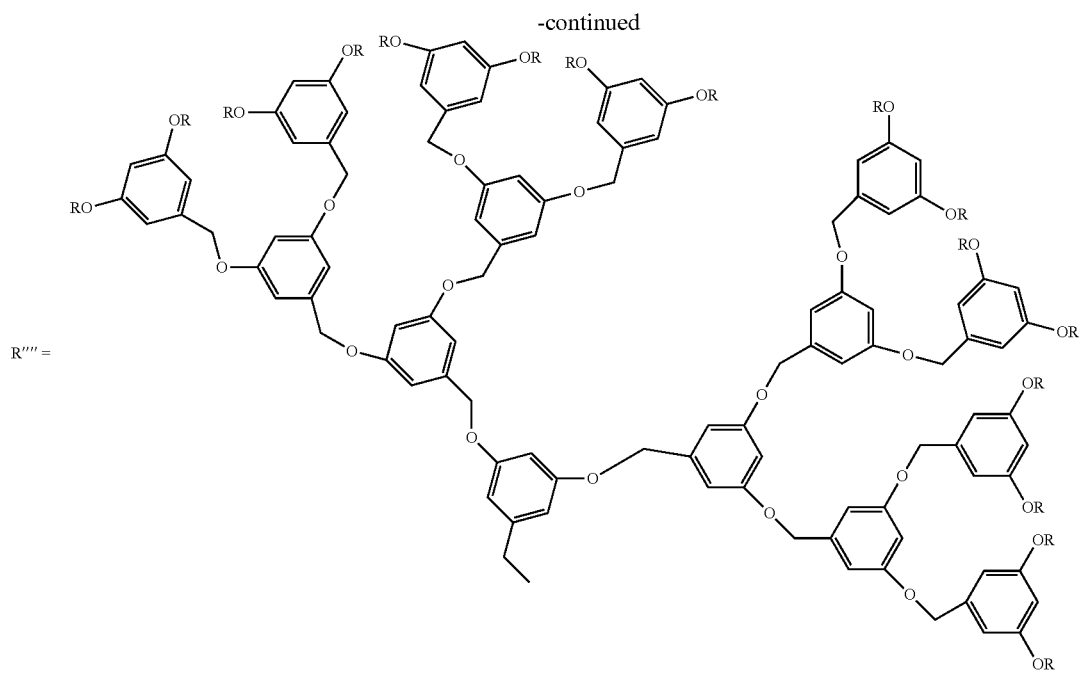

2.2.1.2. Procedures for Synthesis

General Procedure for the Synthesis of Bromide—Procedure A

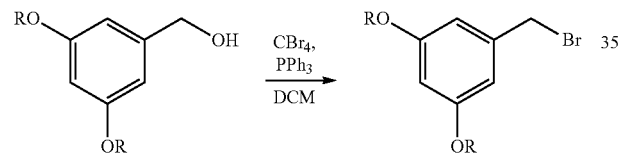

In an oven dried RBF, alcohol and tetrabromomethane were taken and dissolved in DCM. Then solution of triphenylphosphine in DCM was added drop wise at 0'C and allowed to stir for 3 hours at RT. Upon completion of reaction, DCM was evaporated under reduced pressure. Obtained residue was directly purified using silica gel column chromatography.

General Procedure for the Synthesis of G1, G2, G3, Benzyl Alcohol-Procedure B

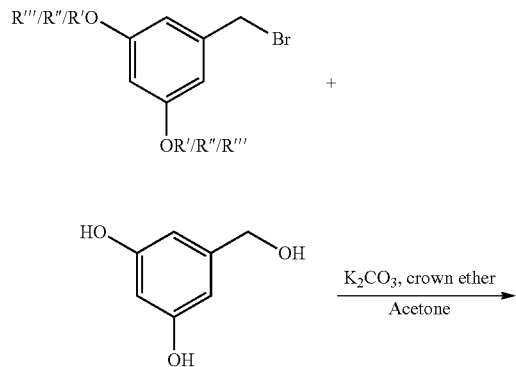

-continued

In an oven dried RBF bromide, 3,5dihydroxybenzyl alcohol, $K_2CO_3$ and crown ether were taken. The resulting mixture was refluxed for 36 hours. Upon completion, reaction mixture was cooled to RT. Then acetone was evaporated under reduced pressure. To the obtained residue water was added and extracted with DCM thrice. Combined organic layer was dried over $Na_2SO_4$ and concentrated under reduced pressure to get crude product which was purified using silica gel column chromatography.

General Procedure for the Synthesis of G1, G2, G3 Azide-Procedure C

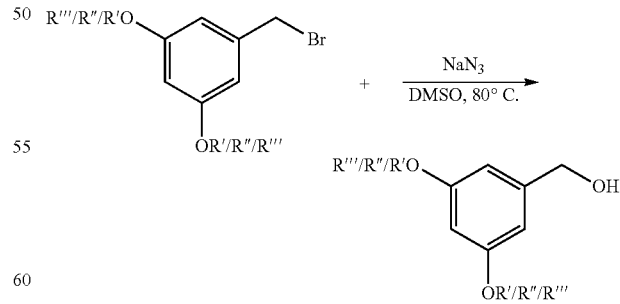

In an oven dried RBF, to the mixture of bromide and sodium azide ($NaN_3$) DMSO was added and stirred for 28 hours at 80° C. Upon completion of reaction, water was added at 0° C. to quench reaction. Resulting mixture was then extracted in DCM for thrice. Combined organic layer Synthesis of 3,5dihydroxybenzyl Alcohol

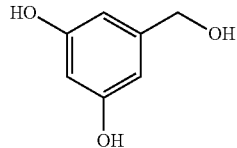

To the stirring BH$_3$-Me$_2$S (10 ml, 2M solution) and B(OMe)$_3$ in THF was slowly added a solution of 3,5-dihydroxy benzoic acid (1.5 g, 1 eq) in THF at RT. After addition, reaction was refluxed for 24 hours. Upon completion, reaction was quenched with methanol. Solvent was removed under reduced pressure. Methanol was again added to the residue and removed under reduced pressure to get crude product which was then purified using silica gel column chromatography using acetone/chloroform to afford 3,5-dihydroxybenzyl alcohol (1.02 g, 75%) as a white solid.

Synthesis of Compound 1.

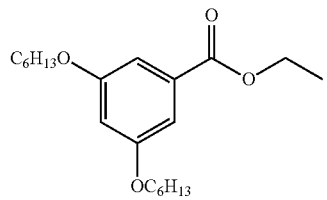

Mol. Formula: $C_{21}H_{34}O_4$
Mol. Weight: 350.25
Physical appearance: Pale yellow liquid
Yield: 96%

To the oven dried RBF ethyl 3,5-dihydroxy benzoate (5.0 g, 1 eq), K$_2$CO$_3$ (11.5 g, 4eq), 1-hexyl bromide (11.5 g, 3eq) were taken. DMF was added under stirring and heated at 75° C. C for 12 hours. Upon completion, reaction was neutralised with 1N HCl solution. Resulting solution was then extracted thrice with ethyl acetate. Combined organic layers was dried over Na$_2$SO$_4$ and concentrated under reduced pressure to get crude product which was then purified using silica gel column chromatography using ethyl acetate/hexane to afford 1a (9.0 g, 96%) as colourless liquid. R$_f$=0.46 in 5% ethyl acetate/hexane; $^1$H NMR (400 MHz, CDCl$_3$): $\delta_H$ 7.16 (d, J=2.4 Hz, 2H), 6.63 (t, J=2.4 Hz, 1H), 4.34 (q, J=7.2 Hz, 2H), 3.97 (t, J=6.8 Hz, 4H), 1.77 (quint, J=6.8 Hz, 4H), 1.49-1.31 (m, 15H), 0.90 (t, J=6.8 Hz, 6H); $^{13}$C NMR (100 MHz, CDCl$_3$): $\delta_C$ 166.67, 160.25, 132.32, 107.74, 106.41, 68.43, 61.21, 31.70, 29.29, 25.83, 22.74, 14.47, 14.18; MALDI-TOF MS: (M+K+) 389.20 ($C_{21}H_{34}O_4$+K$^+$ calculated 389.25).

Synthesis of Compound 1b

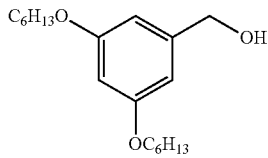

Mol. Formula: $C_{19}H_{32}O_3$
Mol. Weight: 308.24
Physical appearance: Pale yellow liquid
Yield: 85%

In an oven dried RBF, 1a(40.0 g, 1 eq) was taken and dissolved in THF with stirring at 0° C. Then lithium aluminium hydride (LAH) (19.0 g, 3eq) was added in small portions, maintaining reaction temperature 0° C. After 10 minutes, stirring was continued at RT for 2 hours. Upon completion of reaction, excess of LAH was quenched with drop wise addition of water at 0° C. Resulting mixture was stirred at RT until half white precipitate forms. Aqueous hydrochloric acid (HCl) (4N) was then added to get clear solution. Resulting content was extracted in ethyl acetate thrice. Combined organic layers was dried over Na$_2$SO$_4$ and concentrated under reduced pressure to get crude product which was purified using silica gel column chromatography to afford 1b(30.0 g, 85%) as colourless liquid. R$_f$=0.32 in 10% ethyl acetate/hexane; $^1$H NMR (400 MHz, CDCl$_3$): $\delta_H$ 6.49 (d, J=2.4 Hz, 2H), 6.38 (t, J=2.4 Hz, 1H), 4.61 (s, 2H), 3.93 (t, J=6.8 Hz, 4H), 1.76 (quint, J=6.4 Hz, 4H), 1.48-1.39 (m, 4H), 1.37-1.30 (m, 8H), 0.91 (t, J=6.8 Hz, 6H); $^{13}$CNMR (100 MHz, CDCl$_3$): $\delta_C$ 160.61, 143.34, 105.13, 100.68, 68.16, 65.52, 31.70, 29.33, 25.84, 22.74, 14.17; HRMS: (M+H$^+$) 308.24 ($C_{19}H_{32}O_3$+H$^+$ calculated 308+24).

Synthesis of Compound 1c

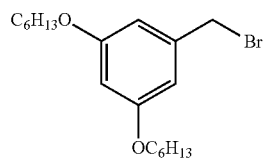

Mol. Formula: $C_{19}H_{31}BrO_2$
Mol. Weight: 370.15
Physical appearance: Pale yellow liquid
Yield: 99%

The compound 1c was synthesized using general procedure A, starting from 1b (5.0 g, 1 eq), CBr$_4$ (6.1 g, 1.2eq) and PPh$_3$ (4.8 g, 1.2eq) in DCM. The product was obtained as a colorless liquid (6.1 g, 99%) after purification by silica gel column chromatography using ethyl acetate/hexane as eluent, R$_f$=0.49 in 5% ethyl acetate/hexane; $^1$H NMR (400 MHz, CDCl$_3$): $\delta_H$ 6.52 (d, J=2 Hz, 2H), 6.38 (t, J=2 Hz, 1H), 4.41 (s, 2H), 3.92 (t, 1=6.8 Hz, 4H), 1.76 (quint, J=6.4 Hz, 4H), 1.48-1.39 (m, 4H), 1.37-1.30 (m, 8H), 0.91 (t, J=6.8 Hz, 6H); $^{13}$C NMR (100 MHz, CDCl$_3$): $\delta_C$ 160.53, 139.66, 107.43, 101.50, 68.21, 33.95, 31.70, 29.31, 25.84, 22.74, 14.18; MALDI-TOFMS (M+Na$^+$): 393.11 ($C_{19}H_{31}BrO_2$+Na$^+$ calculated 393.56).

Synthesis of Compound 2a

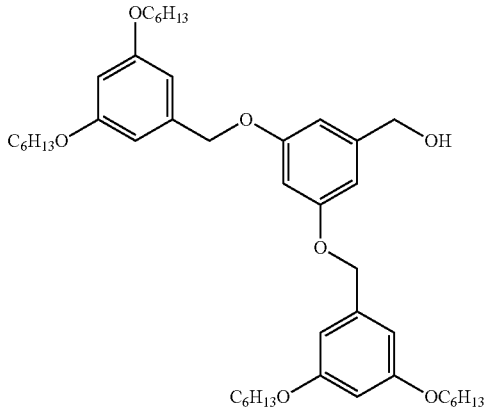

Mol. Formula: $C_{45}H_{68}O_7$
Mol. Weight: 720.50
Physical appearance: Pale yellow liquid
Yield: 90%

The compound 2a was synthesized from general procedure B, starting from 3,5-dihydroxybenzyl alcohol (2.3 g, 1 eq), Id (14.0 g, 2.1 eq), $K_2CO_3$ (5.2 g, 2.2eq), crown ether (0.70 g, 0.05eq) in acetone. The product was obtained as a yellowish liquid (10.8 g, 90%) after purification by silica gel column chromatography using ethyl acetate/hexane as eluent. $R_f$=0.2 in 5% ethyl acetate/hexane; $^1$H NMR (400 MHz, $CDCl_3$): $\delta_H$ 6.60 (d, J=2 Hz, 2H), 6.55-6.53 (m, 5H), 6.40 (t, J=2 Hz, 2H), 4.95 (s, 4H), 4.62 (s, 2H), 3.93 (t, J=6.8 Hz, 8H), 1.764 (quint, J=6.8 Hz, 8H), 1.48-1.41 (m, 8H) 1.13-1.29 (m, 16H) 0.91 (t, J=6.8 Hz, 12H); $^{13}$C NMR (100 MHz, $CDCl_3$): $\delta_C$ 160.60, 160.31, 143.52, 139.14, 105.86, 101.51, 105.89, 70.27, 68.21, 65.48, 31.72, 29.35, 25.82, 22.74, 14.44; MALDI-TOF MS (M+K$^+$): 759.36 ($C_{45}H_{68}O_7$+K$^+$ calculated 760.03).

Synthesis of Compound 2b

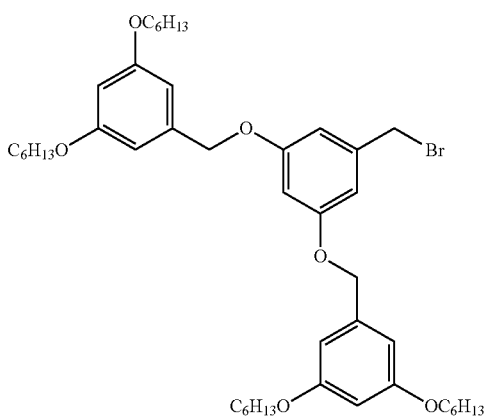

Mol. Formula: $C_{45}H_{67}BrO_6$
Mol. Weight: 782.41
Physical appearance: Pale yellow liquid
Yield: 97%

The compound 2b was synthesized from general procedure A, starting from 2a (5.0 g, 1 eq), $CBr_4$ (3.0 g, 1.2eq) and $PPh_3$ (2.3 g, 1.2eq) in DCM. The product was obtained as a colourless liquid (5.2 g, 97%) after purification by silica gel column chromatography using ethyl acetate/hexane as eluent, $R_f$=0.5 in 5% ethyl acetate/hexane; $^1$H NMR (400 MHz, $CDCl_3$): $\delta_H$ 6.60 (d, J=2 Hz, 2H), 6.55-6.53 (m, 5H), 6.40 (t, J=2 Hz, 2H), 4.95 (s, 4H), 4.40 (s, 2H), 3.93 (t, J=6.8 Hz, 8H), 1.76 (quint, J=6.8 Hz, 8H), 1.48-1.41 (m, 8H) 1.29-1.35 (m, 16H) 0.91 (t, J=6.8 Hz, 12H); $^{13}$C NMR (100 MHz, $CDCl_3$): $\delta_C$ 160.60, 160.19, 139.84, 138.91, 108.30, 105.89, 102.38, 101.05, 70.37, 68.21, 65.48, 31.72, 29.35, 25.82, 22.74, 14.44; MALDI-TOF MS (M+K$^+$): 823.58 ($C_{45}H_{68}O_6$Br+K$^+$ calculated 823.12).

Synthesis of Compound 2c

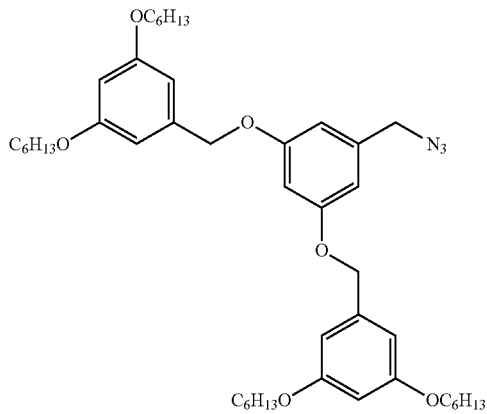

Mol. Formula: $C_{45}H_{67}N_3O_6$
Mol. Weight: 745.50
Physical appearance: Yellowish liquid
Yield: 72%

The compound 2c was synthesized from general procedure C, starting from 2b (1.0 g, 1.2 mmol), $NaN_3$ (0.46 g, 6.9 mmol) in DMSO. The product was obtained as a yellowish liquid (0.84 g, 0.94 mmol, 72%) after purification by silica gel column chromatography using ethyl acetate/hexane as eluent. $R_f$=0.32, solvent=5% ethyl acetate/hexane. $^1$H NMR (400 MHz, $CDCl_3$): $\delta_H$6.58-6.54 (m, 7H), 6.41 (t, J=2.4 Hz, 2H), 4.95 (s, 4H), 4.26 (s, 2H), 3.94 (t, J=6.8 Hz, 8H), 1.77 (quint, J=6.8 Hz, 8H), 1.49-1.24 (m, 25H), 0.91 (t, J=6.8 Hz, 12H). $^{13}$C NMR (100 MHz, $CDCl_3$): $\delta_C$ 160.64, 160.34, 138.89, 137.70, 107.26, 105.81, 101.93, 100.95, 70.30, 68.19, 60.54, 54.95, 31.71, 29.34, 25.86, 22.74, 14.33, 14.18. MALDI-ToF (M+K$^+$): 784.44.

Synthesis of Compound 3a

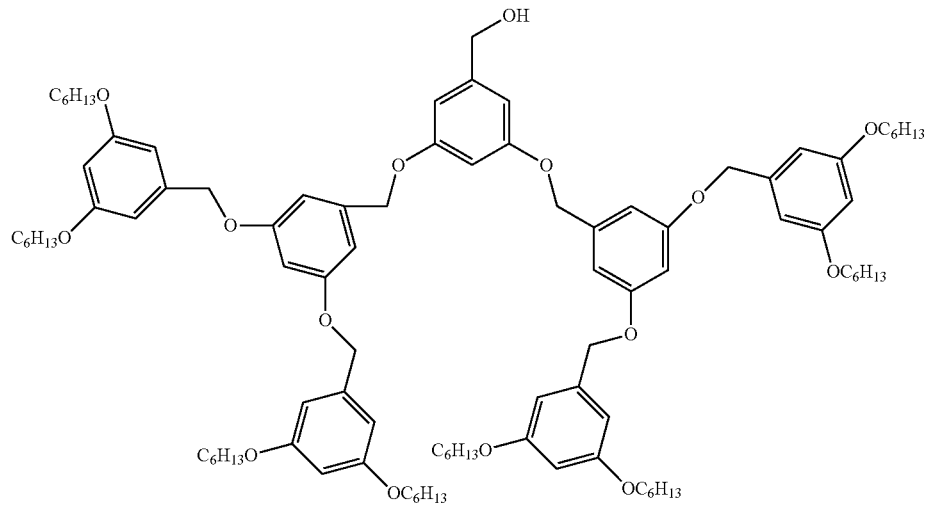

Mol. Formula: $C_{97}H_{14}O_{15}$
Mol. Weight: 1545.02
Physical appearance: Pale yellow liquid
Yield: 94%

The compound 3a was synthesized from general procedure B, starting from 3,5-dihydroxybenzyl alcohol (0.75 g, 1 eq), 2b (9.8 g, 2.1 eq), $K_2CO_3$ (1.8 g, 2.2eq), crown ether (0.22 g, 0.05eq) in acetone. The product was obtained as a yellowish liquid (8.0 g, 94%) after purification by silica gel column chromatography using ethyl acetate/hexane as eluent. $R_f$=0.4 in 25% ethyl acetate/hexane; $^1$H NMR (400 MHz, CDCl$_3$): $\delta_H$ 6.71-6.46 (m, 21H), 4.96 (s, 12H), 4.61 (s, 2H), 3.97 (t, J=6.4 Hz, 16H), 1.81 (quint, J=6.4 Hz, 16H), 1.57-1.32 (m, 48H), 0.98 (m, 24H); $^{13}$C NMR (100 MHz, CDCl$_3$): $\delta_C$ 160.61, 160.24, 160.17, 143.58, 139.31, 139.03, 106.42, 105.83, 101.67, 101.32, 100.92, 70.26, 70.08, 68.18, 65.41, 31.71, 29.34, 25.85, 22.74, 14.19; MALDI-TOF MS (M+K$^+$): 1585.01 ($C_{45}H_{68}O_7$+K$^+$ calculated 1585.17).

Synthesis of Compound 3b

Mol. Formula: $C_{97}H_{139}BrO_{14}$
Mol. Weight: 1606.93
Physical appearance: Pale yellow liquid
Yield: 92%

The compound 3b was synthesized from general procedure A, starting from 3a (7.5 g, 1 eq), CBr$_4$ (2.1 g, 1.2eq) and PPh$_3$ (1.7 g, 1.2eq) in DCM. The product was obtained as a colorless liquid (7.1 g, 92%) after purification by silica gel column chromatography using ethyl acetate/hexane as eluent, $R_f$=0.4 in 5% ethyl acetate/hexane; $^1$H NMR (400 MHz, CDCl$_3$): $\delta_H$ 6.69-6.44 (m, 21H), 4.98 (s, 12H), 4.43 (s, 2H), 3.96 (t, J=6.4 Hz, 16H), 1.78 (quint, J=6.4 Hz, 16H), 1.56-1.33 (m, 48H), 0.93 (t, J=6.8 Hz, 24H); $^{13}$C NMR (100 MHz, CDCl$_3$): $\delta_C$ 160.63, 160.27, 160.10, 139.89, 139.02, 108.24, 106.52, 105.84, 102.31, 101.78, 100.95, 77.16, 70.28, 70.19, 68.17, 31.71, 29.35, 25.85, 22.77, 14.16.; MALDI-TOF MS (M+K$^+$): 1648.02 ($C_{45}H_{68}O_6$Br+K$^+$ calculated 1648.01).

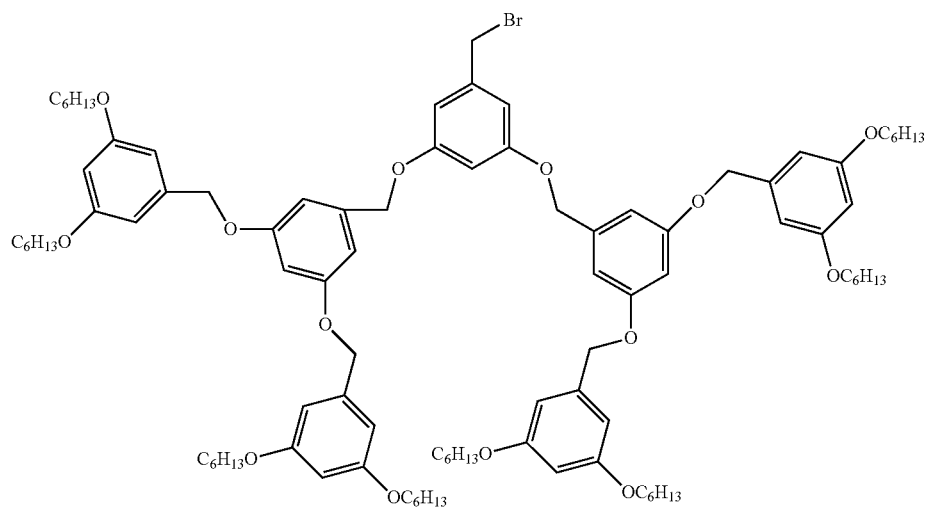

2.3.2.9. Synthesis of Compound 3c

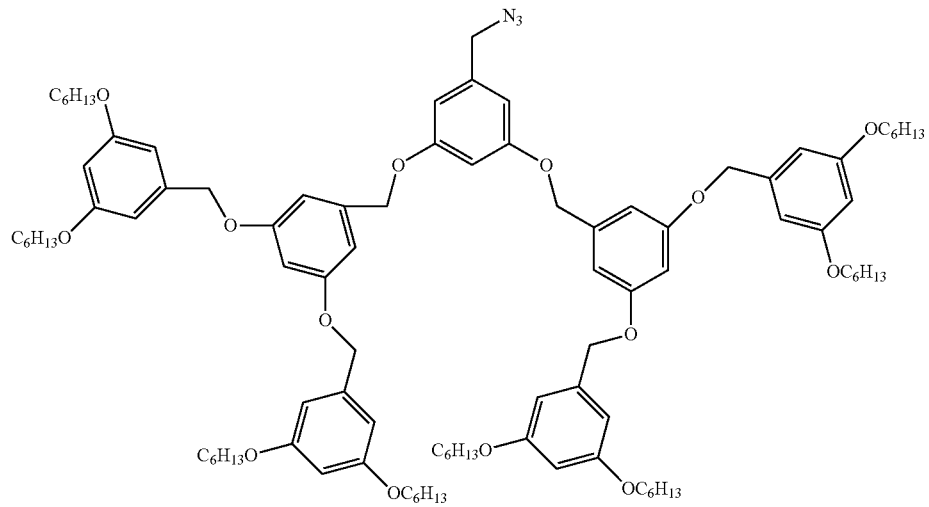

Mol. Formula: $C_{97}H_{139}N_3O_{14}$
Mol. Weight: 1571.03
Physical appearance: Pale yellow liquid
Yield: 68%

The compound 3c was synthesized from general procedure C, starting from 3b (0.80 g, 0.5 mmol), NaN₃ (0.33 g, 5.0 mmol) in DMSO. The product was obtained as a yellowish liquid (0.51 g, 0.3 mmol, 68%) after purification by silica gel column chromatography using ethyl acetate/hexane as eluent. $R_f$=0.3 in solvent=5% ethyl acetate/hexane. $^1$H NMR (400 MHz, CDCl₃): $\delta_H$ 6.69-6.42 (m, 21H), 4.99-4.96 (s, 12H), 4.28 (s, 2H), 3.94 (t, J=6.4 Hz, 16H), 1.77 (quint, J=6.4 Hz, 16H), 1.49-1.31 (m, 48H), 0.91 (t, J=6.8 Hz, 24H). $^{13}$C NMR (100 MHz, CDCl₃): $\delta_C$ 160.62, 160.28, 139.10, 139.02, 137.77, 107.31, 106.47, 105.83, 101.90, 101.81, 100.94, 77.16, 72.04, 70.26, 70.17, 68.16, 54.90, 31.70, 29.34, 25.84, 22.71, 14.15. MALDI-ToF (M+K⁺): 1610.05.

Synthesis of Compound 4a

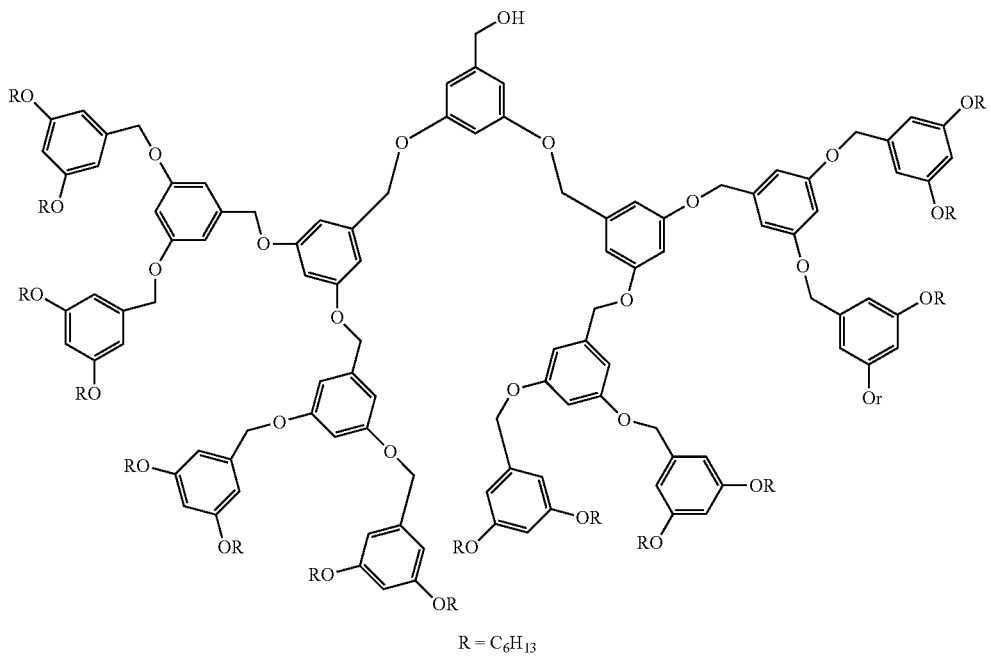

R = $C_6H_{13}$

Mol. Formula: $C_{201}H_{294}O_{31}$
Mol. Weight: 3194.06
Physical appearance: Pale yellow liquid
Yield: 89%

The compound 4a was synthesized from general procedure B, starting from 3,5-dihydroxybenzyl alcohol (0.20 g, 1eq), 3b (5.1 g, 2.1 eq), K₂CO₃ (0.48 g, 2.2eq), crown ether (0.05 g, 0.05eq) in acetone. The product was obtained as a yellowish liquid (4.1 g, 89%) after purification by silica gel column chromatography using ethyl acetate/hexane as eluent. $R_f$=0.53 in 25% ethyl acetate/hexane; $^1$H NMR (400 MHz, CDCl$_3$): $\delta_H$ 6.72-6.45 (m, 45H), 4.97 (s, 28H), 4.61 (s, 2H), 3.98 (t, J=6.4 Hz, 32H), 1.81 (quint, J=6.4 Hz, 32H), 1.53-1.31 (m, 96H), 0.97 (t, J=7.2 Hz, 48H); MALDI-TOF MS (M+K$^+$): 3235.18 (C$_{45}$H$_{68}$O$_7$+K$^+$ calculated 3235.45).

Synthesis of Compound 4b

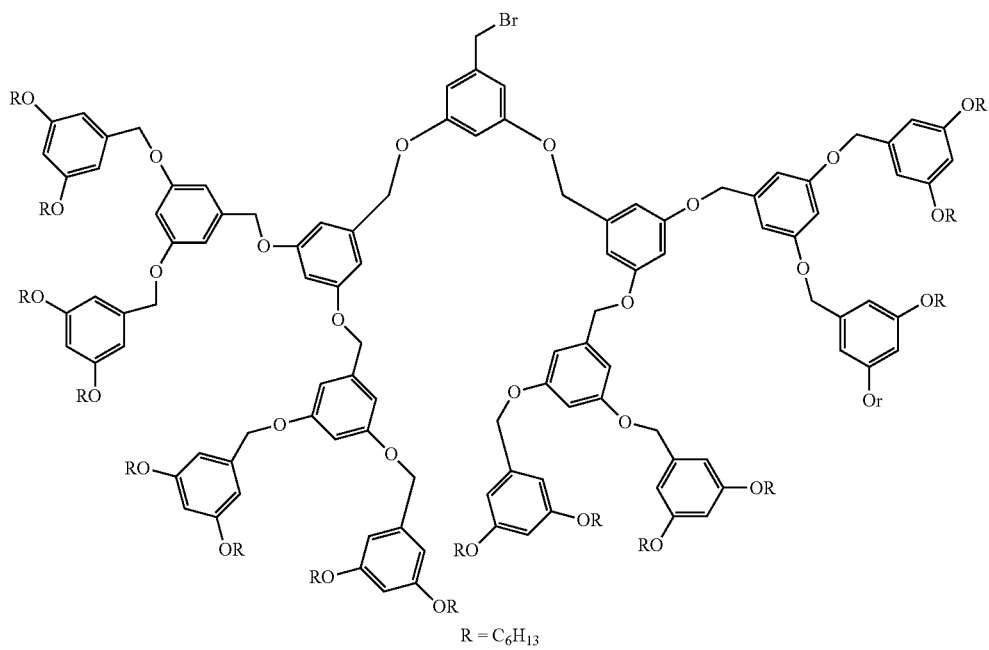

R = C$_6$H$_{13}$

Mol. Formula: C$_{201}$H$_{283}$BrO$_{30}$

Mol. Weight: 3255.98

Physical appearance: Pale yellow liquid

Yield: 74%

The compound 3b was synthesized from general procedure A, starting from 4a (4.0 g, 1 eq), CBr$_4$ (0.58 g, 1.3eq) and PPh$_3$ (0.45 g, 1.3eq) in DCM. The product was obtained as a colorless liquid (3.0 g, 74%) after purification by silica gel column chromatography using ethyl acetate/hexane as eluent, $R_f$=0.4 in 5% ethyl acetate/hexane; $^1$H NMR (400 MHz, CDCl$_3$): $\delta_H$ 6.70-6.42 (m, 45H), 4.96 (s, 28H), 4.41 (s, 2H), 3.94 (t, J-6.4 Hz, 32H), 1.77 (quint, J-6.4 Hz, 32H), 1.53-1.29 (m, 99H), 0.92 (t, J=7.2 Hz, 48H); $^{13}$C NMR (100 MHz, CDCl$_3$): $\delta_C$ 160.54, 160.18, 160.13, 160.00, 139.20, 139.14, 138.99, 106.40, 105.73, 101.63, 100.84, 77.16, 70.14, 70.04, 68.05, 31.66, 29.29, 25.80, 22.67, 14.11; MALDI-TOF MS (M+K$^+$): 3298.08 (C$_{45}$H$_{68}$O$_6$Br+K$^+$ calculated 3298.3).

Synthesis of Compound 4c

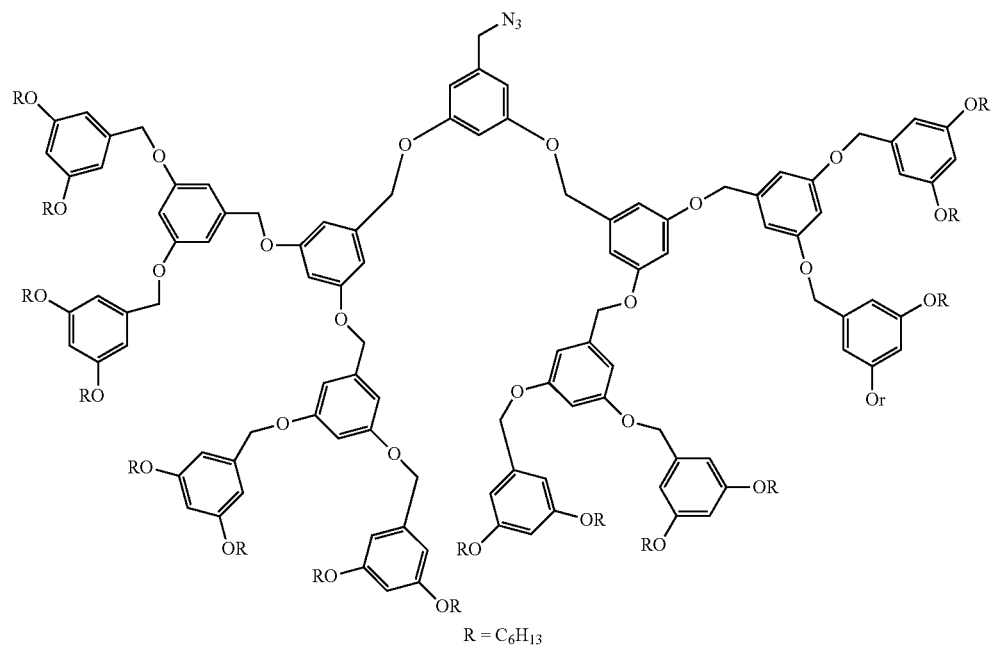

R = C$_6$H$_{13}$

Mol. Formula: C$_{201}$H$_{283}$N$_3$O$_{30}$

Mol. Weight: 3219.07

Physical appearance: Pale yellow liquid

Yield: 74%

The compound 4c was synthesized from general procedure C, starting from 4b (4.0 g, 1 eq), (1.0 g, 0.3 mmol), NaN3 (0.2 g, 3.0 mmol) in DMSO. The product was obtained as a yellowish liquid (0.58 g, 0.2 mmol, 74%) after purification by silica gel column chromatography using ethyl acetate/hexane as eluent, Rf=0.3 in 5% ethyl acetate/hexane. $^1$H NMR (400 MHz, CDCl$_3$): $\delta_H$ 6.74-6.48 (m, 45H), 4.98 (s, 28H), 4.26 (s, 2H), 3.98 (t, J=6.4 Hz, 32H), 1.91-1.79 (m, J=6.4 Hz, 32H), 1.53-1.41 (m, 99H), 0.99 (t, J=7.2 Hz, 48H). 13C NMR (100 MHz, CDCl$_3$): $\delta_C$ 160.58, 160.22, 139.20, 139.01, 107.36, 106.45, 105.78, 101.67, 100.89, 77.16, 70.20, 70.11, 68.10, 31.68, 29.32, 25.82, 22.69, 14.13. MALDI-ToF (M+Na+): 3244.12.

Synthesis of Compound 5a

Synthesis of Compound 5b

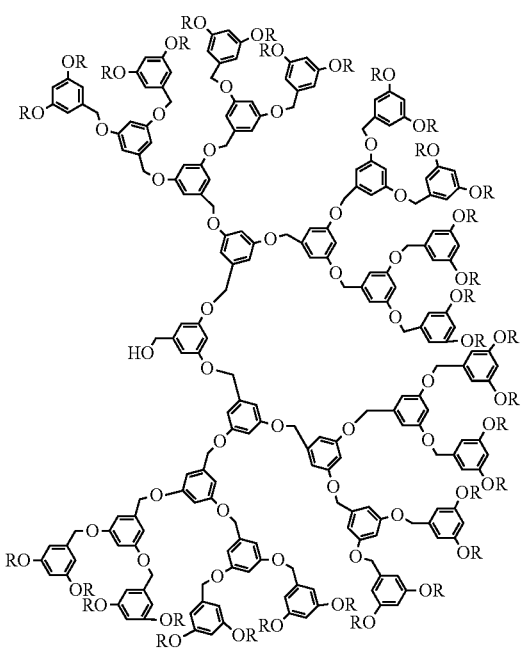

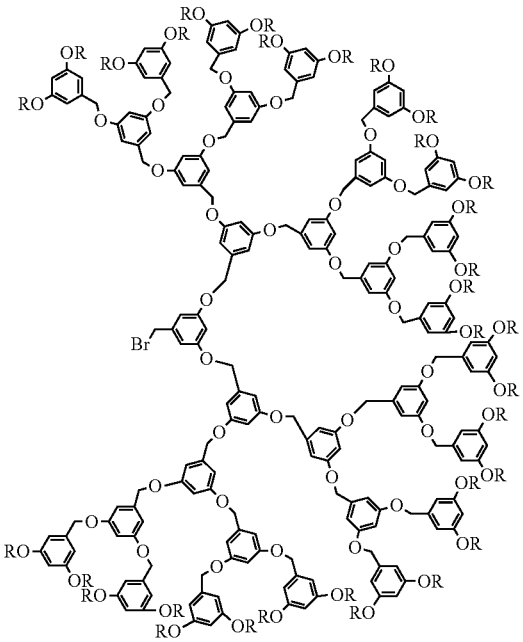

The compound 5a was synthesized from general procedure B, starting from 3,5-dihydroxybenzyl alcohol (0.20 g, 1 eq), 3b (5.1 g, 2.1 eq), $K_2CO_3$ (0.48 g, 2.2eq), crown ether (0.05 g, 0.05eq) in acetone. The product was obtained as a yellowish liquid (4.1 g, 89%) after purification by silica gel column chromatography using ethyl acetate/hexane as eluent. $R_f$=0.53 in 25% ethyl acetate/hexane; $^1$H NMR (400 MHz, $CDCl_3$): $δ_H$ 6.66-6.38 (m, 84H), 5.00-4.96 (3, 53H), 4.54 (s, 2H), 3.89 (t, J=6.4 Hz, 60H), 1.77 (quint, J=6.4 Hz, 58H), 1.50-1.26 (m, 194H), 0.88 (t, J=7.2 Hz, 95H); $^{13}$C NMR (100 MHz, $CDCl_3$): $δ_C$ 160.62, 160.27, 139.22, 139.05, 106.56, 105.86, 100.95, 77.16, 70.25, 68.17, 31.72, 29.35, 25.86, 22.73, 14.18. MALDI-TOF MS (M+K$^+$): 3235.18 ($C_{45}H_{68}O_7$+K$^+$ calculated 3235.45).

The compound 5b was synthesized from general procedure A, starting from 5a (4.0 g, 1 eq), $CBr_4$ (0.58 g, 1.3eq) and $PPh_3$ (0.45 g, 1.3eq) in DCM. The product was obtained as a colorless liquid (3.0 g, 74%) after purification by silica gel column chromatography using ethyl acetate/hexane as eluent, $R_f$=0.4 in 5% ethyl acetate/hexane; $^1$H NMR (400 MHz, $CDCl_3$): $δ_H$ 6.70-6.41 (m, 84H), 4.96-4.94 (m, 52H), 4.38 (s, 2H), 3.93 (t, J-6.4 Hz, 60H), 1.75 (quint, J-6.4 Hz, 58H), 1.45-1.34 (m, 185H), 0.92 (t, J=7.2 Hz, 94H); $^{13}$C NMR (100 MHz, $CDCl_3$): de 160.59, 160.23, 139.20, 139.02, 106.52, 105.82, 101.70, 100.91, 77.16, 70.22, 70.15, 68.13, 31.70, 29.34, 25.84, 22.72, 14.16; MALDI-TOF MS (M+K$^+$): 3298.08 ($C_{45}H_{68}O_6Br$+K$^+$ calculated 3298.3).

Synthesis of Compound 5c

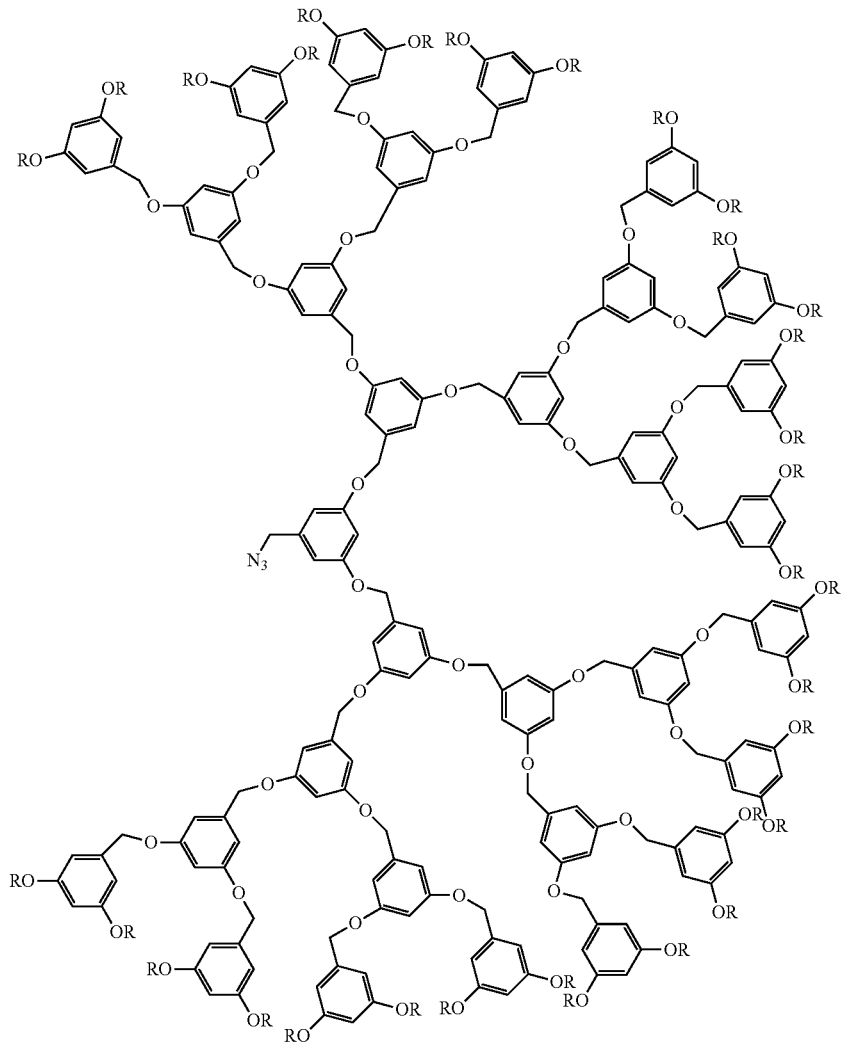

The compound 5c was synthesized from general procedure C, starting from 5b (4.0 g, 1 eq), (0.8 g, 0.1 mmol) and NaN3 (0.15 g, 2.2 mmol) in DMSO. The product was obtained as a yellowish liquid (0.7 g, 0.1 mmol, 90%) after purification by silica gel column chromatography using ethyl acetate/hexane as eluent, Rf=0.3 in solvent=5% ethyl acetate/hexane; $^1$HNMR (400 MHz, CDCl$_3$): δH 6.68-6.38 (m, 84H), 5.04-4.73 (m, 50H), 4.14 (s, 2H), 3.93 (t, J=6.4 Hz, 60H), 1.73 (quint, J=6.4 Hz, 64H), 1.42-1.25 (m, 185H), 0.89 (t, J=7.2 Hz, 110H). $^{13}$C NMR (100 MHz, CDCl$_3$): δC 160.60, 160.25, 139.03, 106.57, 105.84, 100.91, 77.16, 70.77, 70.23, 68.15, 31.72, 29.84, 29.35, 25.86, 22.74, 14.19. MALDI-ToF MS (M+K$^+$): 6537.02.

2.4. Procedure for Synthesis of AABPs

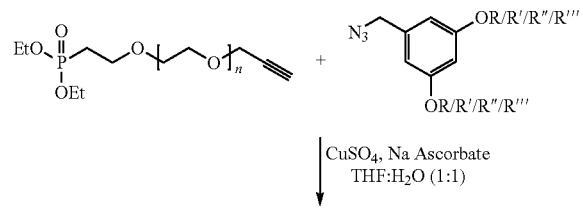

CuSO$_4$, Na Ascorbate
THF:H$_2$O (1:1)

-continued

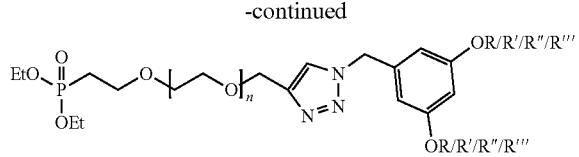

Oxalyl Chloride
DCM

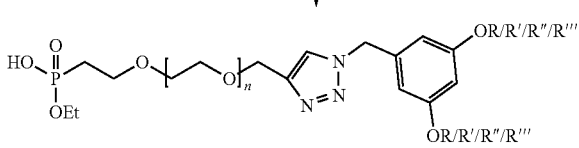

DAST
DCM

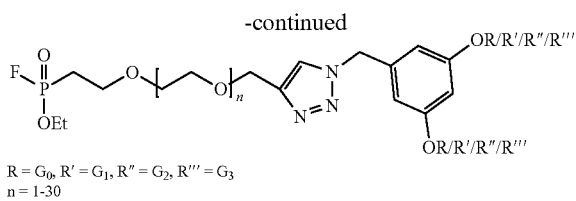

R = G₀, R' = G₁, R" = G₂, R'" = G₃
n = 1-30

Scheme 7. Synthesis of MAABPs.

All the AABPs were synthesised by [2+3] dipolar cycloaddition (click reaction) of the hydrophilic alkynes (diphosphonate esters) with hydrophobic azides in the presence of sodium ascorbate and copper sulphate (CuSO$_4$) in THF/water (1:1) unless mentioned. Then the resulting product was deprotected in the presence of oxalyl chloride in DCM to get monophosphonate ester and finally fluorinated using diethylaminosulfur triflouride (DAST) in DCM. The detailed procedure is mentioned below.

2.4.1. General Procedure for Click Reaction—Procedure D

Hydrophobic azide (1 eq) and hydrophilic alkyne (1 eq) were dissolved in degassed THF and stirred until clear solution was obtained, then degassed water was added and stirred vigorously for 10 more minutes unless mentioned. Freshly prepared 1M sodium ascorbate (0.05 eq) and 1M CuSO$_4$ (0.1 eq) were added to the reaction mixture at least thrice in an intervals of 45 minutes and allowed to react for 16 hours at RT. Upon completion, reaction mixture was extracted in dichloromethane (DCM) and combined organic layer was dried over Na$_2$SO$_4$ and concentrated under reduced pressure to get crude product which was purified using reverse phase chromatography using acetonitrile (ACN)/H$_2$O system first (to remove unreacted diphosphonate ester) and CHC$_3$ later (to elute click product) followed by normal phase chromatography using methanol (MeOH)/DCM solvent system.

Note:

MALDI-TOF MS analysis of 2.4.1 showed presence of unreacted diphosphonate ester and click product. Surprisingly both the components were at the same R$_f$ in normal phase TLC with different solvent systems. However, huge R$_f$ difference was observed in reverse phase TLC with 30% ACN/H$_2$O. Hence, their separation was achieved using reverse phase chromatography. MALDI-TOF MS analysis of purified fractions showed the complete absence of unreacted diphosphonate ester.

2.4.2. General Procedure for Deprotection—Procedure E

Diphosphonate ester (1 eq) was dissolved in DCM with stirring. Then oxalyl chloride (4 eq) was added dropwise at RT and allowed to react for 18 hours under stirring. Upon completion, excess of oxalyl chloride and DCM were removed under vacuum. Then water was added to the residue and stirred for 5 minutes. The resulting mixture was extracted thrice with DCM, combined organic layer was dried over Na$_2$SO$_4$ and concentrated under vacuum to get crude product which was used for next step without further purification.

2.4.3. General procedure for fluorination—Procedure F

To the stirring solution of monophosphonate ester (1 eq) in DCM, DAST (4 eq) was added dropwise at RT and allowed to react for 4 hours. Excess of DAST and DCM were evaporated under reduced pressure. To the obtained residue, water was added and stirred for 2 more minutes to quench any residual DAST. Reaction mixture was then extracted thrice with DCM. Combined organic layer was dried over Na$_2$SO$_4$ and concentrated under vacuum to get crude product. These final AABPs were used for protein modification without further purification.

Synthesis of compound 6a

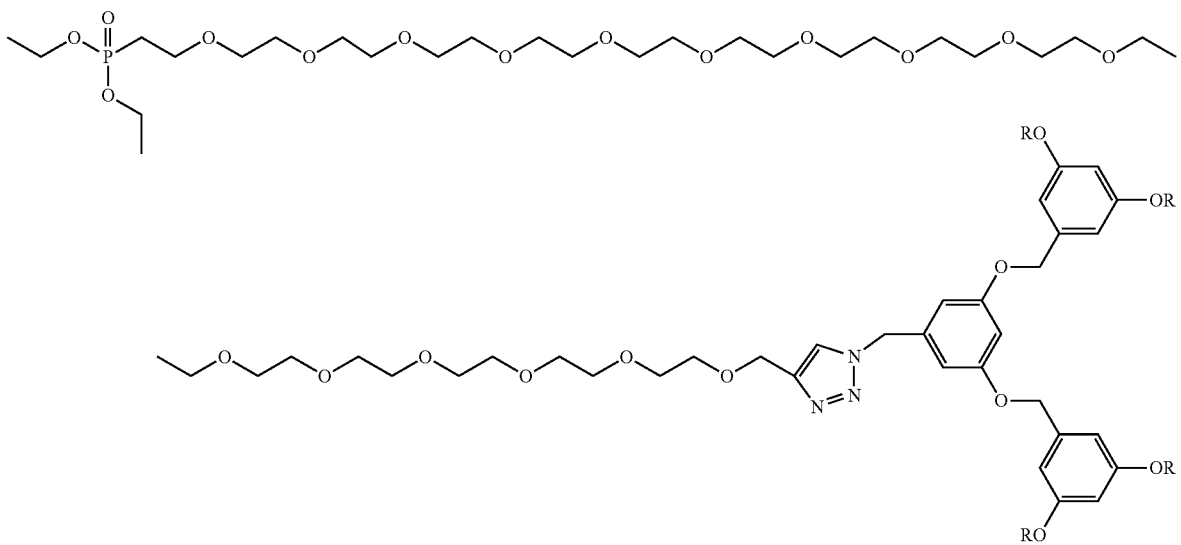

Mol. Formula: $C_{84}H_{144}N_3O_{25}P$
Mol. Weight: 1625.98
Physical appearance: pale yellow liquid
Yield: 60%

The compound 6a was prepared by general procedure D, starting from 2C (0.300 g, 0.18 mmol), alkyne (0.162 g, 0.18 mmol), CuSO$_4$ (1.4 mg, 0.009 mmol), sodium ascorbate (2.3 mg, 0.012 mmol). The product was obtained as a pale yellow liquid (0.26 g, 0.01 mmol, 60%) after purification by reverse phase silica gel column chromatography followed by normal phase silica gel column chromatography using MeOH/DCM as eluent, R$_f$=0.4 in 5% MeOH/DCM. $^1$H NMR (400 MHz, CDCl$_3$): $\delta_H$ 7.53 (s, 1H), 6.64-6.36 (m, 9H), 5.01-4.84 (m, 4H), 4.13-4.00 (4H), 3.92 (t, J=6.4 Hz, 8H), 3.73-3.48 (m, 33H), 2.17-2.08 (m, 2H), 1.78-1.68 (m, 17H), 1.51-1.18 (m, 24H), 0.89 (m, 26H).

Synthesis of compound 6b

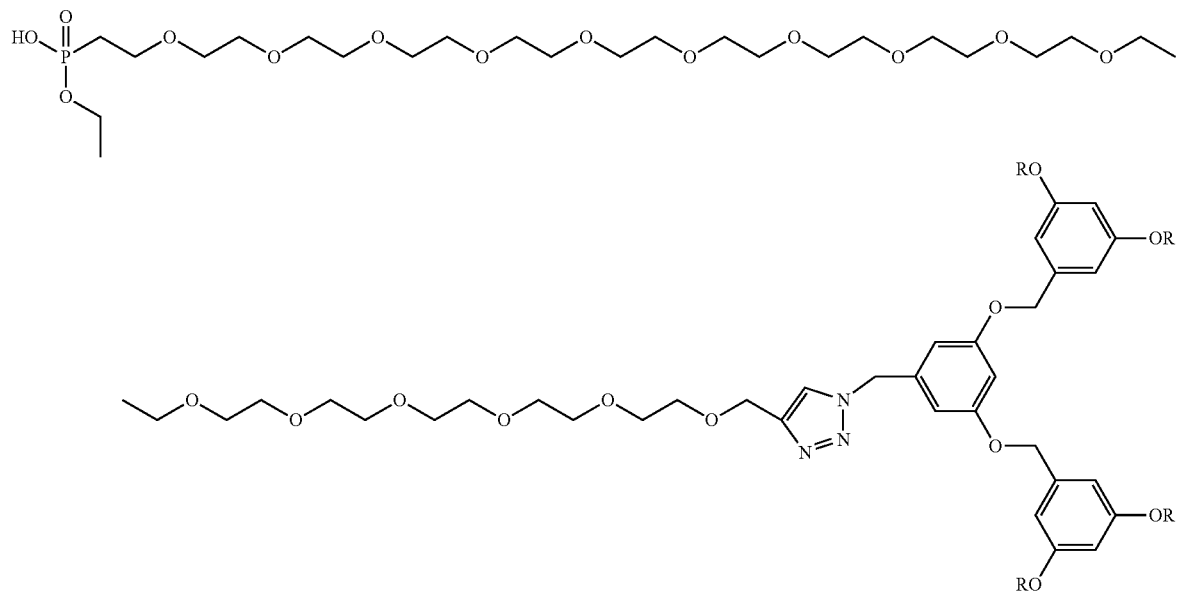

Mol. Formula: $C_{82}H_{140}N_3O_{25}P$
Mol. Weight: 1597.98
Physical appearance: pale yellow liquid
The compound 6b was prepared by general procedure E, starting from 6a (0.2 g, 0.21 mmol) and oxalyl chloride (0.1 g, 0.8 mmol) The product was obtained as a pale yellow liquid which was used further without purification MALDI-TOF (M+K$^+$): 1620.31.

Synthesis of compound 6c

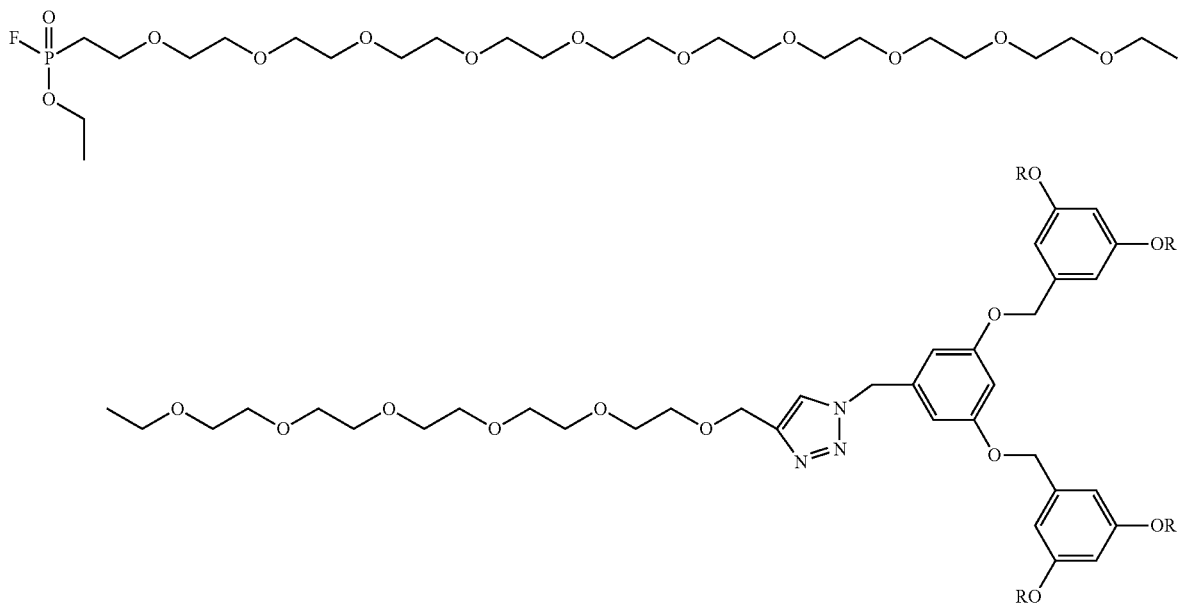

Mol. Formula: $C_{82}H_{139}FN_3O_{24}P$
Mol. Weight: 1599.95.12
Physical appearance: pale yellow liquid
The compound 6c was prepared by general procedure F, starting from 6b (0.2 g, 0.21 mmol) and DAST (0.1 g, 0.8 mmol). $^{19}$F NMR (400 MHz, CDCl$_3$): $\delta_F$ –59.91, –62.74.

Synthesis of compound 7a

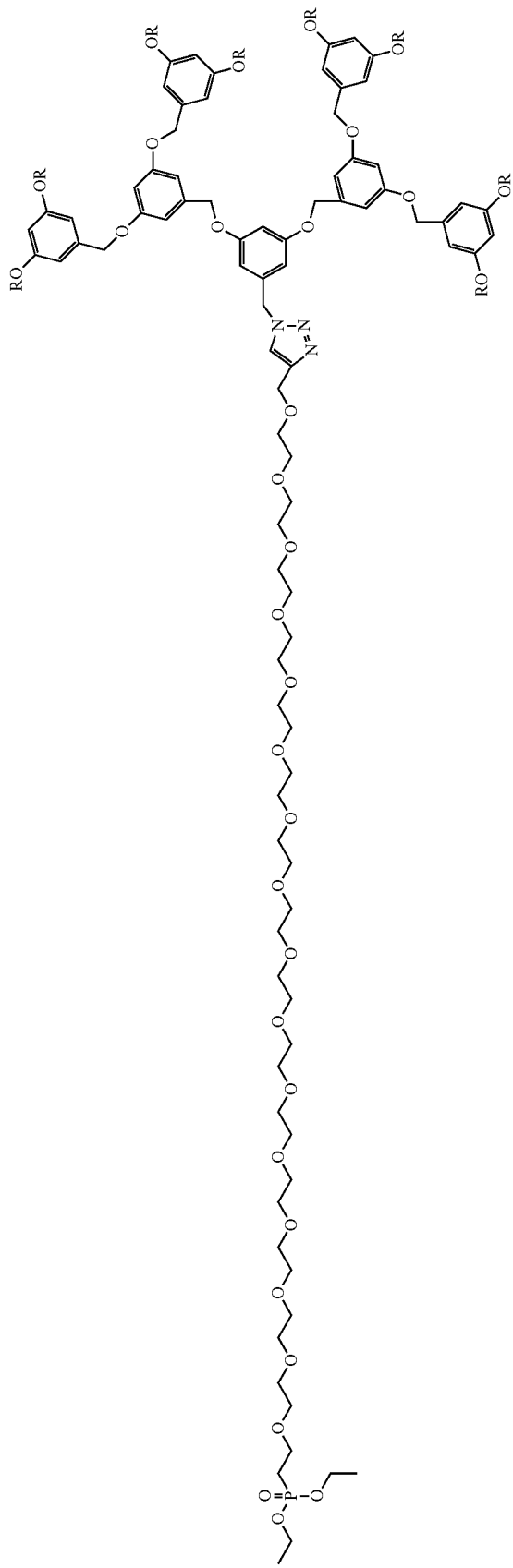

Mol. Formula: $C_{136}H_{216}N_3O_{33}P$
Mol. Weight: 2452.14
Physical appearance: pale yellow liquid
Yield: 60%

The compound 7a was prepared by general procedure D, starting from 3C (0.300 g, 0.18 mmol), alkyne (0.162 g, 0.18 mmol), $CuSO_4$ (1.4 mg, 0.009 mmol), sodium ascorbate (2.3 mg, 0.012 mmol). The product was obtained as a pale yellow liquid (0.26 g, 0.01 mmol, 60%) after purification by reverse phase silica gel column chromatography followed by normal phase silica gel column chromatography using MeOH/DCM as eluent, $R_f$=0.4 in 5% MeOH/DCM. $^1$H NMR (400 MHz, $CDCl_3$): $\delta_H$ 7.53 (s, 1H), 6.64-6.36 (m, 21H), 5.01-4.84 (m, 12H), 4.13-4.00 (4H), 3.92 (t, J=6.4 Hz, 16H), 3.73-3.48 (m, 55H), 2.17-2.08 (m, 2H), 1.78-1.68 (m, 17H), 1.51-1.18 (m, 60H), 0.89 (m, 26H). MALDI-TOF (M+K$^+$): 2491.13

Synthesis of Compound 7b

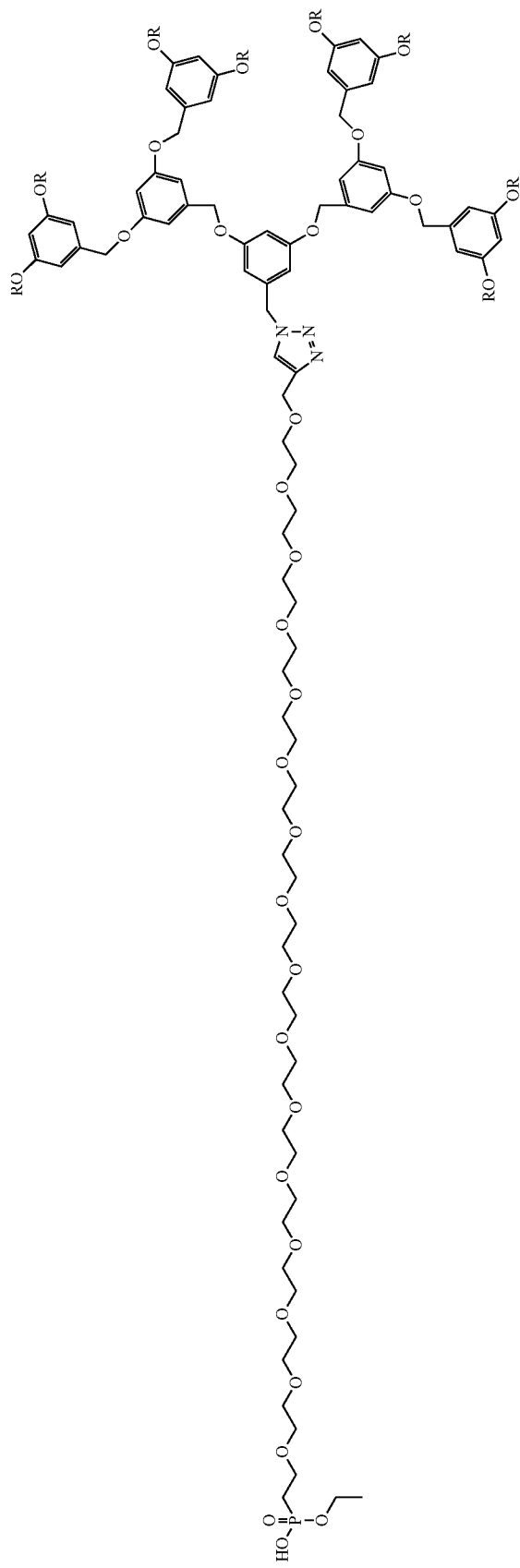

Mol. Formula: $C_{134}H_{212}N_3O_{33}P$
Mol. Weight: 2424.23
Physical appearance: pale yellow liquid The compound 7b was prepared by general procedure E, starting from 7a (0.2 g, 0.21 mmol) and oxalyl chloride (0.1 g, 0.8 mmol) The product was obtained as a pale yellow liquid which was used further without purification $^1$H NMR (400 MHz, CDCl$_3$): $\delta_H$ 7.53 (s, 1H), 6.64-6.36 (m, 21H), 5.01-4.84 (m, 12H), 4.13-4.00 (2H), 3.92 (t, J=6.4 Hz, 16H), 3.73-3.48 (m, 55H), 2.17-2.08 (m, 2H), 1.78-1.68 (m, 17H), 1.51-1.18 (m, 60H), 0.89 (m, 26H). MALDI-TOF (M+K$^+$): 2465.11

Synthesis of compound 7c

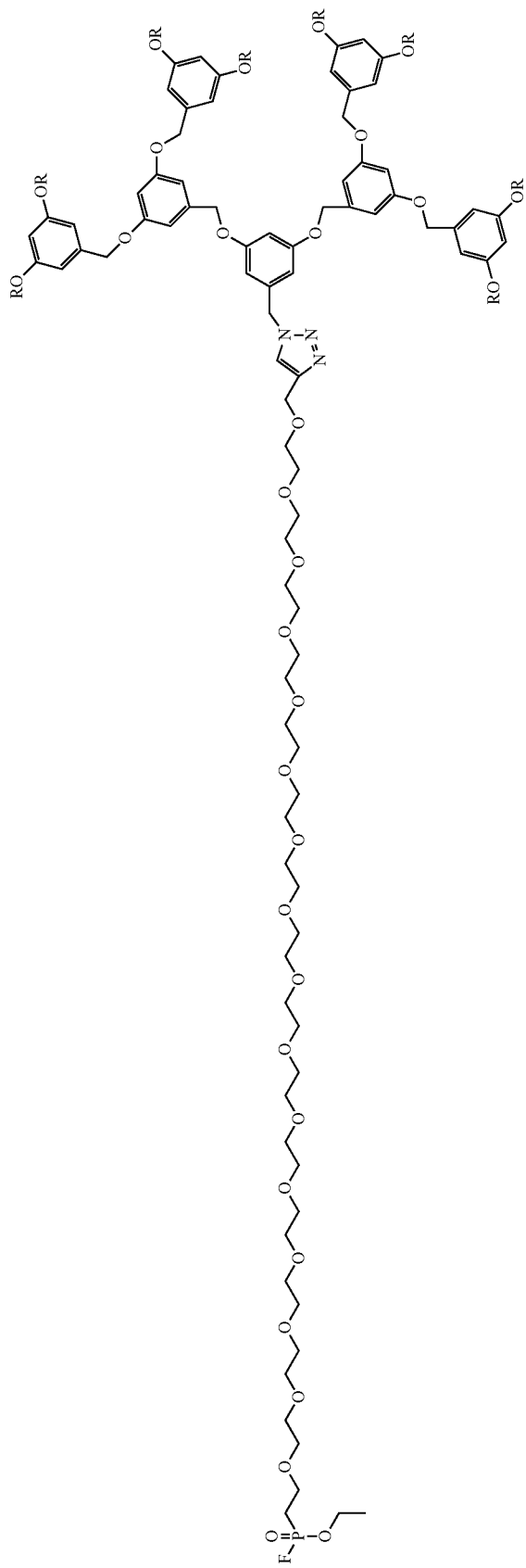

Mol. Formula: $C_{134}H_{211}FN_3O_{32}P$
Mol. Weight: 2426.12
Physical appearance: pale yellow liquid
The compound 7c was prepared by general procedure F, starting from 7b (0.2 g, 0.21 mmol) and DAST (0.1 g, 0.8 mmol). $^{19}F$ NMR (400 MHz, $CDCl_3$): $\delta_F$ −59.91, −62.74 . . . . MALDI-TOF ($M+K^+$): 2467.73

Synthesis of Compound 8a

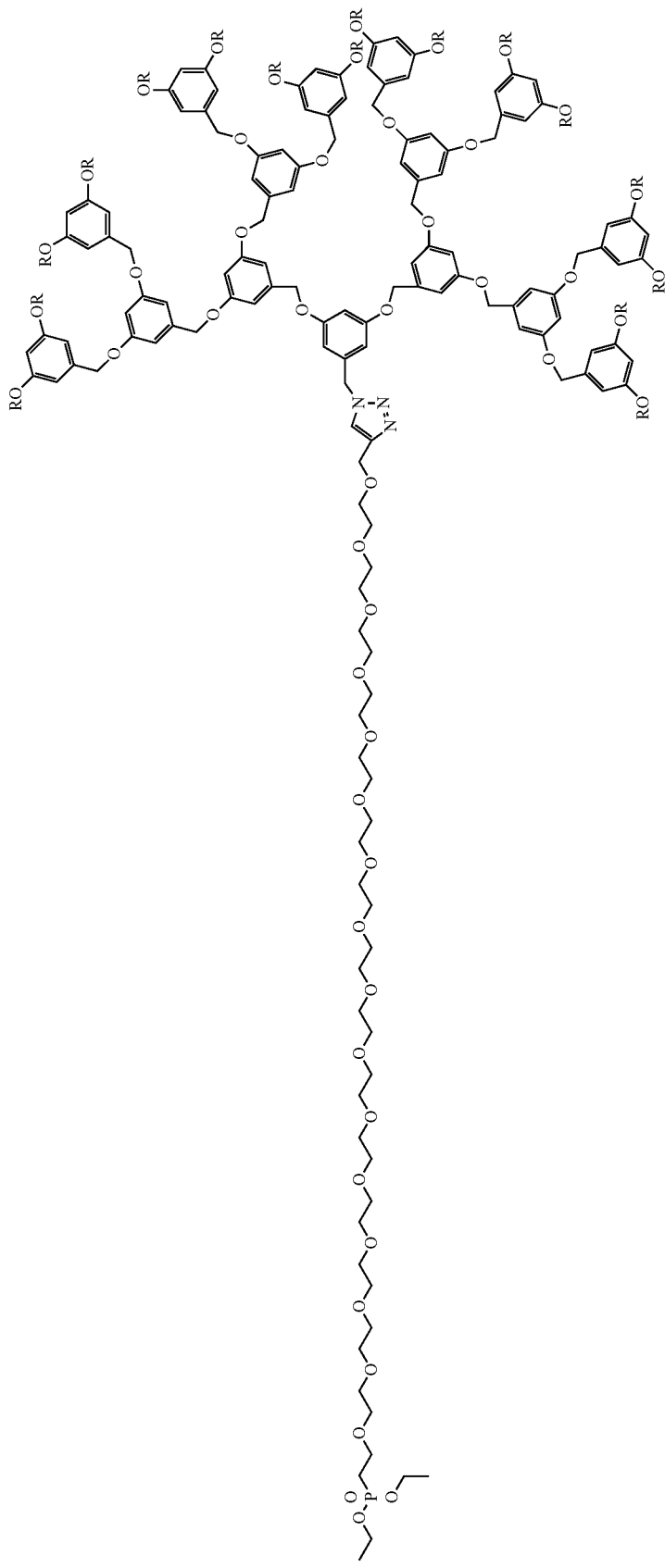

Mol. Formula: $C_{240}H_{360}N_3O_{49}P$
Mol. Weight: 4102.47
Physical appearance: pale yellow liquid
Yield: 66%

The compound 8a was prepared by general procedure D, starting from 4C (1 g, 0.3 mmol), alkyne (0.300 g, 0.3 mmol), $CuSO_4$ (2.6 mg, 0.016 mmol), sodium ascorbate (4.8 mg, 0.02 mmol). The product was obtained as a pale yellow liquid (0.9 g, 0.2 mmol, 66%) after purification by reverse phase silica gel column chromatography followed by normal phase silica gel column chromatography using MeOH/DCM as eluent, $R_f$=0.4 in 5% MeOH/DCM.; $^1$H NMR (400 MHz, $CDCl_3$): $\delta_H$ 7.50 (s, 11H), 6.74-6.34 (m, 45H), 5.27 (s, 14H), 5.00-4.84 (m, 26H), 4.16-4.03 (m, 4H), 3.91 (t, J=6.4H, 32H), 3.71-3.54 (m, 67H), 2.13-2.05 (m, 2H), 1.78-1.67 (m, 32H), 1.49-1.23 (m, 110H), 0.89 (t, J=6.4H, 52H). MALDI-TOF (M+K$^+$): 4129.21

Synthesis of Compound 8b

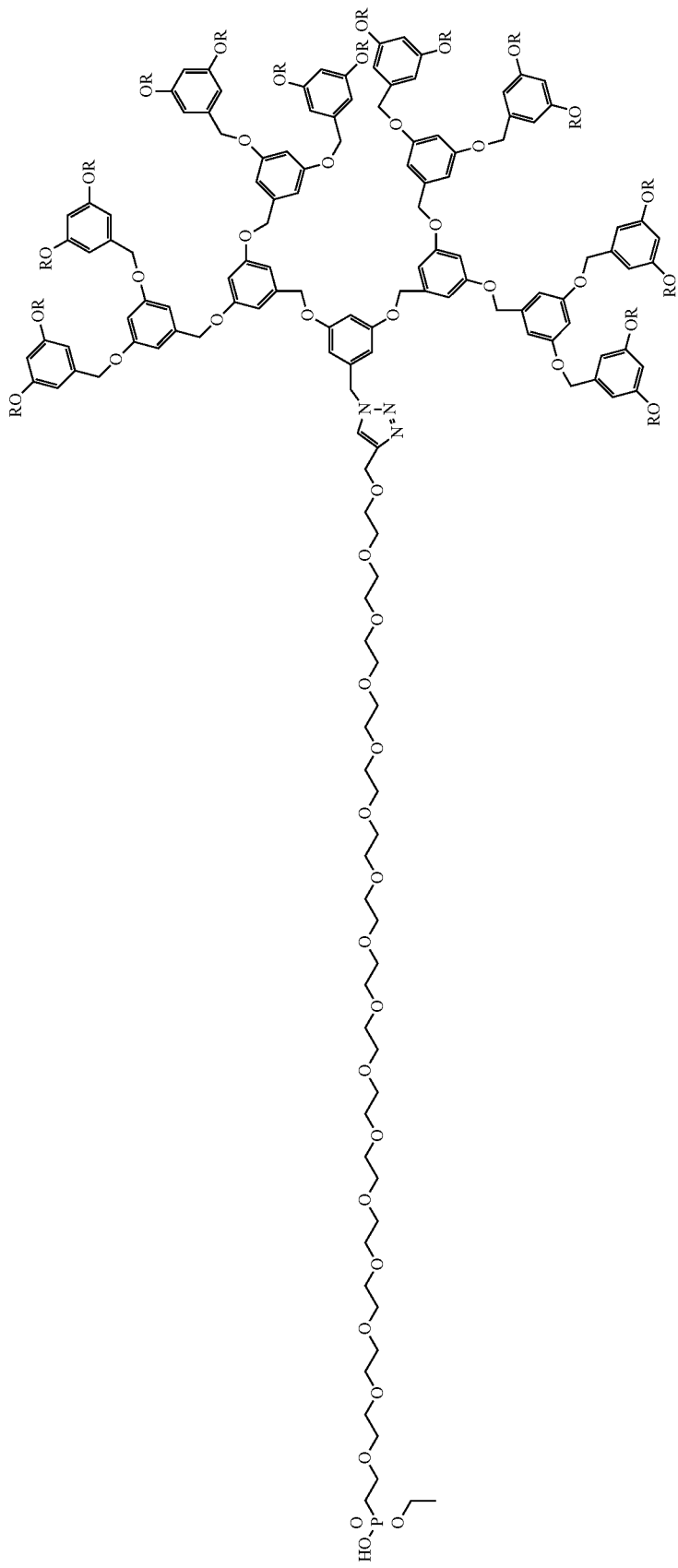

Mol. Formula: $C_{240}H_{360}N_3O_{49}P$
Mol. Weight: 4102.47
Physical appearance: pale yellow liquid The compound 8b was prepared by general procedure E, starting from 8a (0.186 g, 0.21 mmol), oxalyl chloride (0.1 g, 0.84 mmol); $^1$H NMR (400 MHz, CDCl$_3$): $\delta_H$ 7.50 (s, 1H), 6.74-6.34 (m, 45H), 5.27 (s, 14H), 5.00-4.84 (m, 26H), 4.16-4.03 (m, 4H), 3.91 (t, J=6.4H, 32H), 3.71-3.54 (m, 67H), 2.13-2.05 (m, 2H), 1.78-1.67 (m, 32H), 1.49-1.23 (m, 110H), 0.89 (t, J-6.4H, 52H). MALDI-TOF (M+K$^+$): 4132.03.

Synthesis of compound 8c

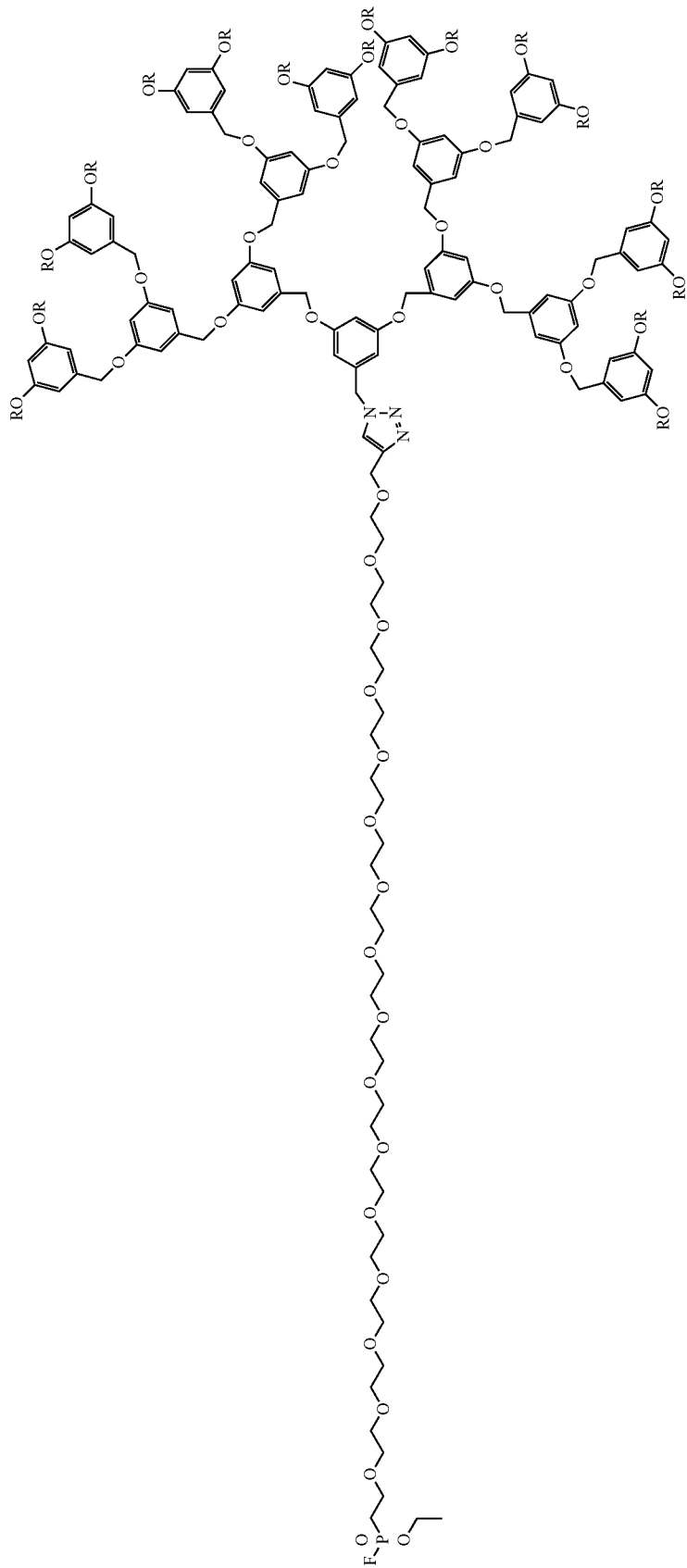

Mol. Formula: $C_{238}H_{355}FN_3O_{48}P$
Mol. Weight: 4076.40
Physical appearance: pale yellow liquid
The compound 8c was prepared by general procedure E, starting from 8b (0.186 g, 0.21 mmol), DAST (0.1 g, 0.84 mmol); $^{19}F$ NMR (400 MHz, $CDCl_3$): $\delta_F$ −59.91, −62.74.

Synthesis of Compound 9a

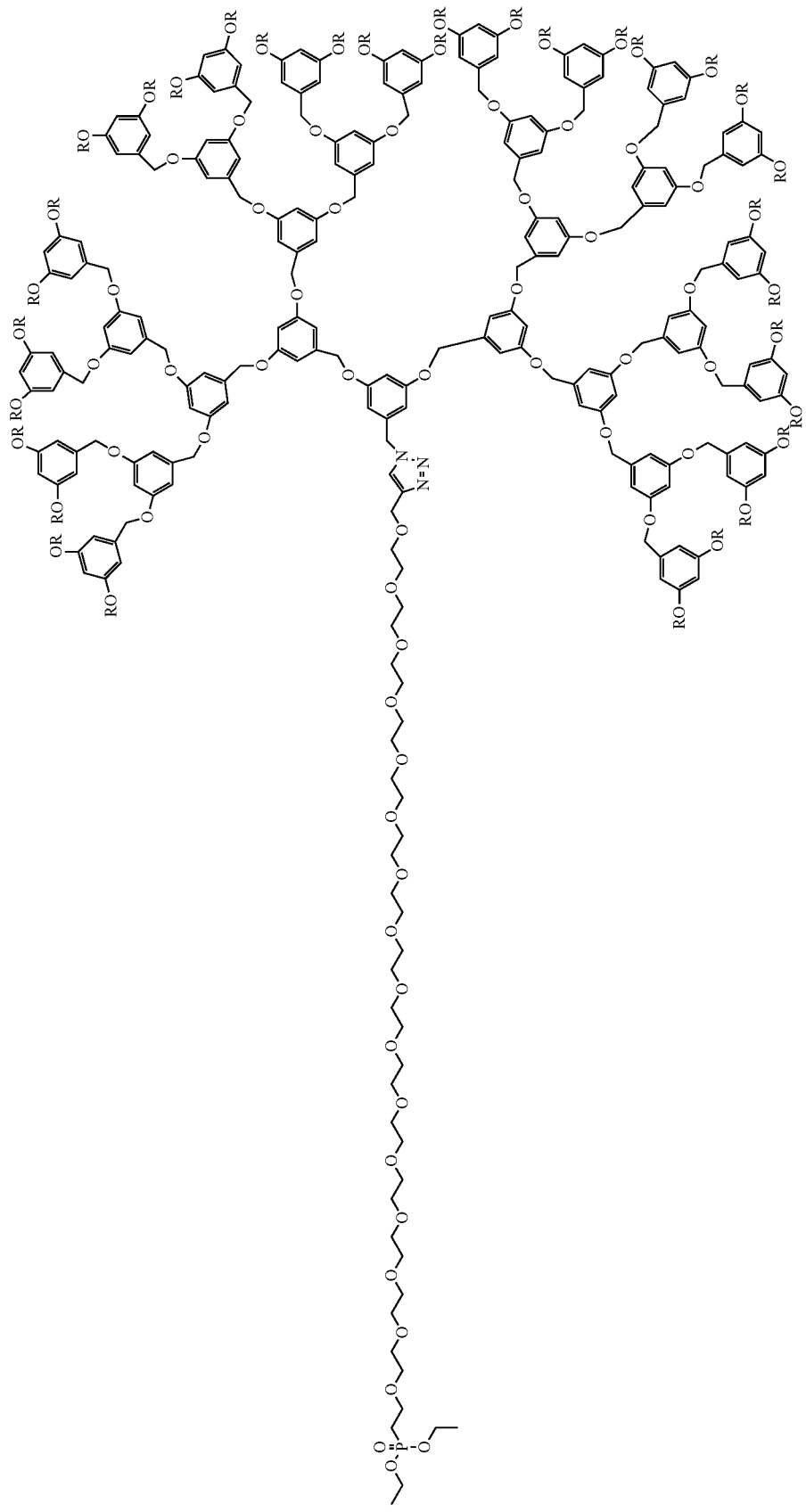

Mol. Formula: $C_{449}H_{650}N_3O_{80}P$
Mol. Weight: 7401.05
Physical appearance: pale yellow liquid
Yield: 59%

The compound 9a was prepared by general procedure D starting from 5C (0.2 g, 0.031 mmol), alkyne (0.027 g, 0.31 mmol), $CUSO_4$ (0.2 mg, 0.001 mmol), sodium ascorbate (0.4 mg, 0.002 mmol). The product was obtained as a pale yellow liquid (0.1 g, 0.02 mmol, 59%) after purification by reverse phase silica gel column chromatography followed by normal phase silica gel column chromatography using MeOH/DCM as eluent, $R_f$=0.4 in 5% MeOH/DCM. $^1$H NMR (400 MHz, $CDCl_3$): $\delta$17.48 (s, 1H), 6.74-6.33 (m, 93H), 5.38 (s, 2H), 5.02-4.83 (m, 57H), 4.20-4.06 (m, 4H), 3.95-3.81 (m, 64H), 3.76-3.46 (m, 63H), 2.18-2.07 (m, 3H), 1.80-1.65 (m, 66H), 1.45-1.27 (m, 273H) 0.98-0.76 (m, 114H). MALDI-TOF ($M+K^+$): 7433.37

Synthesis of compound 9b

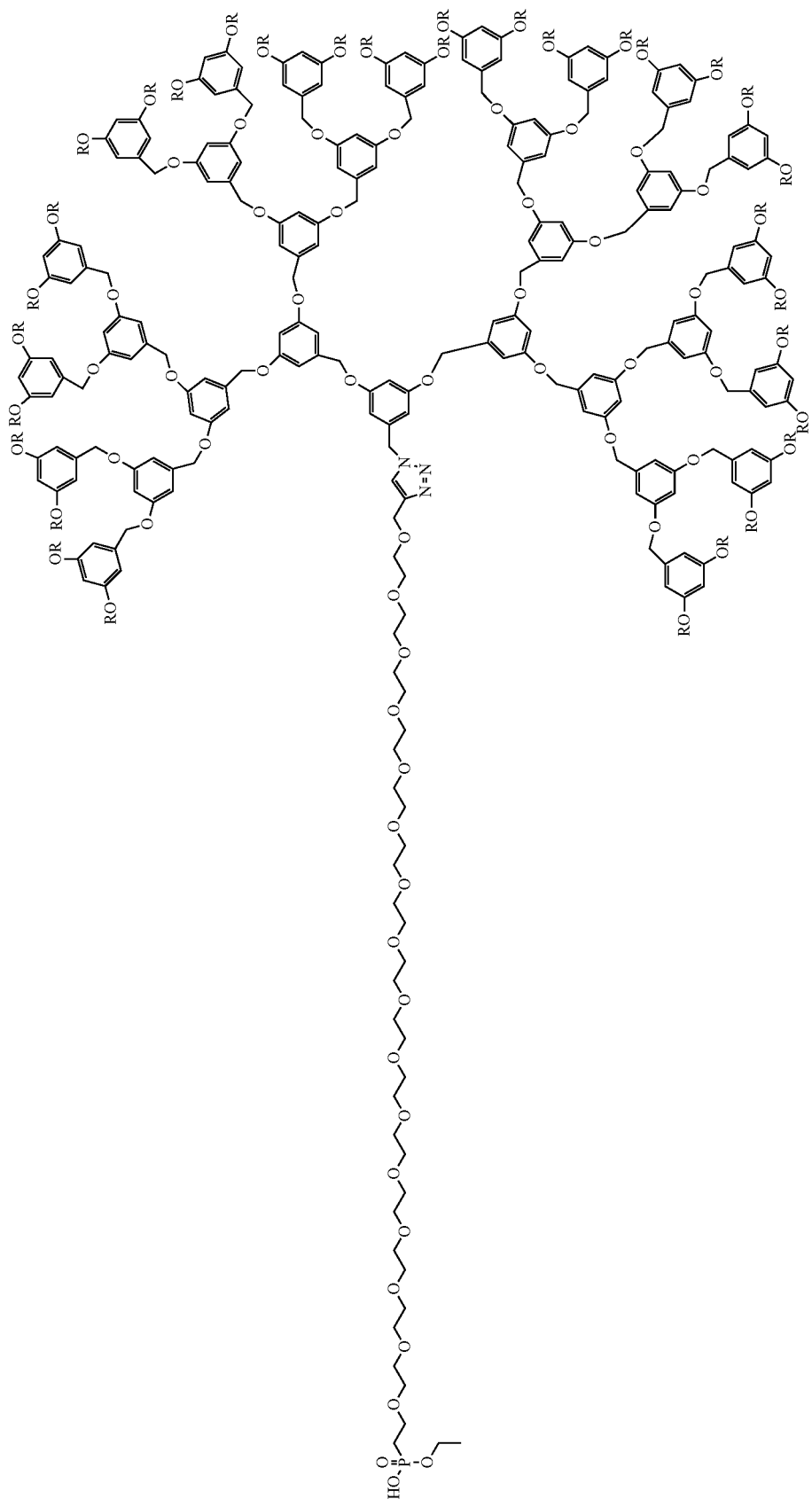

Mol. Formula: $C_{449}H_{650}N_3O_{80}P$
Mol. Weight: 7401.05
Physical appearance: pale yellow liquid
Yield: 59%

The compound 9b was prepared by general procedure E, starting from 9a (0.186 g, 0.21 mmol), oxalyl chloride (0.1 g, 0.84 mmol); $^1$H NMR (400 MHz, CDCl$_3$): δ7.48 (s, 1H), 6.74-6.33 (m, 93H), 5.38 (s, 2H), 5.02-4.83 (m, 57H), 4.20-4.06 (m, 2H), 3.95-3.81 (m, 64H), 3.76-3.46 (m, 63H), 2.18-2.07 (m, 3H), 1.80-1.65 (m, 66H), 1.45-1.27 (m, 273H) 0.98-0.76 (m, 114H). MALDI-TOF (M+K$^+$): 7431.37

Synthesis of Compound 9c

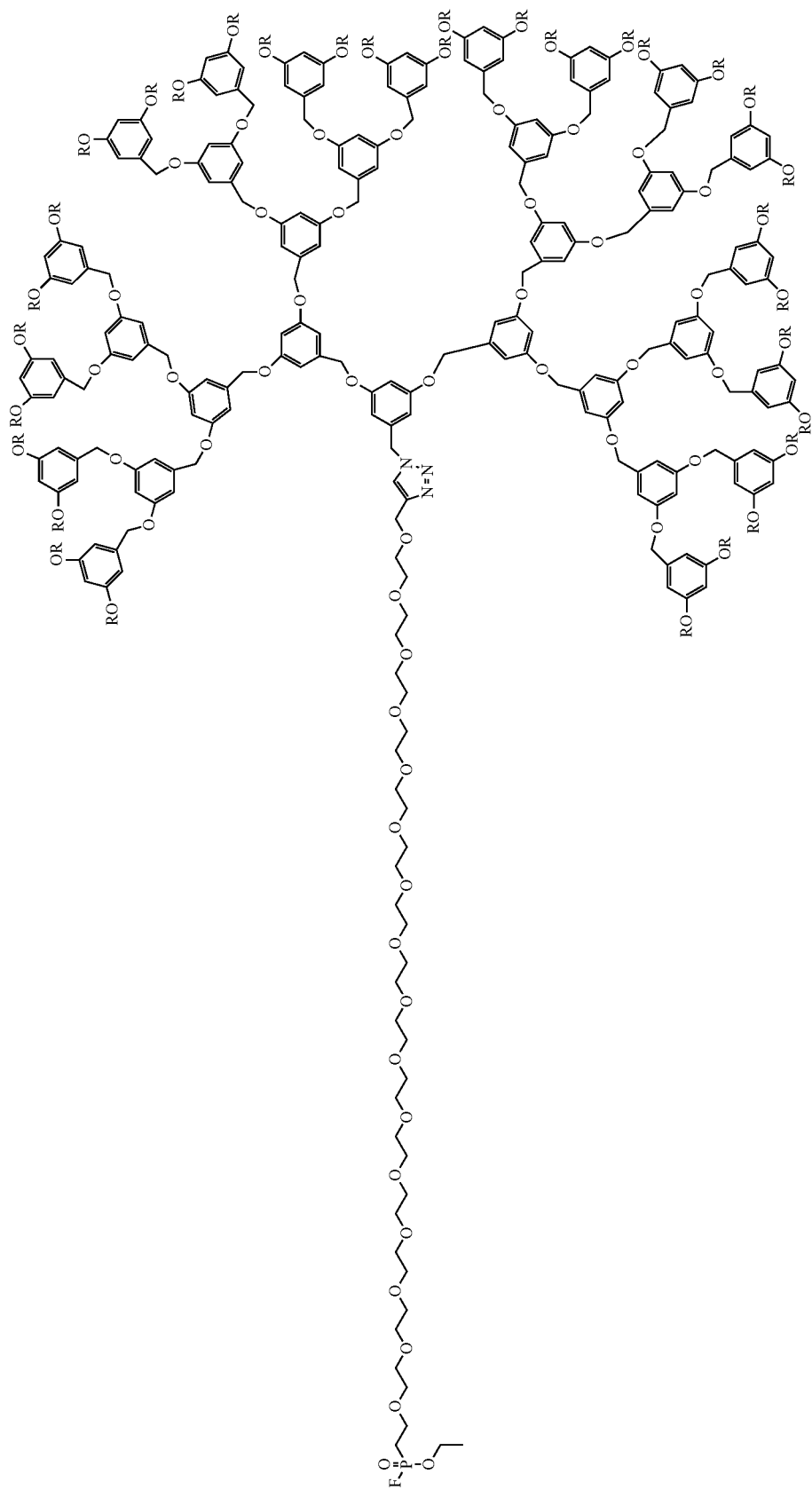

Mol. Formula: $C_{447}H_{645}FN_3O_{79}P$
Mol. Weight: 7401.05
Physical appearance: pale yellow liquid
The compound 9c was prepared by general procedure F starting from 9b (0.186 g, 0.21 mmol), DAST (0.1 g, 0.84 mmol); $^{19}F$ NMR (400 MHz, $CDCl_3$): $\delta_F$ −59.91, −62.74.

3.1. Synthesis of Dendrimer Variants Protein-Dendron Conjugates 3.1.1. Synthesis and Purification of Chy-CEG-G1 Protein Conjugates (Scheme 8)

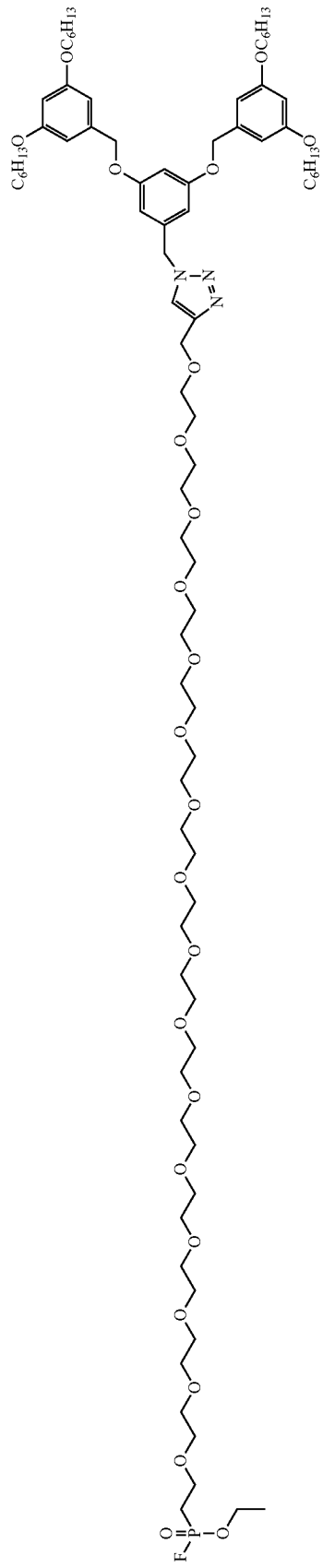
FP-CEG-G1
Chymotrypsin | 50 mM Sodium phosphate pH 7.4, Triton X-100 →
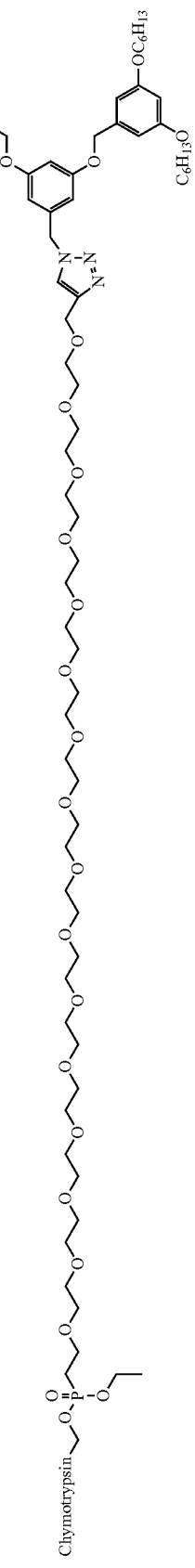
Chy-CEG-G1

The Chy-CEG-G1 protein conjugates were synthesized and purified by the general procedure described in 1A to IC.

3.1.2. Synthesis and Purification of Chy-CEG-G2 Protein Conjugates (Scheme 9)

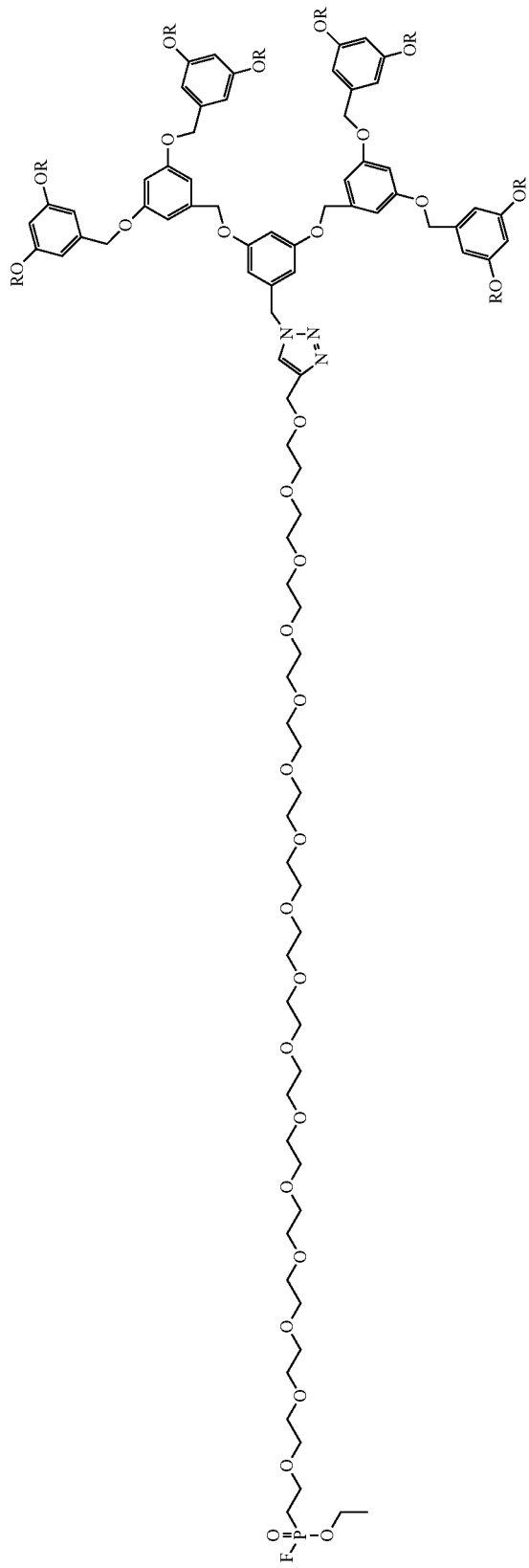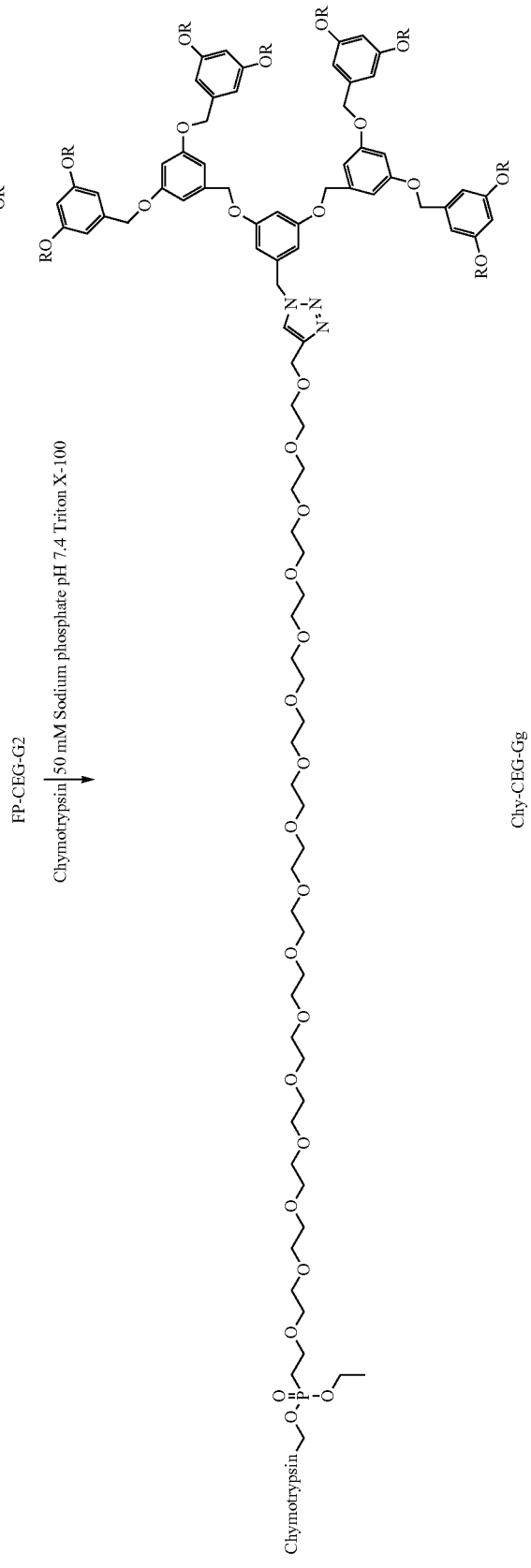

The Chy-CEG-G2 protein conjugates were synthesized and purified by the general procedure described in 1A to IC.

3.1.3. Synthesis and Purification of Chy-CEG-G3 Protein Conjugates (Scheme 10)

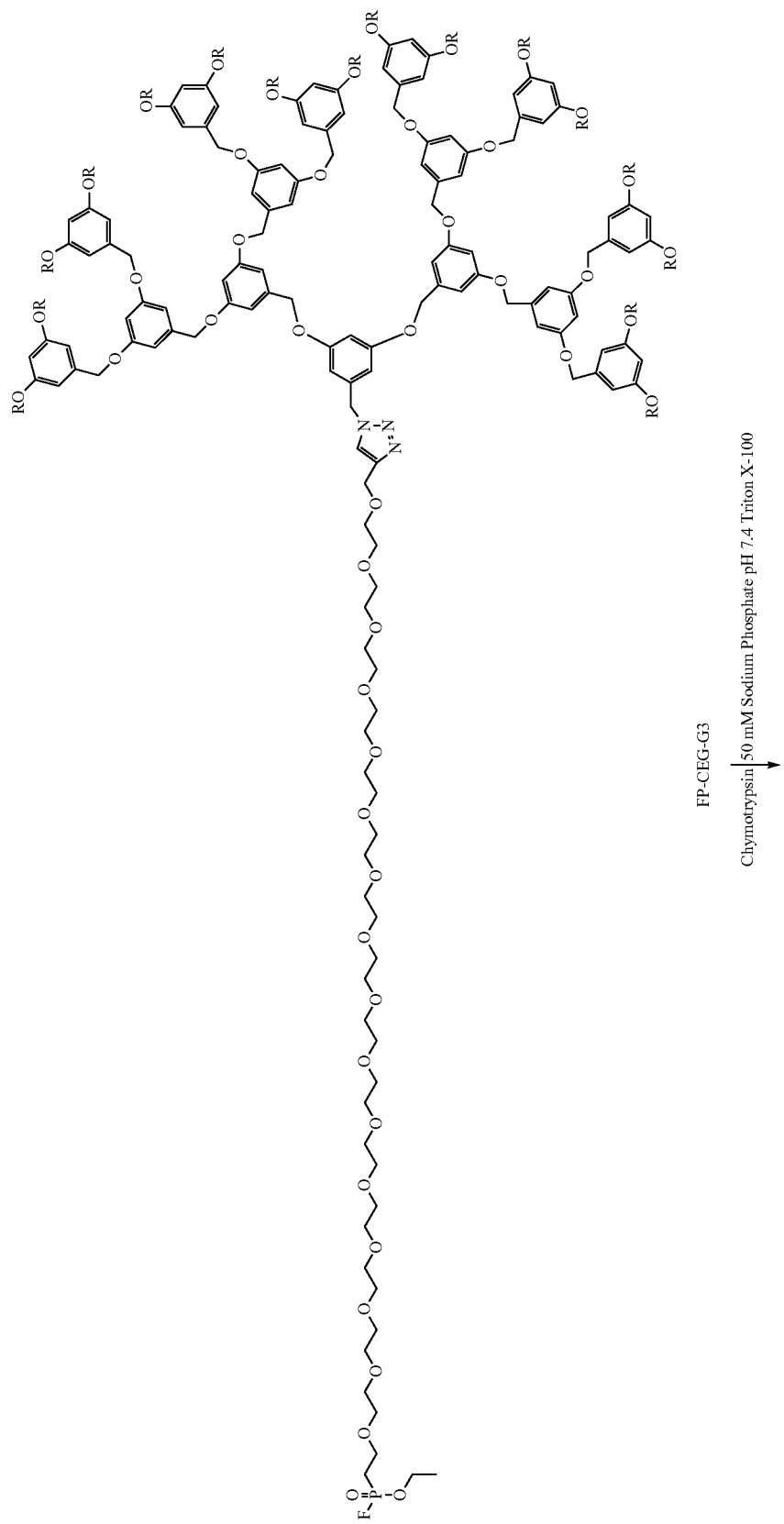

-continued
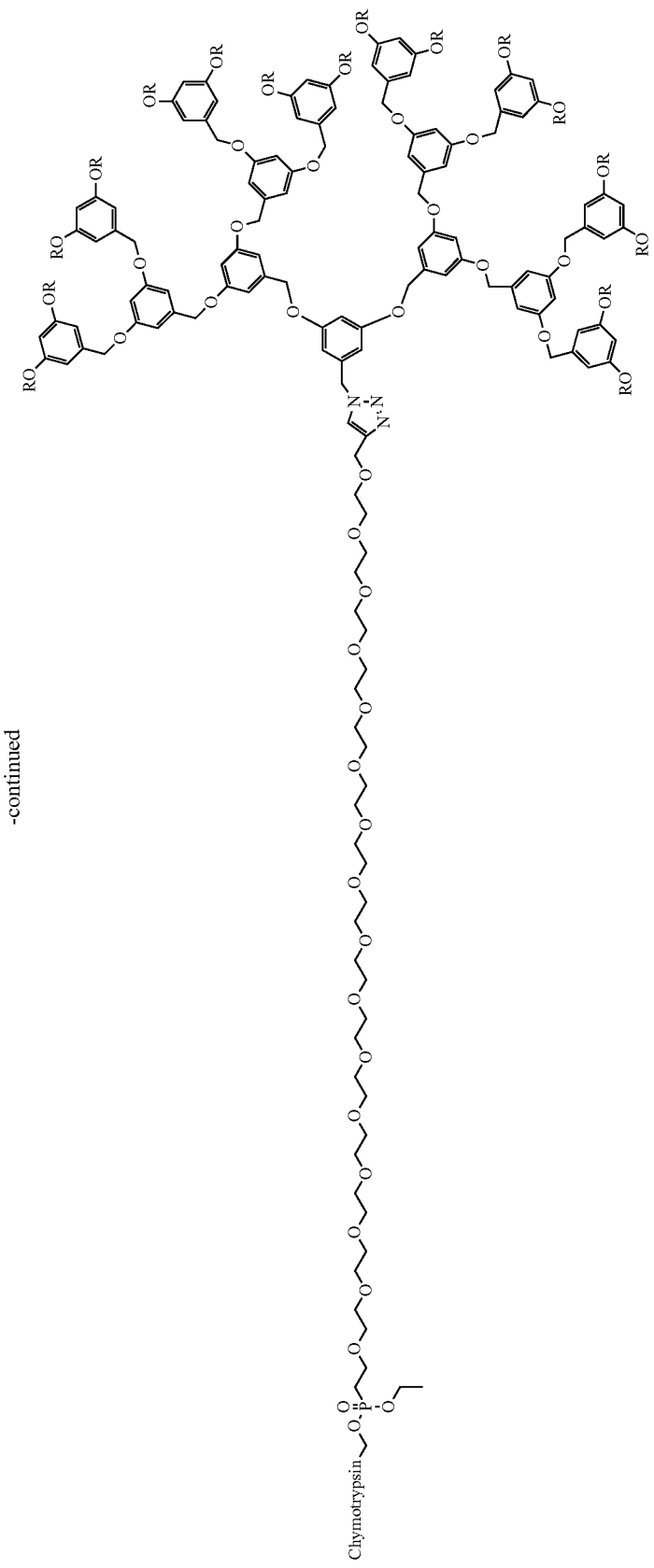
Chy-CEG-G3
R = C6H13

The Chy-CEG-G3 protein conjugates were synthesized and purified by the general procedure described in 1A to 1C.

3.1.3. Synthesis and Purification of Chy-CEG-G4 Protein Conjugates (Scheme 11)

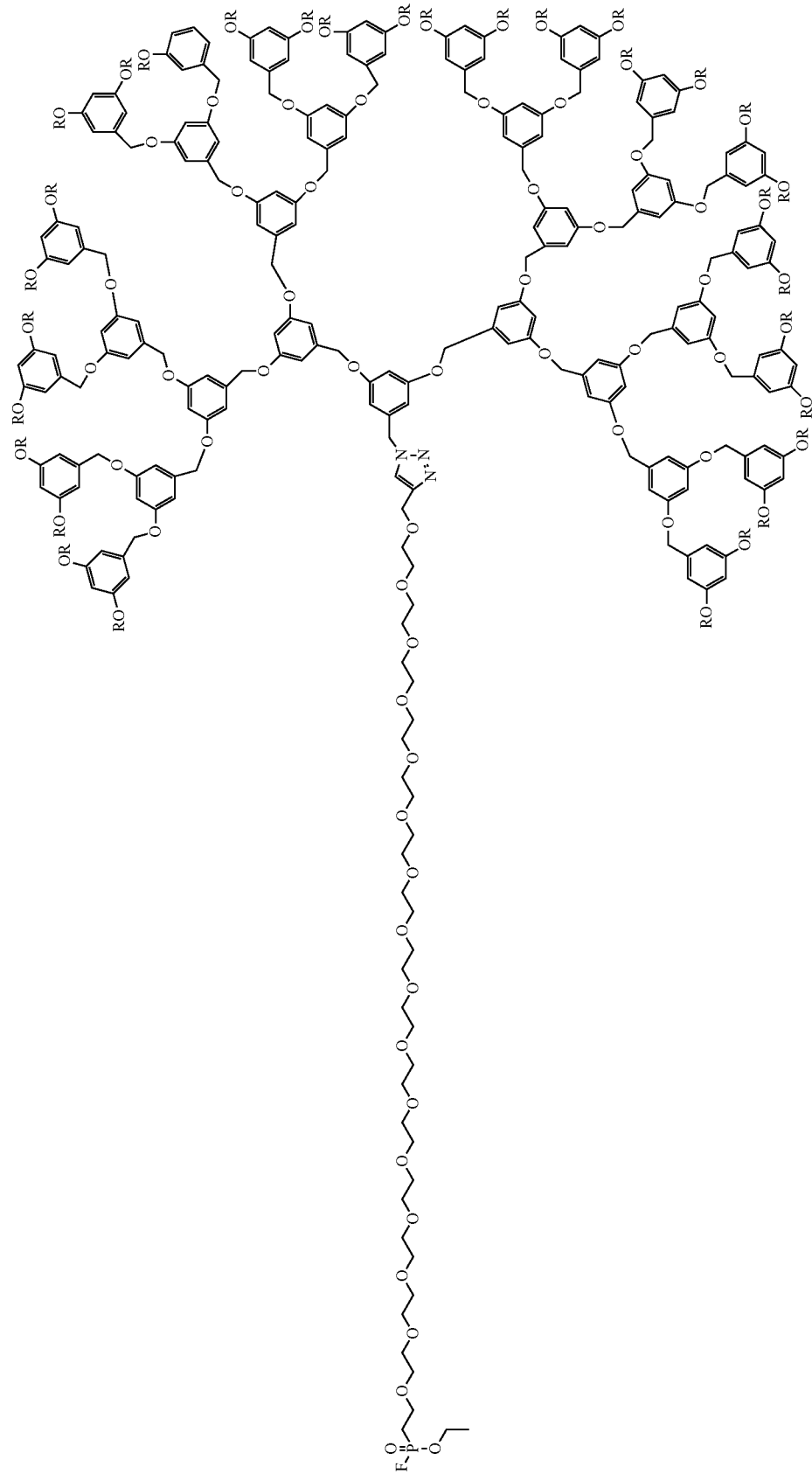

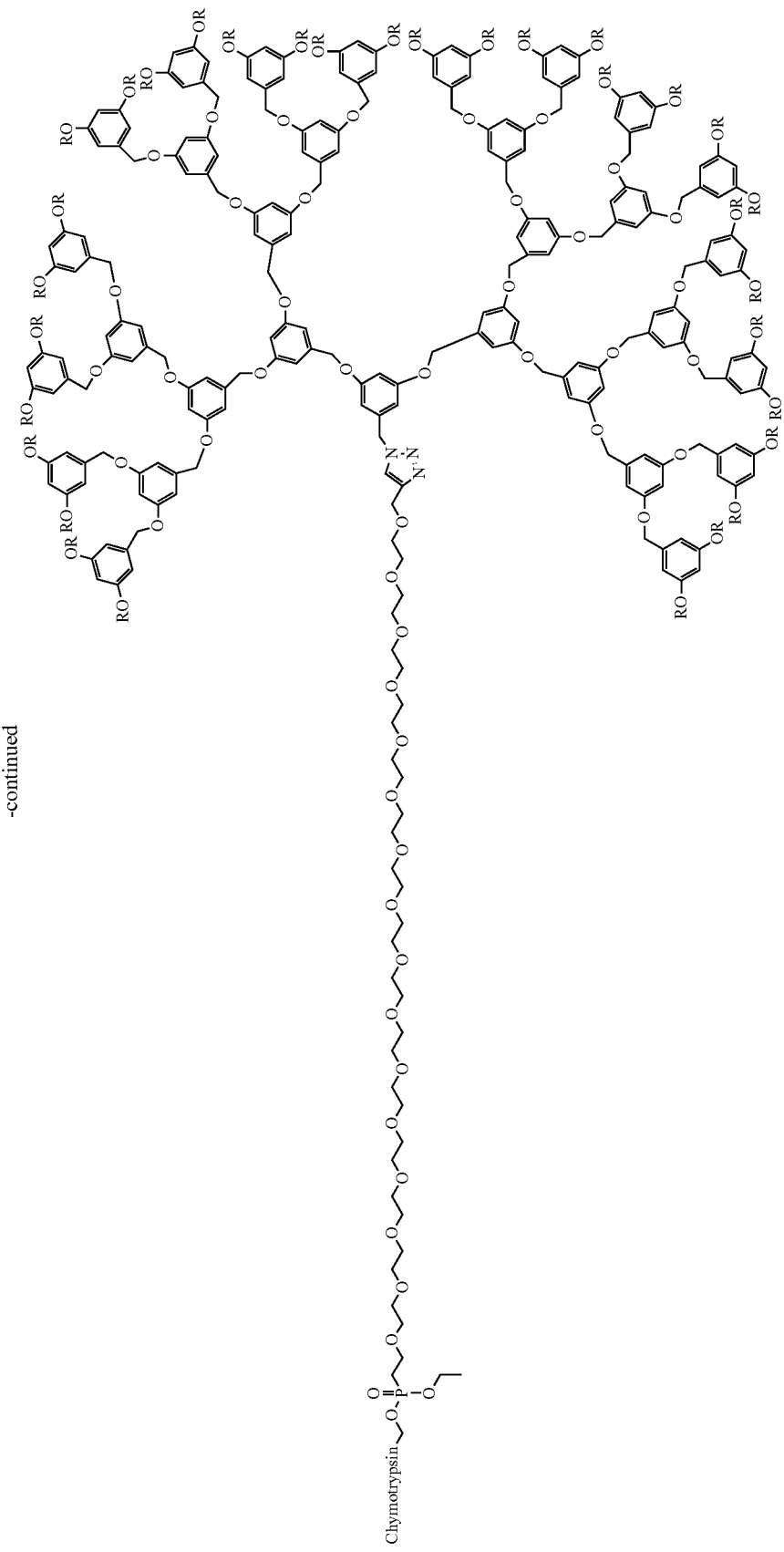

The Chy-CEG-G4 protein conjugates were synthesized general procedure described in 1A. However, the conjugates could not be purified due to its extreme hydrophibicity.

3.4 Synthesis and Purification of Try-CEG-G1 Protein Conjugates (Scheme 12).

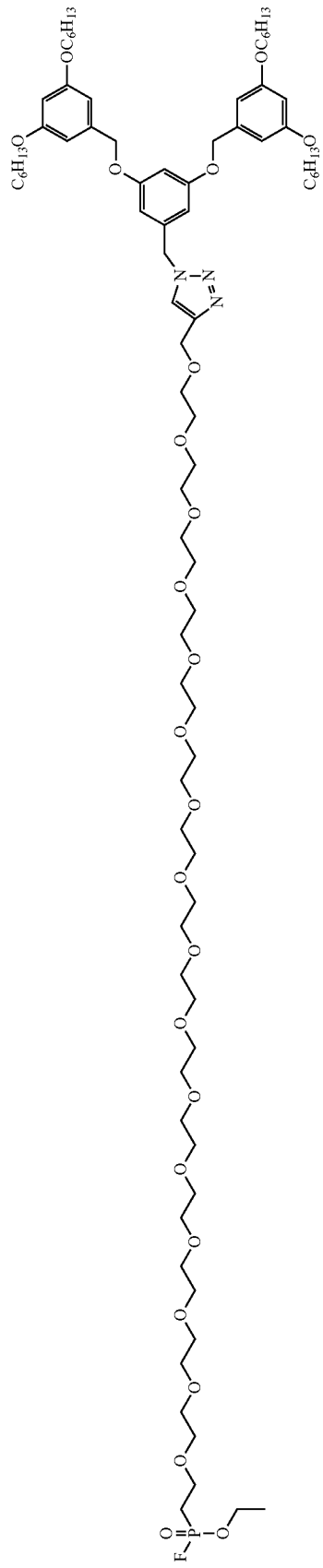
FP-CEG-G1
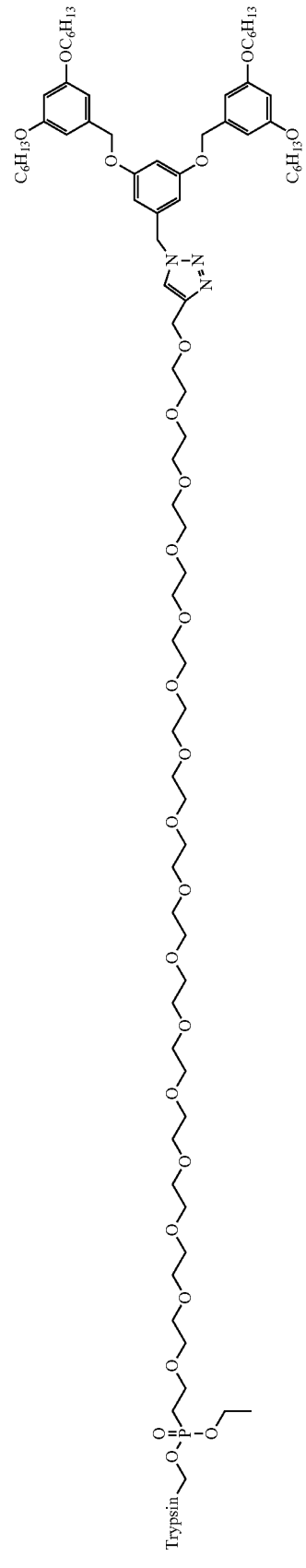
Try-CEG-G1

The Try-CEG-G1 protein conjugates were synthesized and purified by the general procedure described in 1A to IC.

3.5 Synthesis and Purification of Sub-CEG-G1 Protein Conjugates (Scheme 13)

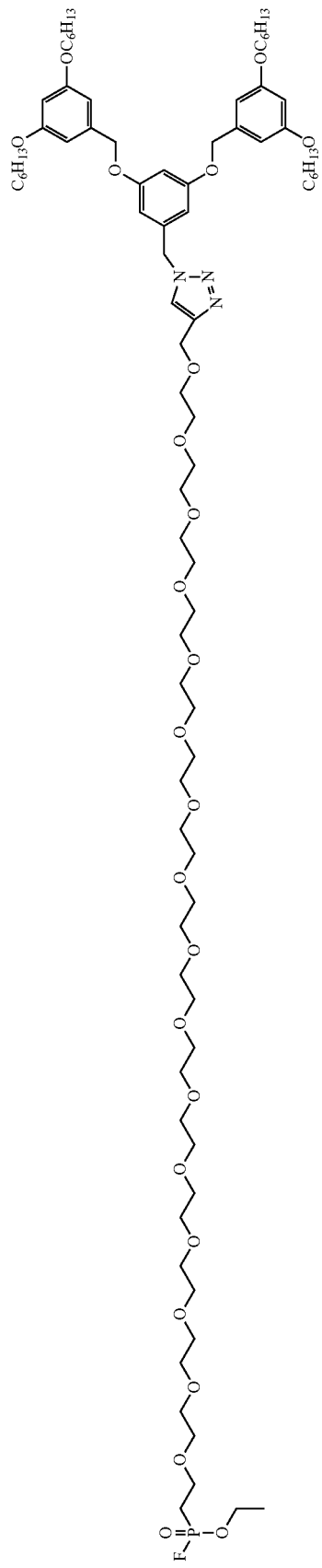
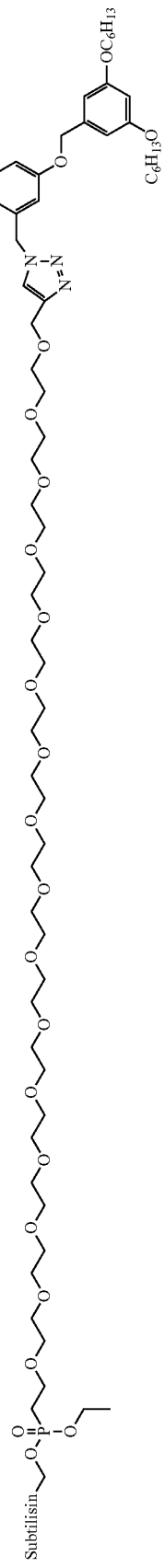

The Sub-CEG-G1 protein conjugates were synthesized and purified by the general procedure described in 1 A to IC.

3.6: Synthesis and Purification of ProK-CEG-G1 Protein Conjugates (Scheme 14)

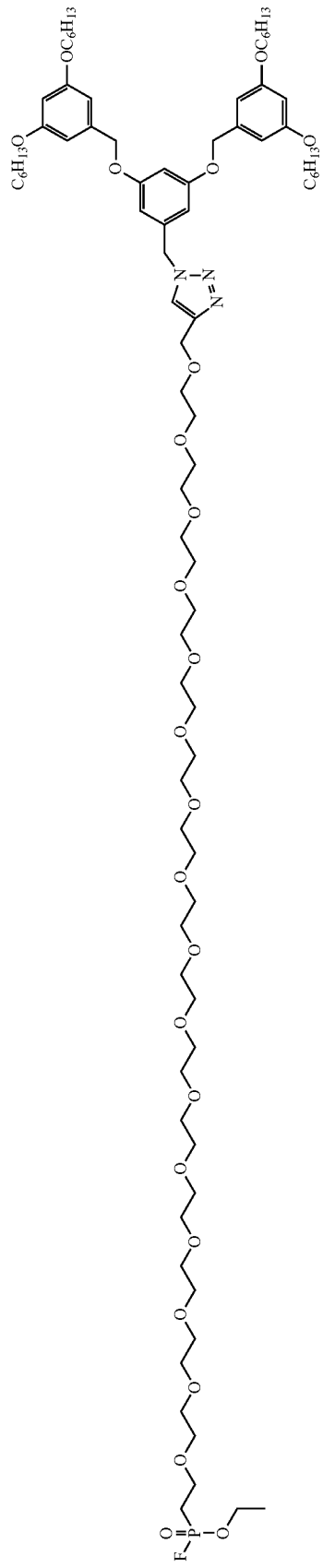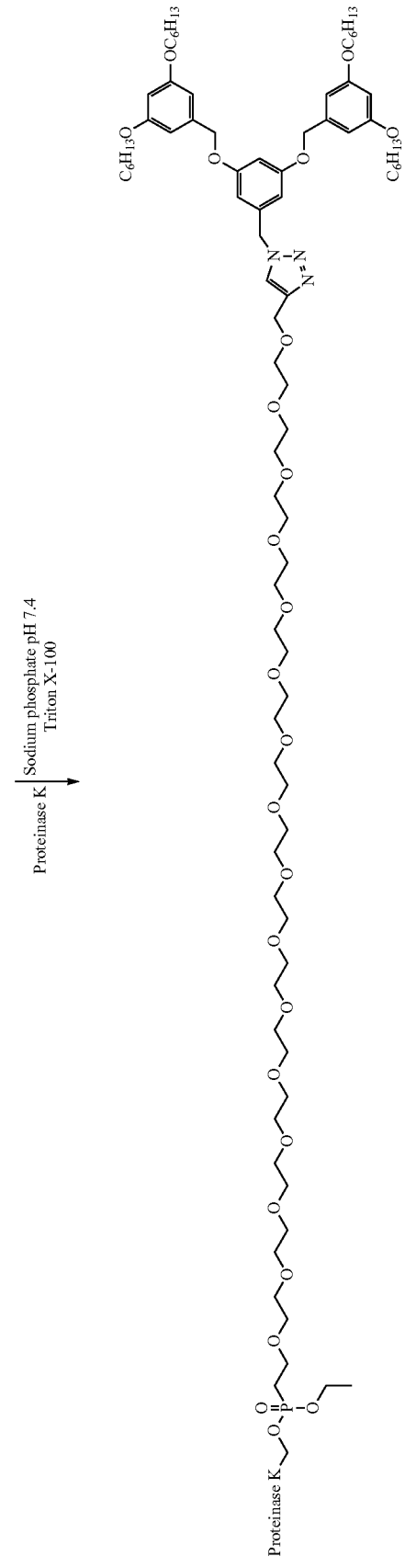

The ProK-CEG-G1 protein conjugates were synthesized and purified by the general procedure described in 1A to 1C.

The self-assembly of the protein-dendron conjugates to supramolecular assemblies prepared by the process depicted in Schemes 6-12 were characterized by Maldi-TOF (FIGS. 2 to 8)

Example 4: DLS and SEC of Protein and Dendron Conjugates 4.1: SEC Comparison for G1, G2, G3 and G4

To get an estimate of the sizes of the generation dependent supramolecular assemblies standard SEC runs were performed in Superdex-200 10/300 GL with 50 mM sodium phosphate containing 1M NaCl as buffer. All conjugates (purified and lyophilized) were dissolved individually in milli Q water (5 mg/mL) and 0.5 mL was injected.

4.2: DLS comparison for G1, G2, G3 and G4

Analysis of generation dependent supramolecular assemblies of protein-dendron conjugates was done in solution state using Dynamic Light Scattering (DLS) using Zetasizer Nano2590 (Malvern, UK). Protein samples (10 mg/mL except G4 which was done at 2 mg/mL) were prepared in 50 mM sodium phosphate pH:7.4. 1 mL of sample was taken in disposable polystyrene cells and then the mean particle size of the particles was measured at 90° scattering angle.

4.3: SEC-MALS

SEC-MALS analyses of the protein complexes were performed on a Superdex200 10/300 GL column (GE Healthcare) connected to an Agilent HPLC system equipped with the 18-angle light scattering detector (Wyatt Dawn HELIOS 11) and a refractive index detector (Wyatt OptilabTrEX). The system was calibrated with BSA at a concentration of 2 mg/mL; 100 µL of the protein conjugates at concentrations 5 mg/mL were injected, and the molecular weights were calculated using ASTRA software (Wyatt Technologies).

Figure 9:
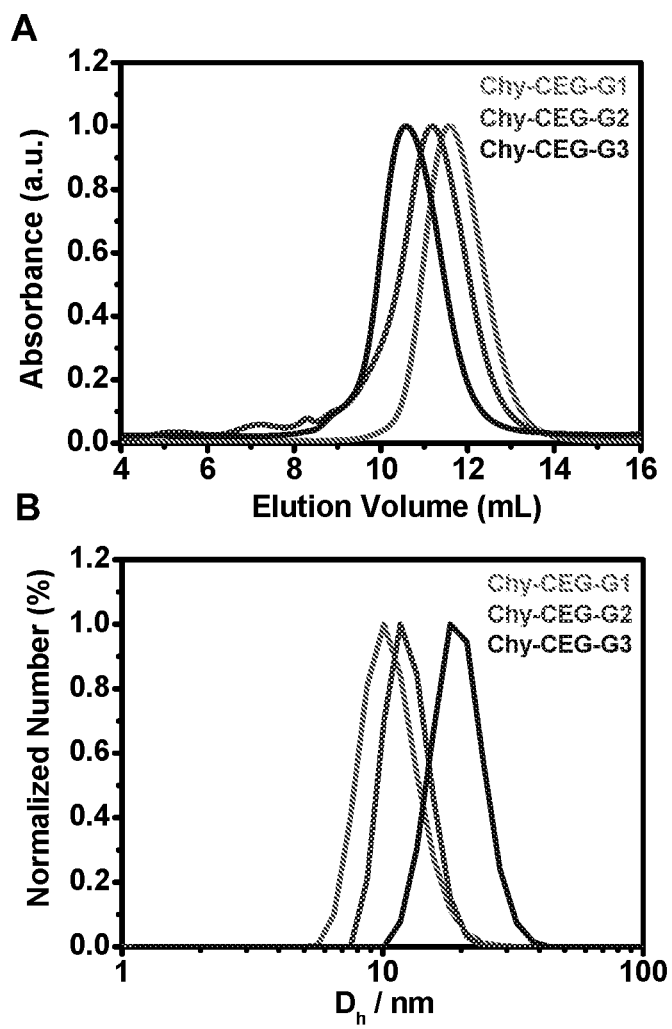
FIG. 9 depict self-assembly studies of dendron variants of protein-dendron conjugates (a) SEC data, (b) DLS data FIG. 10 depict self-assembly studies of head variants of protein-dendron conjugates (a) SEC data, (b) DLS data FIG. 11 (a, b) depicts SEC-MALS measurements of head and tail variants of protein-dendron conjugates.
Figure 10:
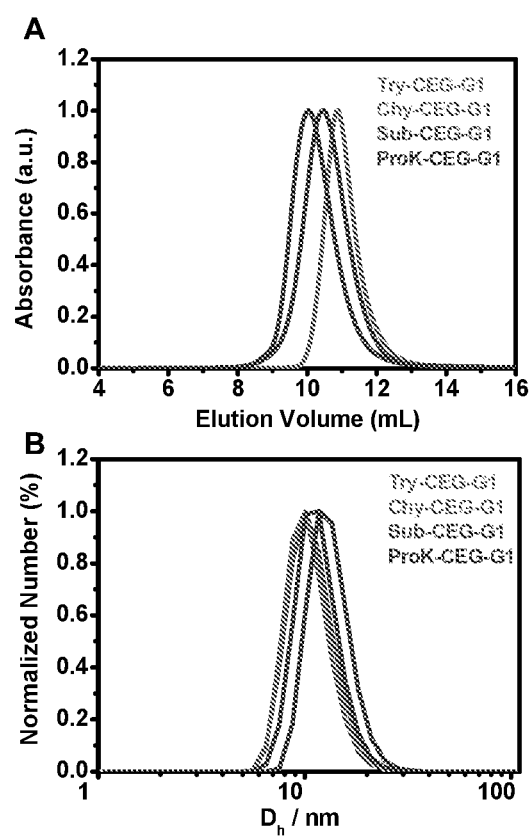
Figure 11A:
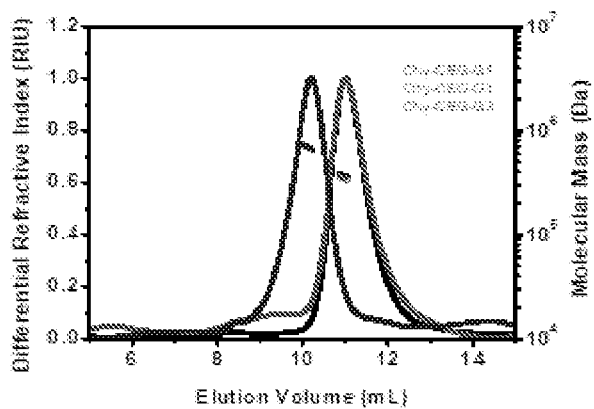
Figure 11B:
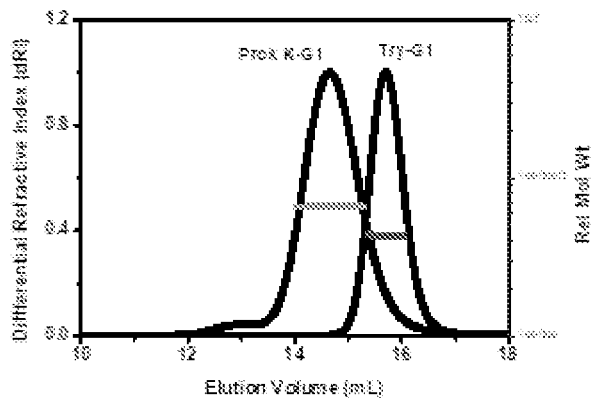
Figure 12:
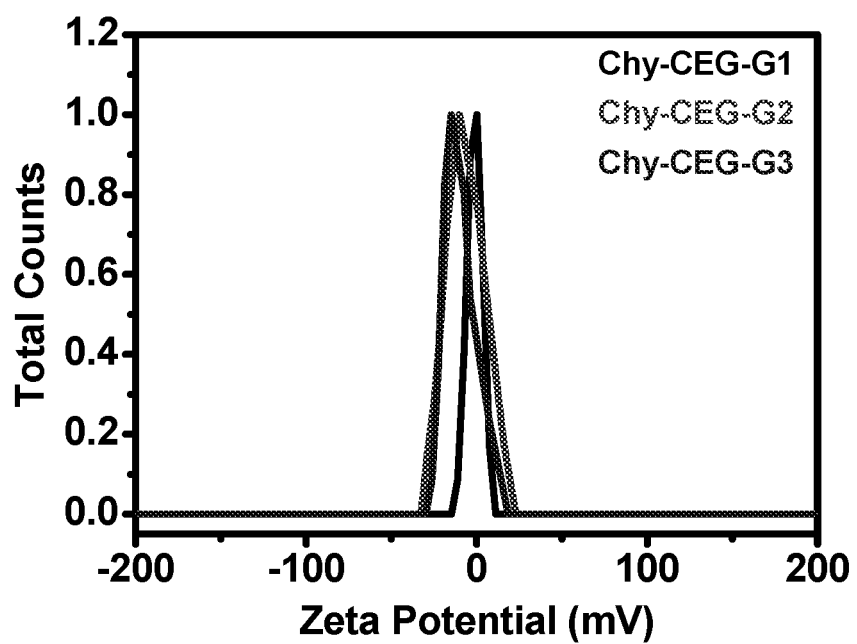
FIG. 12 depict zeta potential studies protein-dendron conjugates SEC-MALS data for dendron variants.

Results:

The DLS measurements reveals the interesting trend in the hydrodynamic radii (Rh) of protein-dendron complexes. The Chy-CEG-G1 and Chy-CEG-G2 complexes showed the similar radius, i.e., 5.45, and 5.85 nm respectively, whereas the Rh of the Chy-CEG-G3 complex found to be 9 nm which is two folds larger than Chy-CEG-G1 and Chy-CEG-G2 complexes (FIG. 9b). This study shows, the size of protein-dendron complexes increases with increase in the generation and emphasizes the effect of dendrimer volume on the size of proteindendron complexes. Further, to explore the molecular mass and oligomeric state of protein-dendron complexes, analytical SEC was performed. The studies unveiled that all four conjugates eluted at lower elution volumes indicative of large protein complexes. The Chy-CEG-G1 and Chy-CEG-G2 complexes eluted at the same elution volume (10.8 mL); whereas, Chy-CEG-G3 eluted at 9.53 mL (FIG. 9a). The elution volume in SEC experiment manifests that the Chy-CEG-G1 and Chy-CEG-G2 complexes are of similar size, and Chy-CEG-G3 forms the larger assembly than Chy-CEG-G1 and Chy-CEG-G2. Analytical SEC studies also showed the similar trend as the DLS results. The SEC data for protein variants revealed that the elution volume of Try-CEG-G1 and Chy-CEG-G1 (10.8 mL) are similar while the ProK-CEG-G1 (10.0 mL) elutes at the lowest elution and Sub-CEG-G1 elutes at 10.4 mL (FIG. 9a). This indicates that ProK-CEG-G1 forms the biggest complex in the protein variants family. The DLS studies for the protein variants also revealed the same trend as SEC (FIG. 9b).

The self-assembly data of protein-dendron conjugates of the present invention is further summarized in Table 1 below:

| Protein-dendron conjugate | Elution Vol from SEC (mL) | Mol wt from SEC - MALS (kDa) | Oligomeric state from SEC-MALS (mer) | Hydrodynamic diameter (Dh) DLS (nm) |
|---|---|---|---|---|
| Library 1: Dendron variants | | | | |
| Chy-CEG-G1 (26,997 Da) | 11.6 | 360 | 13 | 10.1 |
| Chy-CEG-G2 (27,858 Da) | 11.2 | 350 | 12 | 11.7 |
| Chy-CEG-G3 (29,562 Da) | 10.6 | 690 | 26 | 18.1 |
| Library 2: Protein variants | | | | |
| Try-CEG-G1 (24,858 Da) | 10.9 | 430 | 16 | 10.0 |
| Sub-CEG-G1 (28,875 Da) | 10.5 | — | — | 11.7 |
| Prok-CEG-G1 (30,490 Da) | 10.0 | 660 | 22 | 13.4 |

Any patents or publications mentioned in this specification are indicative of the levels of those skilled in the art to which the invention pertains. Further, these patents and publications are incorporated by reference herein to the same extent as if each individual publication was specifically and individually incorporated by reference. One skilled in the art will appreciate readily that the present invention is well adapted to carry out the objects and obtain the ends and advantages mentioned, as well as those objects, ends and advantages inherent herein. Changes therein and other uses which are encompassed within the spirit of the invention as defined by the scope of the claims will occur to those skilled in the art.

We claim:

1. A monodisperse protein-dendron conjugate of Formula I:

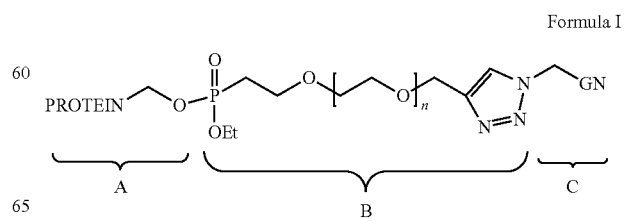

Formula I

111 wherein:

hydrophilic protein (A) is selected from the group consisting of serine proteases, cysteine proteases, aspartic proteases, metalloproteases, fusion proteins composed of a serine protease and another functional protein, an antibody, and a peptide;

a hydrophobic benzyl ether dendrimer Gn (C) is a dendrimer having formula G2, G3, or G4 represented by:

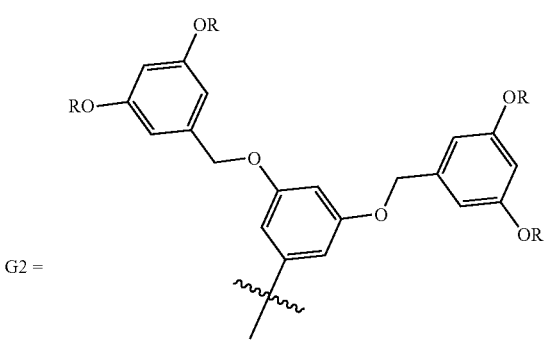

G2 =

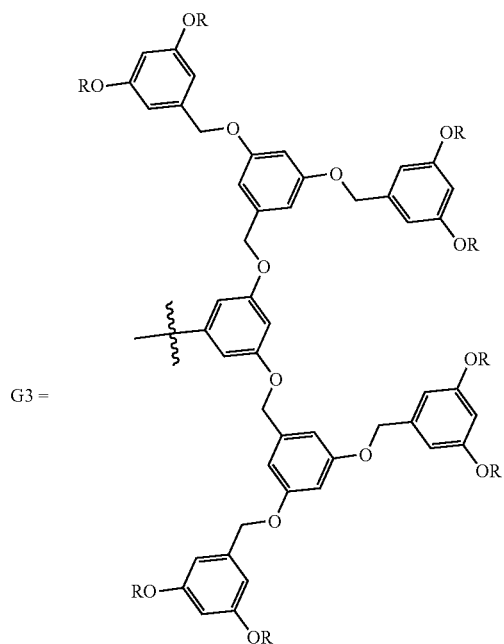

G3 =

G4 =

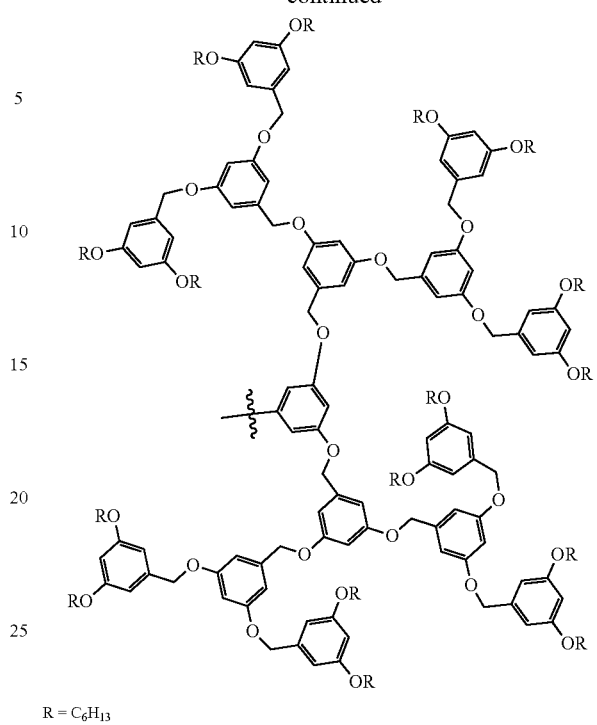

R = C₆H₁₃ n is 1 to 30;

wherein molecular weight of macromolecular amphiphilic activity-based probe (MAABP) is in a range of 2-8 kDa consisting of a fluorophosphonate of a monodisperse oligoethylene glycol as a hydrophilic spacer (B) and the hydrophobic benzyl ether dendrimer Gn (C).

2. The monodisperse protein-dendron conjugate as claimed in claim 1, wherein the size of the supramolecular assembly ranges from 10-20 nm.

3. The monodisperse protein-dendron conjugate as claimed in claim 1, wherein the monodisperse protein-dendron conjugate is of Formula IA:

Formula Ia

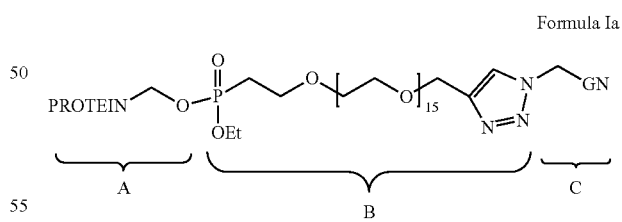

wherein:

hydrophilic protein (A) is selected from the group consisting of serine proteases, cysteine proteases, aspartic proteases, metalloproteases, fusion proteins composed of a serine protease and another functional protein, an antibody, and a peptide;

a hydrophobic benzyl ether dendrimer Gn (C) is a dendrimer having formula G2, G3, or G4 represented by:

113
114
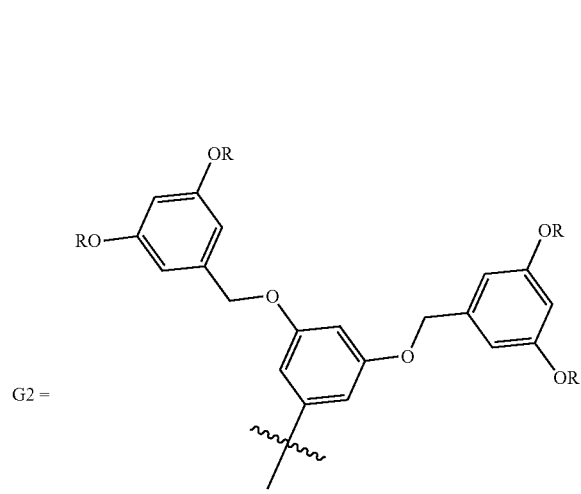
G2 =
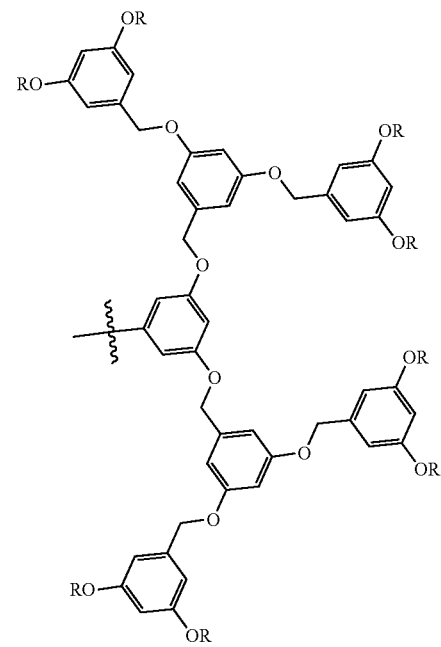
G3 =
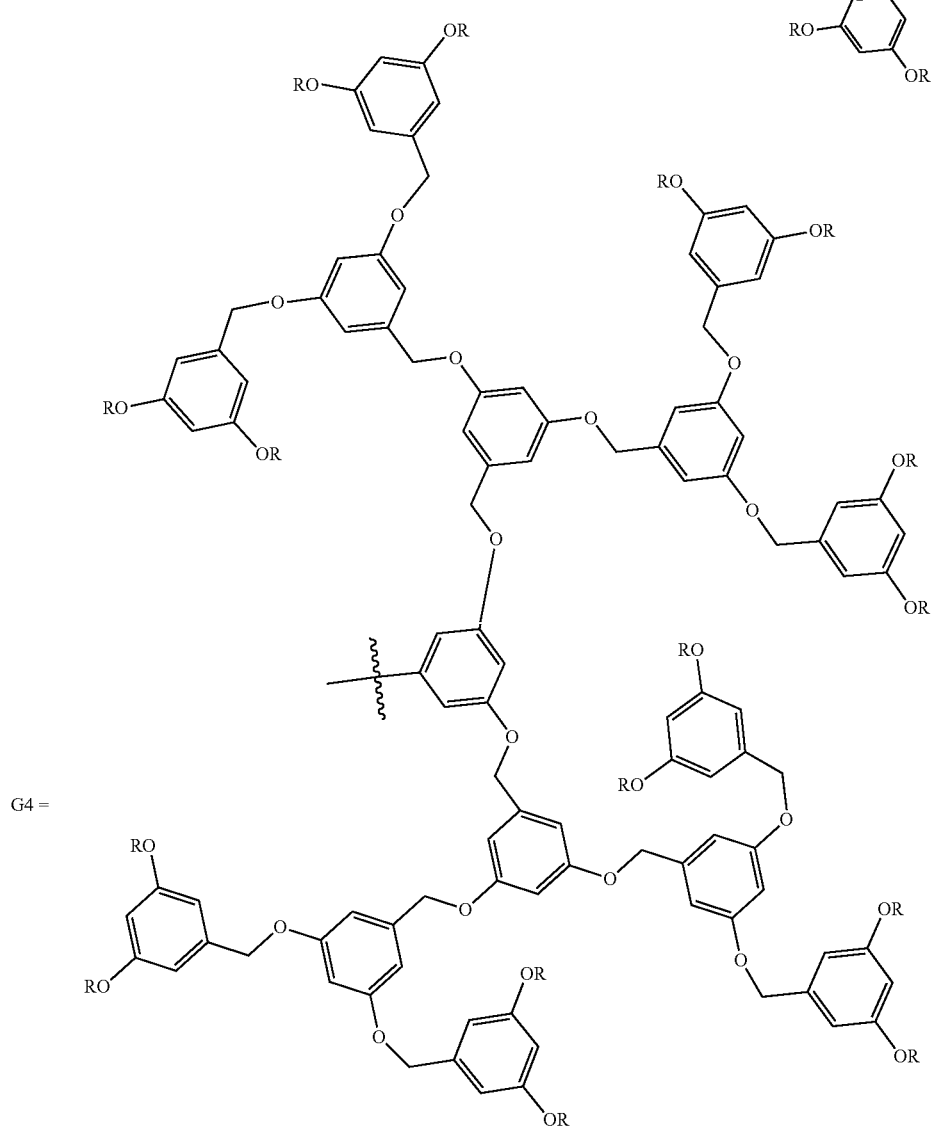
G4 =
R = C$_6$H$_{13}$ wherein molecular weight of macromolecular amphiphilic activity-based probe (MAABP) is in a range of 2-8 kDa consisting of a fluorophosphonate of monodisperse cetylethylene glycol as hydrophilic spacer (B) and the hydrophobic benzyl ether dendrimer Gn (C).

4. A monodisperse protein-dendron conjugate which self-assembles to form a supramolecular protein assembly, comprising:

i. a conjugate of chymotrypsin and the MAABP of (Chy-diethyl (1-(1-(3,5-bis((3,5-bis(hexyloxy)benzyl)oxy) benzyl)-1H-1,2,3-triazol-4-yl)-2,5,8,11,14,17,20,23, 26,29,32,35,38,41,44,47-hexadecaoxanonatetracontan-49-yl) phosphonate);

ii. a conjugate of chymotrypsin and the MAABP of (Chy-diethyl (1-(1-(3,5-bis((3,5-bis((3,5-bis (hexyloxy) benzyl)oxy) benzyl)oxy) benzyl)-1H-1,2,3-triazol-4-yl)-2,5,8,11,14,17,20,23,26,29,32,35,38,41,44, 47-hexadecaoxanonatetracontan-49-yl)phosphonate);

iii. a conjugate of chymotrypsin and the MAABP of (Chy-CEG-ethyl (1-(1-(3,5-bis((3,5-bis ((3,5-bis ((3,5-bis (hexyloxy) benzyl) oxy) benzyl)oxy) benzyl)oxy) benzyl)-1H-1,2,3-triazol-4-yl)-2,5,8,11,14,17,20,23, 26,29,32,35,38,41,44,47-hexadecaoxanonatetracontan-49-yl)phosphonate;

iv. a conjugate of trypsin and the MAABP of Try-diethyl (1-(1-(3,5-bis((3,5-bis(hexyloxy)benzyl)oxy)benzyl)- 1H-1,2,3-triazol-4-yl)-2,5,8,11,14,17,20,23,26,29,32, 35,38,41,44,47-hexa decaoxanonatetracontan-49-yl) phosphonate;

v. a conjugate of substilin and the MAABP of (Sub-diethyl (1-(1-(3,5-bis((3,5-bis(hexyloxy)benzyl)oxy) benzyl)-1H-1,2,3-triazol-4-yl)-2,5,8,11,14,17,20,23, 26,29,32,35,38,41,44,47-hexa decaoxanonatetracontan-49-yl) phosphonate);

vi. a conjugate of proteinase K and the MAABP of (ProK-diethyl (1-(1-(3,5-bis((3,5-bis(hexyloxy) benzyl)oxy) benzyl)-1H-1,2,3-triazol-4-yl)-2,5,8,11, 14,17, 20,23,26,29,32,35,38,41,44,47-hexa decaoxanonatetracontan-49-yl) phosphonate).

5. A process for preparation of a monodisperse protein-dendron conjugate of Formula (I), comprising:

Formula I

PROTEIN—O—P(=O)(OEt)—O—[CH₂CH₂O]ₙ—triazole—CH₂—GN

A / B / C

G2 = [structure of second generation benzyl ether dendron with 4 OR groups]

G3 = [structure of third generation benzyl ether dendron with 8 OR groups]

-continued

G4 =

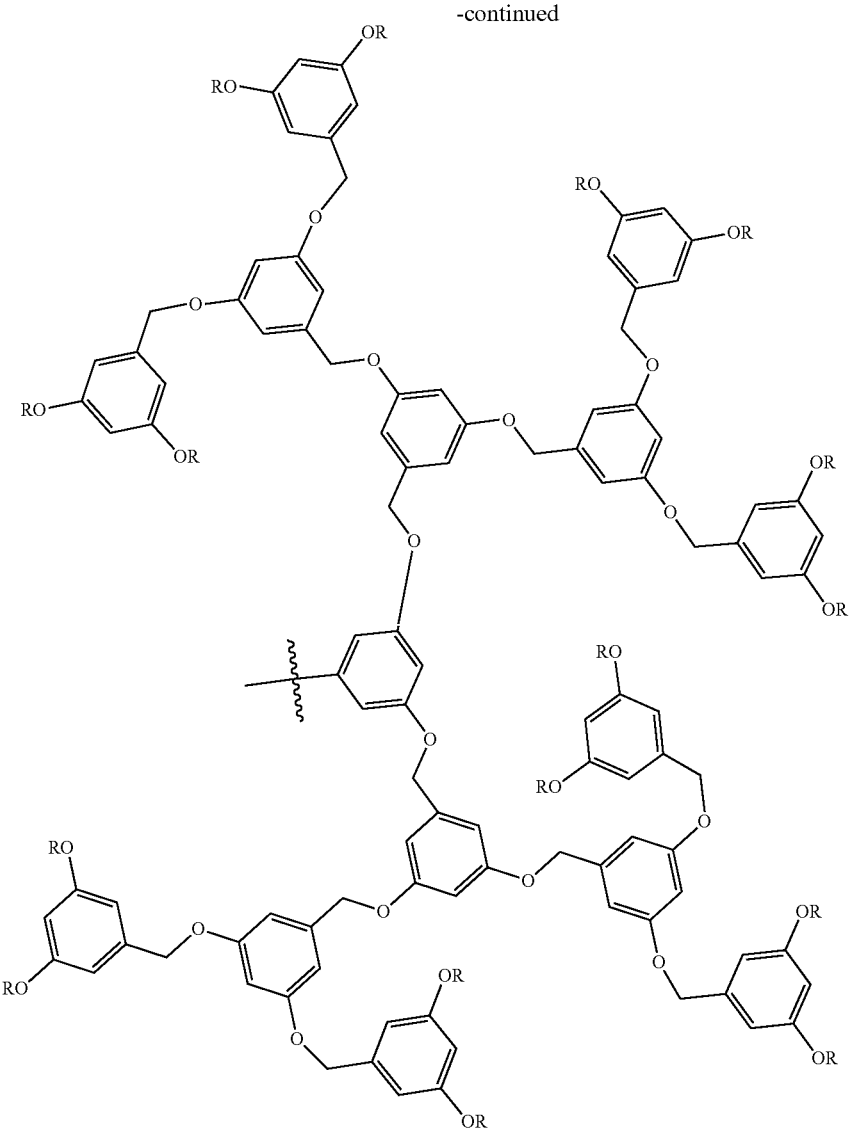

R = C6H13 i. reacting a hydrophobic G1-G4 azide dendrimer dissolved in degassed solvent mixture selected from THF/H2O (1:1) for G1-G2 azide and H2O/CH2Clz/THF (0.25:1:1) for G3-G4 azide with diphosphonate ester of oligoethylene glycol (OEG) spacer using click chemistry followed by deprotection using oxalyl chloride to obtain a monophosphonate ester intermediate;

ii. fluorinating the monophosphonate ester intermediate of step (i) with diethyl amino sulfur triflouride (DAST) to obtain a G1-G4 macromolecular amphiphilic activity based probe (MAABP);

iii. homogenizing the G1-G4 macromolecular amphiphilic activity based probe (MAABP) of step (ii) with a hydrophilic protein (A) solution and scaling up the protein modification for self-assembling followed by purification to obtain generation dependent supra molecular assemblies of protein-dendron conjugate.

6. A composition comprising a monodisperse protein-dendron conjugate of Formula (I) which self-assembles to form generation-dependent supramolecular protein assemblies as claimed in claim 1, Formula I

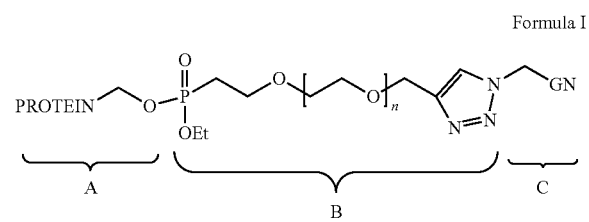

together with pharmaceutically acceptable excipients.

7. The monodisperse protein-dendron conjugate as claimed in claim 1, wherein the serine proteases is chymotrypsin, trypsin, subtilisin, or proteinase K.

* * * * *